US012318404B2

(12) United States Patent
Hoover et al.

(10) Patent No.: US 12,318,404 B2
(45) Date of Patent: Jun. 3, 2025

(54) HYPOCHLORITE FORMULATIONS FOR WOUND HEALING

(71) Applicant: Reoxcyn, LLC, Ogden, UT (US)

(72) Inventors: Andrew Hoover, Pleasant Grove, UT (US); Kurt Richards, Herriman, UT (US)

(73) Assignee: Reoxcyn LLC, Ogden, UT (US)

( * ) Notice: Subject to any disclaimer, the term of this patent is extended or adjusted under 35 U.S.C. 154(b) by 269 days.

(21) Appl. No.: 15/409,379

(22) Filed: Jan. 18, 2017

(65) Prior Publication Data

US 2017/0202877 A1    Jul. 20, 2017

Related U.S. Application Data

(60) Provisional application No. 62/280,613, filed on Jan. 19, 2016.

(51) Int. Cl.
| | |
|---|---|
| *A61K 33/20* | (2006.01) |
| *A61K 8/19* | (2006.01) |
| *A61K 8/24* | (2006.01) |
| *A61K 8/25* | (2006.01) |
| *A61K 8/891* | (2006.01) |
| *A61K 9/00* | (2006.01) |
| *A61K 9/08* | (2006.01) |
| *A61K 45/06* | (2006.01) |
| *A61K 47/02* | (2006.01) |
| *A61K 47/24* | (2006.01) |
| *A61K 47/34* | (2017.01) |
| *A61L 26/00* | (2006.01) |
| *A61Q 19/08* | (2006.01) |
| *C25B 1/26* | (2006.01) |

(52) U.S. Cl.
CPC ............... *A61K 33/20* (2013.01); *A61K 8/19* (2013.01); *A61K 8/24* (2013.01); *A61K 8/25* (2013.01); *A61K 8/891* (2013.01); *A61K 9/0014* (2013.01); *A61K 9/08* (2013.01); *A61K 45/06* (2013.01); *A61K 47/02* (2013.01); *A61K 47/24* (2013.01); *A61K 47/34* (2013.01); *A61L 26/0004* (2013.01); *A61Q 19/08* (2013.01); *C25B 1/26* (2013.01); *A61K 2800/81* (2013.01)

(58) Field of Classification Search
None
See application file for complete search history.

(56) References Cited

U.S. PATENT DOCUMENTS

| | | | |
|---|---|---|---|
| 1,200,165 A | 3/1916 | Burgess | |
| 4,236,992 A | 12/1980 | Themy | |
| 4,316,787 A | 2/1982 | Themy | |
| 4,671,955 A | 6/1987 | Palinczar | |
| 4,810,344 A | 3/1989 | Okazaki | |
| 4,956,184 A | 9/1990 | Kross | |
| 5,334,383 A | 8/1994 | Morrow | |
| 5,507,932 A | 4/1996 | Robinson | |
| 5,674,537 A | 10/1997 | Morrow | |
| 6,007,686 A | 12/1999 | Welch | |
| 6,042,618 A * | 3/2000 | Berndt | C11D 1/82 |
| | | | 134/19 |
| 6,114,398 A | 9/2000 | Ratcliff | |
| 6,117,285 A | 9/2000 | Welch | |
| 6,333,054 B1 | 12/2001 | Rogozinski | |
| 7,108,997 B2 | 9/2006 | Kettle | |
| 7,276,255 B2 * | 10/2007 | Selkon | A61P 17/02 |
| | | | 424/661 |
| 7,622,434 B2 * | 11/2009 | Rogozinski | A61L 26/008 |
| | | | 510/130 |
| 7,691,249 B2 | 4/2010 | Daly | |
| 8,062,501 B2 | 11/2011 | Omasa | |
| 8,323,252 B2 | 12/2012 | Alimi | |
| 8,518,382 B2 | 8/2013 | Speronello et al. | |
| 8,673,297 B2 | 3/2014 | Speronello et al. | |
| 8,784,900 B2 | 7/2014 | Northey | |
| 9,072,793 B2 | 7/2015 | Eckert et al. | |
| 9,175,141 B2 | 11/2015 | Wray et al. | |
| 9,474,768 B1 | 10/2016 | Richards | |
| 9,833,406 B1 | 12/2017 | Richards | |
| 2002/0114849 A1 | 8/2002 | Camper et al. | |
| 2004/0137078 A1 * | 7/2004 | Najafi | C02F 1/4618 |
| | | | 424/661 |
| 2005/0089537 A1 | 4/2005 | Birnholz | |
| 2005/0196462 A1 | 9/2005 | Alimi | |

(Continued)

FOREIGN PATENT DOCUMENTS

| | | |
|---|---|---|
| CN | 102167997 | 6/2013 |
| EP | 0335584 | 10/1989 |

(Continued)

OTHER PUBLICATIONS

Ahmed et al.; "Effectiveness of 0.025% Dakin's Solution Versus 1% Silver Sulphadiazine for Treatment of Partial Thickness Burns," Ann. Pak. Inst. Med. Sci. 2011; 7(3): 127-132.*
Dow Corning® presentation titled "What are Silicones?", Retrieved from http://www.doorirng.com/data/Silicone%20Chemistry.pdf on Jun. 4, 2019 (pp. 1-29). (Year: 2019).*
Liu, et al., Effects of Exogenous Silicon on the Activities of Antioxidant Enzymes and Lipid Peroxidation in Chilling-Stressed Cucumber Leaves, JIA, 2009, vol. 8(9), p. 1075-1086. (Year: 2009).*
Balakhnina, T. et al., Effects of silicon on plant resistance to environmental stresses: review, Int. Agrophys., 2013/27,225-232. (Year: 2013).*
O'Lenick, Anthony Jr., Silicone Spectator, 1999, pp. 1-23. (Year: 1999).*

(Continued)

*Primary Examiner* — Tigabu Kassa
*Assistant Examiner* — Ivan A Greene
(74) *Attorney, Agent, or Firm* — KNOBBE, MARTENS, OLSON & BEAR, LLP

(57) ABSTRACT

A formulation is disclosed for use in wound healing. The formulation may include hypochlorous acid, a silicone polymer or blend thereof, sodium phosphate, hydrochloric acid, and sodium magnesium silicate. Methods of using and making the wound healing formulation are also disclosed.

20 Claims, 9 Drawing Sheets

(56) References Cited

U.S. PATENT DOCUMENTS

| | | | |
|---|---|---|---|
| 2006/0051387 A1* | 3/2006 | Green | A47L 13/51 424/414 |
| 2006/0241546 A1 | 10/2006 | Alimi | |
| 2007/0021213 A1 | 1/2007 | Foe | |
| 2007/0172412 A1 | 7/2007 | Hratko et al. | |
| 2007/0243264 A1* | 10/2007 | Garabedian | A01N 59/00 424/661 |
| 2007/0281008 A1 | 12/2007 | Lin et al. | |
| 2008/0003171 A1 | 1/2008 | Smith et al. | |
| 2008/0008621 A1 | 1/2008 | Masahiro et al. | |
| 2008/0110803 A1* | 5/2008 | Veltri | C10G 1/045 208/390 |
| 2008/0160612 A1 | 7/2008 | Selkon | |
| 2008/0206371 A1* | 8/2008 | Fontaine | A61P 17/02 424/744 |
| 2009/0028811 A1 | 1/2009 | Potter | |
| 2009/0068122 A1 | 3/2009 | Shira et al. | |
| 2009/0148342 A1 | 6/2009 | Bromberg et al. | |
| 2009/0169646 A1 | 7/2009 | Bosch et al. | |
| 2009/0258083 A1 | 10/2009 | Calderon | |
| 2010/0012132 A1 | 1/2010 | Harrison et al. | |
| 2010/0078331 A1 | 4/2010 | Scherson | |
| 2010/0196454 A1* | 8/2010 | Keller | A61L 15/44 514/648 |
| 2010/0197748 A1 | 8/2010 | Schwarz et al. | |
| 2010/0274176 A1* | 10/2010 | Baumgart | A61K 33/24 604/20 |
| 2010/0285151 A1 | 11/2010 | Goldan | |
| 2010/0330203 A1* | 12/2010 | Kross | A61K 9/0019 424/661 |
| 2011/0052506 A1 | 3/2011 | Abel et al. | |
| 2011/0121110 A1 | 5/2011 | Field | |
| 2012/0046556 A1 | 2/2012 | Block | |
| 2012/0148516 A1* | 6/2012 | Abel | A61Q 17/00 424/62 |
| 2012/0164235 A1* | 6/2012 | Northey | A61K 47/02 424/600 |
| 2012/0237616 A1* | 9/2012 | Panicheva | A01N 59/00 424/661 |
| 2013/0095138 A1* | 4/2013 | Norton | A61K 33/40 424/278.1 |
| 2013/0150451 A1* | 6/2013 | Salamone | A61P 43/00 514/635 |
| 2013/0164228 A1 | 6/2013 | Stanislav et al. | |
| 2013/0168260 A1 | 7/2013 | Scherson et al. | |
| 2013/0236563 A1 | 9/2013 | Samuelson | |
| 2013/0243883 A1* | 9/2013 | Norton | C25B 1/30 424/615 |
| 2014/0044800 A1 | 2/2014 | Robinson | |
| 2014/0328946 A1 | 11/2014 | Northey | |
| 2014/0369953 A1 | 12/2014 | Purschwitz | |
| 2015/0017257 A1 | 1/2015 | Megumi et al. | |
| 2015/0093451 A1 | 4/2015 | Neiman | |
| 2015/0099010 A1 | 4/2015 | Hoover | |
| 2015/0118180 A1 | 4/2015 | Hoover | |
| 2015/0125543 A1 | 5/2015 | Croke et al. | |
| 2015/0246131 A1 | 9/2015 | Romanoschi et al. | |
| 2015/0250704 A1 | 9/2015 | Romanoschi et al. | |
| 2016/0198720 A1* | 7/2016 | Yoshida | A23L 3/3463 424/613 |

FOREIGN PATENT DOCUMENTS

| | | | | |
|---|---|---|---|---|
| EP | 1886664 | | 2/2008 | |
| MX | 2016013933 A | * | 7/2017 | C02F 1/467 |
| WO | WO 9934773 | | 7/1999 | |
| WO | WO-2006102680 A2 | * | 9/2006 | A61C 1/0076 |
| WO | WO 2010004699 | | 1/2010 | |
| WO | WO 2015002932 | | 3/2015 | |
| WO | WO 2016/100543 | | 6/2016 | |
| WO | WO 2017127452 | | 7/2017 | |

OTHER PUBLICATIONS

Bleasdale et al.; "The Use of Silicone Adhesives for Scar Reduction," 2015, Wound Healing Society, Advances in Wound Care, vol. 4, No. 7, pp. 422-430. (Year: 2015).*

Van der wal et al.; "Topical Silicone Gel versus Placebo in Promoting the Maturation of Burn Scars: A Randomized Controlled Trial," 2010, American Society of Plastic Surgeons; Plastic and Reconstructive Surgery, vol. 126, No. 2, pp. 524-531. (Year: 2010).*

Rutala et al.; New Disinfection and Sterilization Methods, 2001, Emerging Infectious Diseases, vol. 7, No. 2, pp. 348-353. (Year: 2001).*

Bunyan, John; "The Treatment of Burns by Hypochlorite Solution," 1983, Journal of Tropical Pediatrics, vol. 29, No. 2, pp. 93-94. (Year: 1983).*

Merriam-Webster's Collegiate Dictionary, 11th ed., 2004, entry for "impregnate" p. 625. (Year: 2004).*

Ansel et al.; "Pharmaceutical Dosage Forms and Drug Delivery Systems, 7th ed.," Lippincott, Williams and Wilkins, pp. 414-417. (Year: 1999).*

Sinko, Patrick J.; "Martin's Physical Pharmacy and Pharmaceutical Sciences," Lippincott, Williams and Wilkins, pp. 119-141 and 143-160. (Year: 2006).*

Kerckhove et al.; "Silicones in the rehabilitation of burns: a review and overview," 2001, Elsevier; Burns, vol. 27, pp. 205-214, (Year: 2001).*

International Search Report and Written Opinion for PCT/US2017/013979, mailed May 2, 2017.

Alnashef et al. Electrochemical Generation of Superoxide In Room-Temperature Ionic Liquids. Electrochemical and Solid State Letters, 4 (11) D16-D18 (2001).

AlNashef et al. Superoxide Electrochemistry in an Ionic Liquid. Ind. Eng. Chem. Res. 2002, 41, 4475-4478.

Bielski et al. Reactivity of H02/02—Radicals in Aqueous Solution. J. Phys. Chem. Ref. Data, vol. 14, No. 4 1985.

Chen, "Novel technologies for the prevention and treatment of dental caries: a patent survey", Expert Opin Ther Pat. May 2010; 20(5): 681-694.

Hayann et al. Generation and stability of superoxide ion in tris(pentafluoroethyl) trifluorophosphate anion-based ionic liquids. J Fluorine Chem. vol. 142, 2012, 83-89.

Hayyan et al. Long term stability of superoxide ion in piperidinium, pyrrolidinium and phosphonium cations-based ionic liquids and its utilization in the destruction of chlorobenzenes. Journal of Electroanalytical Chemistry. vol. 664, 2012, 26-32.

Kahn et al. Spin Traps: In Vitro Toxicity and Stability of Radical Adducts. Free Radical Biology & Medicine, vol. 34, No. 11, pp. 1473-1481, 2003.

Kariduraganavar et al. Ion-exchange membranes: preparative methods for electrodialysis and fuel cell applications. Desalination 197 (2006) 225-246.

Konaka et al. Irradiation of Titanium Dioxide Generates Both Singlet Oxygen and Superoxide Anion. Free Radical Biology & Medicine, vol. 27, Nos. 3/4, pp. 294-300, 1999.

Prasanth, "Antimicrobial Efficacy of Different Toothpastes and Mouthrinses: An In Vitro Study", Dent Res J (Isfahan), 2011 Spring, 8(2); 85-94.

Zoulias et al. A Review on Water Electrolysis last modified Jan. 20, 2006 15:24.

"High purity, activated HCIO Perfect Perio", http://amanodental.com/english/PerfectPerio-how-to-use.pdf, Nov. 2010.

PCT Search Report and Written Opinion for PCT Application No. PCT/US2016/056760, filed Oct. 13, 2016, dated Jan. 16, 2017.

PCT International Search Report in PCT/US2017/051283, mailed Nov. 29, 2017.

* cited by examiner

| + | Anode | e- ↑ | e- ↓ | Cathode | - | |
|---|---|---|---|---|---|---|
| | | | | | | 1st Generation |
| -1.23 V:O$_2$ 4H+ | 4e↑ | 2H$_2$O | 2H+ | 2e↓ | H$_2$ | -0.00V |
| -0.40V:O$_2$ 2H+ | 4e↑ | 4OH- | 2H$_2$O | 2e↓ | H$_2$ 2OH- | -0.83V |
| -0.89V:ClO- H$_2$O | 2e↑ | 2OH- Cl- | 2H$_2$O | 2e↓ | 2H+ H$_2$O$_2$ | 1.76V |
| -1.36 V:Cl$_2$ | 2e↑ | 2Cl- | Na+ | 1e↓ | Na$_{(s)}$ | -2.71V |
| -1.63 V:2HClO 2H+ | 2e↑ | Cl$_2$ 2H$_2$O | O$_2$ | 1e↓ | O$_2$•- 2H$_2$O | -0.33V | 2nd Generation |
| -1.67V:HClO$_2$ 2H+ | 2e↑ | HClO H$_2$O | O$_2$ H+ | 2e↓ | HO$_2$•- | -0.13V |
| -2.07V:O$_3$ 2H+ | 2e↑ | O$_2$ H$_2$O | O$_2$ H+ | 2e↓ | H$_2$O$_2$ | 0.70V |
| -1.18 V:2ClO$_3$ 12H+ | 10e↑ | ICl$_2$ 6H$_2$O | 2HClO 2H+ | 2e↓ | Cl$_2$ 2H$_2$O | 1.63V |
| | | | | | | 3rd Generation+ |
| -1.19 V:ClO$_2$ H+ | 1e↑ | HClO$_2$ 2H$_2$O | HO$_2$•- | 1e↓ | H$_2$O$_2$ | 1.51V |
| -1.18V:ClO$_3$- | 1e↑ | ClO$_2$ H$_2$O | H$_2$ | 2e↓ | 2H+ | -2.25V |

FIG. 1

HYPOCHLORITE FORMULATIONS FOR WOUND HEALING

RELATED APPLICATIONS

This application claims the benefit of priority to U.S. Provisional Patent Application No. 62/280,613, filed Jan. 19, 2016, the disclosure of which is incorporated by reference herein in its entirety.

FIELD OF THE DISCLOSURE

The present disclosure relates generally to wound healing formulations and methods of use. More specifically, the present disclosure is related to wound formulations having hypochlorite, or acids or salts thereof, and methods of healing wounds, including burns, using the formulations described herein.

BACKGROUND

A wound is a break in the continuity of body tissues with or without substance loss. Such a break may be caused by mechanical injuries or may be the result of cell damage. Wounds are classified into various types depending on their causes. Wounds created by external trauma are classed as mechanical wounds, including cutting, laceration, scratch, abrasion, piercing, puncture, penetration, crushing, blunt force trauma, and contusion wounds. Another form of wounds is described as thermal wounds, which are caused by the action of extreme heat or cold. In contrast, chemical wounds are caused by the action of chemicals, in particular by erosion by acids or alkalis. Tissue breaks or damage which arise under the action of actinic radiation, e.g. ultraviolet radiation and/or ionizing radiation, are described as radiation wounds. Wounds may be further characterized by the physiological condition, including necrotizing, infected, and chronic or acute wounds.

Injury triggers an organized complex cascade of cellular and biochemical events that result in wound healing. Wound healing is a complex dynamic process that results in the restoration of anatomic continuity and function. The physiological processes of wound healing allows for the regeneration of the destroyed tissue and for closure of the wound. An ideally healed wound is one that has returned to normal anatomic structure, function, and appearance. Wound healing takes place in particular by regeneration of connective tissue and capillaries for the circulation. This process can extend over a period of up to four weeks or longer depending on the size and depth of the wound.

A relatively commonly occurring complication in wound healing is wound infections triggered by microorganisms, including bacteria, fungi, protozoa, mold, viruses, and yeast, which are attributable in particular to defective wound hygiene or increased occurrence of germs, such as is often the case in circumstances where a wound may occur or where healing takes place. Through contamination with various microorganisms, infections of the wound can occur, during which classical signs of local inflammation arise, such as pain, swelling, reddening, and overheating. In the worst case, however, as a result of phlegmonous, or extensive inflammatory dissemination, a general infection or life-threatening sepsis can occur with high fever and chills. A pervasive problem with such infections, including with hospital germs, is the many antibiotic resistances acquired by the microbial strains over time, as a result of which infections arising can only be treated with extreme difficulty, and in patients with an already weakened immune system. There is a need for compositions and formulations for wound healing that act to accelerate wound healing and that are capable of preventing and inhibiting the growth of harmful microorganisms during the healing process.

SUMMARY

It is therefore an aspect of this disclosure to provide improved formulations for wound healing. It is a related aspect to provide formulations capable of eliciting acceleration of wound healing, promotion of wound closure, and improved wound regression, and sustaining desirable responses in a patient in need thereof. It is another aspect of this disclosure to provide methods for treating, ameliorating, or accelerating wound healing using such formulations.

Some embodiments disclosed herein relate to a wound healing formulation that includes hypochlorite, a buffer, a rheology agent, and a silicone polymer or blend thereof. In some embodiments, the formulation further includes water. In some embodiments, the wound healing formulation further includes an antimicrobial agent, an antibiotic, an anti-inflammatory, or an analgesic. In some embodiments, the hypochlorite is present in an amount of about 0.01% to about 1% w/v. In some embodiments, hypochlorite is present in an amount of about 0.06% w/v. In some embodiments, the buffer is an acetate, an ascorbate, a carbonate, a phosphate, a citrate, or an organic-based buffer. In some embodiments, the buffer is sodium phosphate. In some embodiments, the buffer is hydrochloric acid (HCl). In some embodiments, the buffer acts to lower the pH of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the formulation is in a range from about 6.5 to about 7.8. In some embodiments, the buffer is present in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, or 15% w/v. In some embodiments, the buffer is sodium phosphate and is present in an amount of about 0.2% w/v. In some embodiments, the buffer is HCl and is present in an amount of about 0.08% w/v. In some embodiments, the rheology agent is an agent that modifies the flowability of a formulation. In some embodiments, the rheology agent includes a thickening agent, a viscosity modifier, or a gelling agent. In some embodiments, the rheology agent includes sodium magnesium silicate. In some embodiments, the sodium magnesium silicate is a layered silicate known as Laponite. In some embodiments, the rheology agent is present in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, or 15% w/v. In some embodiments, the rheology agent is present in an amount of about 3.25% w/v. In some embodiments, the silicone polymer or blend thereof includes dimethicone, cyclomethicone, or a blend thereof. In some embodiments, the silicone polymer or blend thereof is present in an amount of about 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 15%, or 20% w/v. In some embodiments, the silicone polymer or blend thereof is present in an amount of about 5.0% w/v.

Some embodiments disclosed herein relate to a wound healing formulation including hypochlorite in an amount of about 0.06% w/v, buffer in an amount of about 0.2% w/v sodium phosphate (or 0.08% w/v HCl), a rheology agent in an amount of about 3.25% w/v, and a silicone polymer or blend thereof in an amount of about 5.0% w/v.

Some embodiments disclosed herein related to a method of treating a wound in a subject afflicted with a wound. In some embodiments, the method includes applying to the wound a wound healing formulation as described herein. In some embodiments, applying the formulation includes topically administering the wound healing formulation to the wound. In some embodiments, the wound healing formulation is an ointment, a cream, a spray, a spritz, a mist, a liquid, a gel, a lotion, or a solution. In some embodiments, the formulation is configured to be applied to a wound dressing material, including a bandage, a wipe, a gauze, a sponge, a mesh, or other absorbent wound dressing material. In some embodiments, the wound is skin damage, a burn, an abrasion, a laceration, an incision, a sore, a puncture wound, a penetration wound, a gunshot wound, or a crushing injury. In some embodiments, the wound healing formulation is applied to the wound at least once daily. In some embodiments, the wound healing formulation is applied to the wound three times a day. In some embodiments, applying the wound healing formulation provides a wound healing rate that is accelerated in comparison to a healing rate of a non-treated wound. In some embodiments, the formulation is applied in an amount effective to accelerate wound healing, promote wound closure, or cause wound regression. In some embodiments, the applying the formulation reduces, attenuates, or prevents bacterial growth or infection in the wound.

Some embodiments disclosed herein relate to a method of making a wound healing formulation as described herein. In some embodiments, the method of making the formulation includes mixing a hypochlorite solution with a silicone polymer or blend thereof to form a wound healing formulation. In some embodiments, the formulation is prepared as a liquid, an ointment, a cream, a spray, a spritz, a mist, a liquid, a gel, a lotion, or a solution. In some embodiments, the method of making the formulation includes configuring the formulation for application to a wound dressing material. In some embodiments, the method includes preparing a wound dressing material having the wound healing formulation applied thereto.

In some embodiments, the disclosed compositions, methods of preparing compositions, and methods of using compositions include methods for preparing a stable topical formulation that include electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; mirroring the target mixture of chemically reduced and oxidized species in the electrolyzed saline solution to the reduced species and reactive oxygen species found in a known biological system; adding a rheology modifier; adding a buffering agent; and adding a silicone oil. In other embodiments, the target mixture of chemically reduced and oxidized molecules includes one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. In other embodiments, mirroring further includes measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. In other embodiments, the stable topical formulation includes sodium chloride at a concentration of about 0.07% to about 0.28%. In other embodiments, the rheology modifier includes a metal silicate. In other embodiments, the buffering agent includes a phosphate buffer. In yet other embodiments, the silicone oil includes dimethicone.

In some embodiments, the disclosed compositions, methods of preparing compositions, and methods of using compositions include methods for preparing a composition including electrolyzing a saline solution having a sodium chloride concentration between about 0.05% and about 0.30% by weight using a voltage between about 0 V and about 30 V across an inert anode and a spaced apart inert cathode thereby generating a target mixture of chemically reduced and oxidized molecules within the saline solution; adding a rheology modifier; and adding a silicone oil. The rheology modifier can include a metal silicate. The metal silicate can include a sodium magnesium fluorosilicate. The silicone oil can include dimethicone. The composition can include a buffering agent. The method can include ensuring a final hypochlorite concentration of about 40 ppm.

In some embodiments, the disclosed compositions, methods of preparing compositions, and methods of using compositions include methods for treating wounds, including burns, including providing a subject; providing a composition including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; and applying the composition to a wound of the subject. Applying the composition can include applying the formulation daily.

In some embodiments, the disclosed compositions, methods of preparing compositions, and methods of using compositions include a formulation including an electrolyzed saline solution including a target mixture of chemically reduced and oxidized molecules prepared by applying a voltage between about 0 V and about 30 V to a saline solution having a sodium chloride concentration between about 0.07% and about 0.28% by weight; a rheology modifier; a silicone oil; and a buffering agent, where the target mixture of chemically reduced and oxidized species in the electrolyzed saline solution mirrors the reduced species and reactive oxygen species found in a known biological system. The target mixture of chemically reduced and oxidized molecules can include one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. Mirroring can include measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. The stable formulation can include sodium chloride at a concentration of about 0.07% to about 0.28%. The rheology modifier includes a metal silicate. The buffering agent can include a phosphate buffer. The silicone oil can include dimethicone.

In some embodiments, the disclosed compositions, methods of preparing compositions, and methods of using compositions include a kit including a composition including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution. In some embodiments, the kit further includes one or more of a cleanser, a toner, and a moisturizer.

BRIEF DESCRIPTION OF THE DRAWINGS

In order to describe the manner in which the above-recited and other advantages and features of the invention can be obtained, a more particular description will be rendered by reference to specific embodiments thereof which are illustrated in the appended drawings. Understanding that these drawings depict only typical embodiments and are not therefore to be considered to be limiting of its scope, the invention will be described and explained with additional specificity and detail through the use of the accompanying drawings in which:

FIG. 1 illustrates an example diagram of the generation of various molecules at the electrodes. The molecules written between the electrodes depict the initial reactants and those on the outside of the electrodes depict the molecules/ions produced at the electrodes and their electrode potentials;

DETAILED DESCRIPTION

Figure 2:
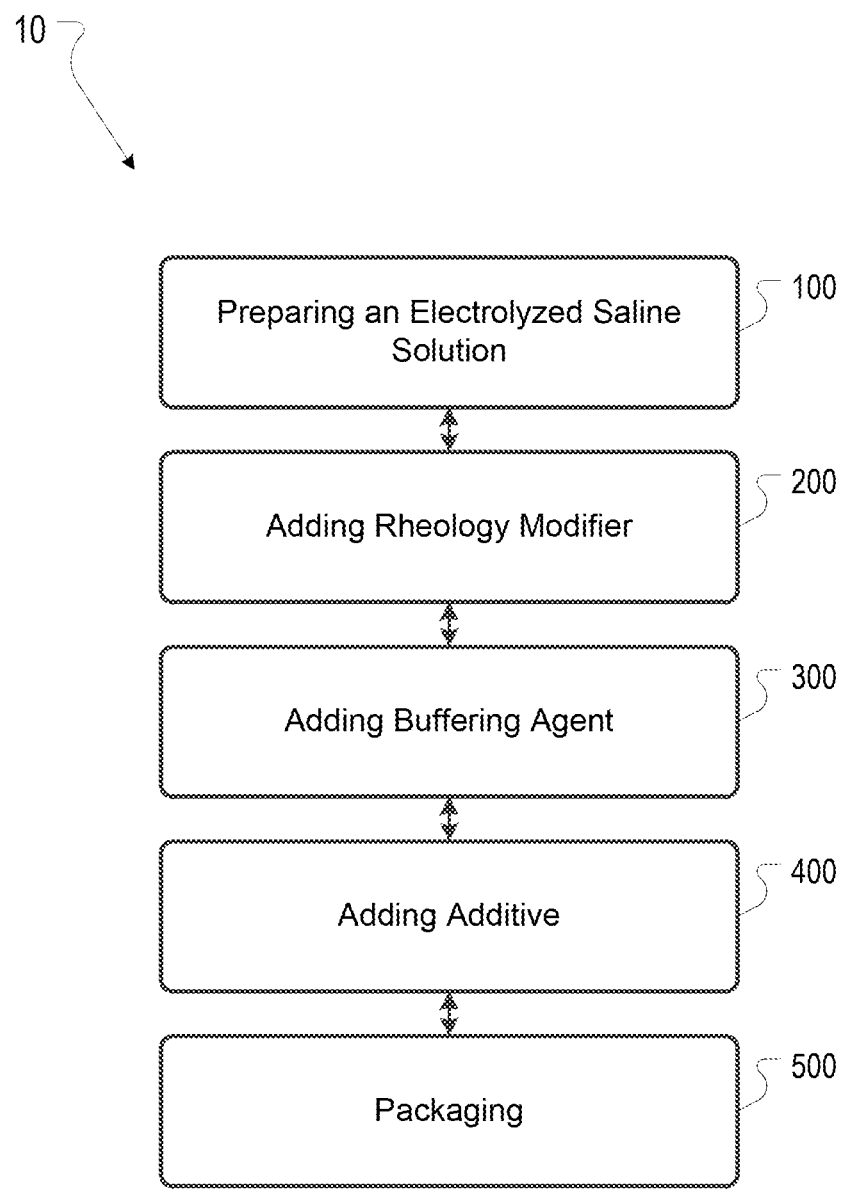
FIG. 2 illustrates a plan view of a process and system for producing a formulation according to the present description.

It will be readily understood that the aspects of the present disclosure, as generally described herein, can be arranged, substituted, combined, separated, and designed in a wide variety of different configurations, all of which are explicitly contemplated herein.

This disclosure pertains to compositions including electrolyzed saline redox-balanced solutions and methods of using these compositions. More particularly, this disclosure pertains to a formulations of electrolyzed saline redox-balanced solution configured to be applied to wounds, burns, or injuries. The electrolyzed saline redox-balanced solution includes a balanced mixture of chemically reduced and oxidized species including an electrolyzed saline solution containing reactive oxygen species (ROS) including one or more of chemically reduced and oxidized species including, but not limited to, hypochlorous acid (HOCl), hypochlorites ($OCl^-$, NaClO), dissolved oxygen ($O_2$), chlorine ($Cl_2$), hydrogen ($H_2$) gas, hydrogen peroxide ($H_2O_2$), hydrogen ions ($H^+$), hypochloride (ClO), superoxides ($*O_2^-$, $HO_2$), ozone ($O_3$), activated hydrogen ions ($H^-$), chloride ions ($Cl^-$), hydroxides ($OH^-$), singlet oxygen ($*O_2$) and other forms of reactive oxygen species (ROS) such as *OCl and *HO$^-$.

Accordingly, described herein are formulations (and/or compositions) containing redox-balanced mixtures of reactive oxygen species (ROS) and reduced species (RS), methods for making formulations which contain redox-balanced mixtures of ROS and RS, and methods of using these formulations which contain redox-balanced mixtures of ROS and RS.

I. Definitions

The definitions provided herein are intended to be read within the full context of the disclosure, and are not intended to be limited to a particular definition. Unless defined otherwise, all technical and scientific terms used herein have the same meaning as is commonly understood by one of ordinary skill in the art. All patents, applications, published applications and other publications referenced herein are expressly incorporated by reference in their entireties unless stated otherwise. In the event that there is a plurality of definitions for a term herein, those in this section prevail unless stated otherwise.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "wound" is understood to mean a break in the continuity of body tissues with or without substance loss, such a break in general being caused by mechanical injuries or physically caused cell damage. A wound can include skin damage, a burn, an abrasion, a laceration, an incision, a sore, a puncture wound, a penetration wound, a gunshot wound, or a crushing injury. A wound may include mechanical wounds, including cutting, laceration, scratch, abrasion, piercing, puncture, penetration, crushing, blunt force trauma, and contusion wounds. A wound may include thermal wounds, which are caused by the action of extreme heat or cold. A wound may include chemical wounds caused by the action of chemicals, in particular by erosion by acids or alkalis. A wound may further include tissue breaks or damage which arise under the action of actinic radiation, e.g. ultraviolet radiation and/or ionizing radiation, are described as radiation wounds. A wound may be necrotizing, infected, chronic, or acute.

As used herein, the term "wound healing" described the phases of a wound from injury to healing. In the first phase, also described as latency or inflammatory phase, within the first hours after wounding has occurred, exudation of body fluids takes place, in particular of blood, to free the wound opening from foreign bodies, germs and dead tissue. Next, a scab, which protects the wound externally from the penetration of germs and foreign bodies, is formed through clotting of the blood that has emerged. After the formation of the scab, the resorption phase of the latency phase begins, in which a catabolic autolysis also takes place, which includes macrophage migration into the wound tissue and phagocytosis of coagulated blood in the wound opening. Foreign bodies or microorganisms which may have penetrated are degraded in this phase, which can be associated with mild to moderate inflammatory symptoms. Further, in the resorption phase the build-up of the basal epithelium and of granulation tissue begins. After about one to three days after causation of the wound, the latency phase is generally completed and the latency phase passes into the second phase, a proliferation or granulation phase, which in general lasts from the fourth to the seventh day after the injury. During this phase, anabolic repair begins. This repair includes the formation of collagen by fibroblasts. In the final phase, the repair or epithelization phase, which begins from about the eighth day after the occurrence of the wound, final scar tissue is formed and the squamous epithelium of the skin is renewed. The scar tissue formed has neither sebaceous nor sweat glands and appears white to mother-of-pearl on the skin. In contrast to undamaged tissue, the collagen in the scar tissue is no longer complexly linked, but is instead aligned parallel.

Further information on the term "wound healing" can be found in Pschyrembel—Clinical Dictionary, 257$^{th}$ edition, 1994, Verlag de Gruyter, Berlin/New York, which is expressly incorporated by reference herein in its entirety.

Impaired wound healing is a major complication underlying several disease processes (such as diabetes). Efficient wound healing is hampered by a wide variety of processes including hypoxia (oxygen deprivation), inflammation, infection, and oxidative stress through the generation of harmful reactive oxygen species (ROS). The inherent complexity of wound healing has resulted in limited efficacy of most therapies that target single parameters involved in the slow healing processes.

Wound healing strays from its normal process as a result of microbial infections. A variety of microbes can infect a wound, complicating the normal healing process. Many wound infections are caused by microbes such as *Proteus mirabilis, Pseudomonas aeruginosa, Staphylococcus epidermidis, Staphylococcus aureus*, and *Escherichia coli*. Although antibiotics have been developed to mitigate microbial infections, a variety of strains have developed resistance. For example, numerous strains of *Staphylococcus aureus* have developed resistance to beta-lactam antibiotics, such as methicillin and oxacillin, and various other antibiotic classes such as glycopeptide antibiotics, sulfonamides, quinolones, or tetracyclines. In some embodiments, the wound healing formulations described herein have antimicrobial properties, capable of removing microorganisms from a wound, inhibiting the growth of microorganisms in a wound, preventing the growth of microorganisms in a wound, or killing microorganisms that may be present in a wound.

As used herein, the term "microorganism" includes bacteria, viruses, yeasts, fungi, molds, and protozoa. In some embodiments, microorganisms include superbugs, which are microorganisms that have developed a tolerance for or resistance to disinfecting agents, and are therefore not affected by anti-microbial treatments. In some embodiments, wound healing compositions described herein are effective at inhibiting or preventing the growth of microorganisms on a surface, including preventing or inhibition the growth of superbugs. In some embodiments, administration of a wound healing composition will kill one or more microorganisms or superbugs. In some embodiments, superbugs include, for example, *Staphylococcus aureus* (including methicillin-resistant *S. aureus* (MRSA) and vancomycin-resistant *S. aureus* (VRSA)), extended spectrum beta-lactamase (ESBL), *Pseudomonas aeruginosa, Clostridium difficile, Salmonella, Mycobacterium tuberculosis, Escherichia coli* (including Carbapenem resistant *E. coli*), multi-drug-resistant *Acinetobacter baumannii* (MRAB), vancomycin-resistant *Enterococcus* (VRE), Carbapenem resistant *Klebsiella pneumoniae*, HIV, hepatitis, and influenza.

In some embodiments, the "purity" of any given agent (for example, dimethicone or hypochlorous acid) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

As used herein, the terms "function" and "functional" and the like refer to a biological, chemical, mechanical, or therapeutic function.

As used herein, the term "wound healing formulation" refers to a composition or formulation that is capable of healing a wound. A wound healing formulation has antimicrobial properties, capable of removing microorganisms from a wound, and capable of preventing growth and proliferation of microorganisms on a surface. In some embodiments, the wound healing formulation is capable of accelerating wound healing. In some embodiments, the wound healing formulation is configured as an ointment, a cream, a spray, a spritz, a mist, a liquid, a gel, a lotion, or a solution. In some embodiments, the formulation is configured to be applied to a wound dressing material, including a bandage, a wipe, a gauze, a sponge, a mesh, or other absorbent wound dressing material. As described herein, a formulation may be a topical formulation, prepared for topical application.

As used herein, a "formulation" refers to a composition including the compounds described and provided herein. In some embodiments, the formulations include balanced mixtures of reactive oxygen species (ROS) and reduced species (RS), and include a suitable topical formulation. In other embodiments, the topical formulations include any suitable formulation configured for topical application to a subject. In yet other embodiments, the topical formulations include any suitable formulation configured for topical application to a wound in the subject. For example, the topical formulations can include one or more of a liquid or a solid. In some cases the topical formulation can include a liquid, a spray, a spritz, a mist, a liquid configured to be applied via a wipe, or any other suitable liquid formulation. In other cases the topical formulation can include any suitable gel formulation. For example, in some embodiments, gel formulations include hydrogels, creams, ointments, emollients, balms, liniments, unguents, colloids, emulsions, dispersions, sols, sol-gels, salves, or the like, or combinations thereof.

The term "antimicrobial" refers to any substance or compound that when contacted with a living cell, organism, virus, or other entity capable of replication, results in a reduction of growth, viability, or pathogenicity of that entity. As used herein, the term "antibiotic" refers to a molecule that inhibits bacterial growth or pathogenesis.

As used herein, "anti-inflammatory" refers to a compound demonstrating activity for reducing inflammation or swelling, or is used to treat patients suffering from inflammatory diseases. Examples of the currently available anti-inflammatory agents include, but not limited to, 1) non-steroidal anti-inflammatory drugs (NSAIDs), such as indomethacin and ibuprofen, 2) corticosteroids, and 3) colchicine. In addition, certain foods exhibit anti-inflammatory effects, As used herein, "analgesic" refers to an agent that lessens, alleviates, reduces, relieves, or extinguishes pain in an area of a subject's body (i.e., an analgesic has the ability to reduce or eliminate pain and/or the perception of pain without a loss of consciousness). Analgesics include opioid analgesics (e.g., codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine) and non-opiate analgesics (e.g., NSAIDs such as salicylates (e.g., aspirin, methyl salicylate, and diflunisal); arylalkanoic acids (e.g., indomethacin, sulindac, diclofenac, and tolmetin); N-arylanthranilic acids (e.g., fenamic acids, mefenamic acid, and mecflofenamate); oxicams (e.g., piroxicam and meloxicam); coxibs (e.g., celecoxib, rofecoxib, valdecoxib, parecoxib, and etoricoxib); sulphonanilides (e.g., nimesulide); naphthylalkanones (e.g., nabumetone); anthranilic acids (e.g., pyrazolidinediones and phenylbutazone); proprionic acids (e.g., fenoprofen, flurbiprofen, ibuprofen, ketoprofen, naproxen, and oxaprozin); pyranocarboxylic acids (e.g., etodolac); pyrrolizine carboxylic acids (e.g., ketorolac); and carboxylic acids.

As used, the term "anesthetic" refers to an agent that produces a reversible loss of sensation in an area of a subject's body. An agent may act as both an analgesic and an anesthetic. Anesthetics include, without limitation, benzocaine, benzyl alcohol, bupivacaine, butamben picrate, chlorprocaine, cocaine, dibucaine, dimethisoquin, dyclonine, etidocaine, hexylcaine, ketamine, lidocaine, mepivacaine, phenol, pramoxine, procaine, tetracaine, salicylates, ropivacaine, prilocaine, and xylocaine.

In some embodiments, the formulations include at least one reactive oxygen species (ROS). ROS can include, but are not limited to superoxides ($O_2^{*-}$, $HO_2^*$), hypochlorites (OCl⁻, HOCl, NaClO), hypochlorates ($HClO_2$, $ClO_2$, $HClO_3$, $HClO_4$), oxygen derivatives ($O_2$, $O_3$, $O_4^{*-}$), hydrogen derivatives (H2, H⁻), hydrogen peroxide ($H_2O_2$), hydroxyl free radical ($OH^{*-}$), ionic compounds (Na⁺, Cl⁻, H⁺, OH⁻, NaCl, HCl, NaOH), chlorine ($Cl_2$), water clusters (n*$H_2O$-induced dipolar layers around ions), and combinations thereof. Some ROS can be electron acceptors and some can be electron donors.

In some embodiments, the formulations disclosed herein are used in the personal care or cosmetics industry and/or as cosmeceuticals. In other embodiments, these topical formulations are applied topically to the skin of a subject to treat a wound. In some embodiments, the formulations are configured to accelerate wound healing and wound regression.

In some embodiments, the wound healing formulation is applied to a wound. In some embodiments, the wound is skin damage, a burn, an abrasion, a laceration, an incision, a sore, a puncture wound, a penetration wound, a gunshot wound, or a crushing injury. In some embodiments, the wound healing formulation is applied to the wound at least once daily. In some embodiments, the wound healing formulation is applied to the wound three times a day. In some embodiments, applying the wound healing formulation provides a wound healing rate that is accelerated in comparison to a healing rate of a non-treated wound. In some embodiments, the formulation is applied in an amount effective to accelerate wound healing, promote wound closure, or cause wound regression. In some embodiments, the applying the formulation reduces, attenuates, or prevents bacterial growth or infection in the wound.

"Hypochlorous acid", as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). As described herein, hypochlorous acid and hypochlorite are used as killing agents, skin cleansing agents, disinfectants, antibacterial agents, sanitizers, and/or preservatives, and are used for accelerating wound healing and closure. Hypochlorite, or acids and salts thereof, may be used in the wound healing compositions of the present disclosure at an amount of about 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 25% w/v. In some embodiments, a 12.5% solution of hypochlorite is added to a wound composition in an amount of about 0.01% to about 1% w/v. In some embodiments, a 12.5% solution of hypochlorite is added to a wound composition in an amount of about 0.06% w/v. In some embodiments, the hypochlorite salt or hypochlorous acid is added directly to a wound healing composition. In some embodiments, the final amount of hypochlorite is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorite in the wound healing composition is between about 10 to about 300 ppm. In some embodiments, the amount of hypochlorite in the wound healing composition is about 75 ppm.

In some embodiments, the hypochlorite is added to the wound healing composition as a hypochlorite solution. In some embodiments, the hypochlorite solution is prepared from hypochlorite salt or hypochlorous acid. In some embodiments, the solution of hypochlorite is prepared by passing a sodium chloride solution through electrolysis. In some embodiments, the sodium chloride solution is a 0.1%, 0.15%, 0.2%, 0.25%, 0.3%, 0.35%, 0.4% or greater w/v % or within a range defined by any two of the aforementioned amounts. In some embodiments, the sodium chloride is 0.28%, and the resulting hypochlorite solution is 300 ppm. In some embodiments, the hypochlorite solution is added to the wound healing composition in an amount of about 0.5%, 1%, 5%, 10%, 15%, 20%, 25%, 30%, 40%, 50% or greater w/v %, or within a range defined by any two of the aforementioned amounts. In some embodiments, the solution includes, for example, about 300 ppm hypochlorite is added to a wound healing composition in an amount of about 25% w/v.

As used herein, silicone polymers include dimethicone, which is also known as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers also include cyclomethicone, which is a cyclic siloxane. Silicone polymers can include polydimethylsiloxane or dimethicone. In some embodiments, the silicon polymers can include dimethicone with a tradename of DIMETHICONE SATIN™. In other instances the dimethicone can have a formula of $C_6H_{18}OSi_2$. In some embodiments, the silicone polymers can include one or more cyclosiloxanes. In some embodiments, the silicone polymers can include any suitable organosilicon compound, silicone-based organic polymer, silicone oil, and/or polymerized siloxane. The formulations described herein include blends of silicone polymers, including blends of dimethicone and cyclomethicone. The silicone polymer or blend of silicone polymers may be used in the wound healing composition in an amount of about 0.5%, 1%, 1.5%, 2%, 2.5%, 3%, 3.5%, 4%, 4.5%, 5%, 10%, or 15%, or greater w/v %, or in an amount within any two of the aforementioned values or between a range defined by these values. In some embodiments, the amount of silicone polymer or a blend of silicone polymers is about 5% w/v. The blend of silicone polymers may include a ratio of dimethicone to cyclomethicone in an amount of about 1:5, 1:4, 1:3, 1:2, 1:1, 2:1, 3:1, 4:1, or 5:1, or within an amount defined by any two of the aforementioned ratios. In some embodiments, the ratio of dimethicone to cyclomethicone is about 1:1.

In some embodiments, silicone polymers may improve the look and/or feel of the formulation. For example, the silicone polymers can be included in the formulation to impart a certain texture such as a silky, slippery, and/or satiny feel to the formulation.

In some embodiments, the formulations provided herein include any suitable rheology modifier. For example, rheology modifiers can include Newtonian fluids and/or soft solids that respond with plastic flow rather than by deforming elastically in response to an applied force. In other embodiments, rheology modifiers are selected and used in the formulations based on the desired characteristics of the rheology modifier and on the compatibility of the rheology modifier with redox signaling molecular compositions. In yet other embodiments, rheology modifiers include thickening agents, viscosity modifiers and/or gelling agents (e.g., acrylic acid-based polymers, cellulosic thickeners, metal silicates, and any other suitable rheology modifiers). In some embodiments, the formulations include one or more acrylic acid-based polymers (e.g., high molecular weight, cross-linked, acrylic acid-based polymers, such as poly(acrylic acid), PAA, carbomer, or polymers having the general structure of $(C_3H4O_2)_n$). In other embodiments, the acrylic acid-based polymers are cross-linked with suitable copolymers (e.g., allyl sucrose, allylpentaerythritol, or any other suitable copolymer). In yet other embodiments, suitable copolymers of acrylic acid can be modified by long chain ($C_{10}$-$C_{30}$) alkyl acrylates and can be cross-linked with copolymer (e.g., allylpentaerythritol). In some embodiments, acrylic acid polymers are converted to a salt to reach a desired viscosity. In some embodiments, rheology modifiers include any polymeric co-thickener (e.g., carboxymethyl cellulose, cellulose ethers, xanthan, guar, natural gums, polyurethanes, ASE and HASE polyacrylic acid polymers.

In some embodiments, rheology modifiers include any suitable natural clay. For example, rheology modifiers can include natural clays such as bentonite or other similar clays. In other instances, rheology modifiers can include hectorite.

In some embodiments, rheology modifiers include any suitable synthetic silicate clay. In other embodiments, synthetic silicate clay includes magnesium and sodium silicate. In other embodiments, rheology modifiers include any suitable metal silicate gelling agent. In yet other embodiments, the metal silicate gelling agent includes one or metal silicates including an alkali metal, an alkaline earth metal, or any combinations thereof. In some embodiments, suitable alkali metals or alkaline earth metals can include, but are not limited to, lithium, sodium, potassium, magnesium, calcium, and the like. In some embodiments, the metal silicate gelling agent can be a sodium magnesium silicate or a derivative thereof. In other embodiments, the metal silicate gelling agent can include sodium magnesium fluorosilicate. For example, the metal silicate sold under the tradename LAPONITE™ can be used as a rheology modifier. In some cases, the metal silicate sold under the tradename LAPONITE XL21™ can be used as a rheology modifier.

In some embodiments, the rheology modifier includes one or more colloidal layered silicates. In other embodiments, the rheology modifier includes one or more of lithium magnesium sodium silicate, lithium magnesium sodium silicate and tetrasodium pyrophosphate, and/or sodium magnesium fluorosilicate and tetrasodium pyrophosphate. In yet other embodiments, the rheology modifier includes one or more of a colloid, a gel, a temporary sol, and/or a permanent sol. In some embodiments, the rheology modifier includes a personal care grade colloidal layered silicate. In other embodiments, the rheology modifier includes one or more colloidal layered silicates sold under the tradenames LAPONITE RD™, LAPONITE RDS™, LAPONITE S482™, LAPONITE SL25™, LAPONITE EP™, LAPONITE JS™, LAPONITE XLG™, LAPONITE XLS™, LAPONITE XL21™, and LAPONITE D™.

As used herein, the term "sodium magnesium silicate" refers to a silicate of sodium and magnesium and is a synthetic silicate clay, having magnesium and sodium silicate. It is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite. As used herein, sodium magnesium silicate is useful as a gelling agent or rheology modifier. Thus, sodium magnesium silicate as used herein may have properties similar to an emulsifier. In some embodiments, the sodium magnesium silicate used herein may be considered an emulsifier. Sodium magnesium silicate may be used in the wound healing composition in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of sodium magnesium silicate is about 3.25% w/v.

In some embodiments, the rheology modifiers can be present in the formulation in any suitable amount. In other embodiments, the formulation includes about 0.1% by weight to about 10% by weight of the rheology modifier. In yet other embodiments, the amount of rheology modifier can be from about 1.0% to about 5% by weight. In some embodiments, the amount of the rheology modifier can be 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.25%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight. In other embodiments, the amount of modifier is 1% or 2% by weight. In yet other embodiments, these weight percentages can be approximate and can be modified to achieve specific characteristics desired and/or required in the composition.

In some embodiments, the viscosity of the hydrogel formulation can be any suitable viscosity such that the formulation can be topically applied to a subject. In some embodiments, the viscosity of the hydrogel formulation can be in the range of about 1,000 to about 100,000 centipoise (cP). In some embodiments, the viscosity of the hydrogel can be 1,000 cP, 2,000 cP, 3,000 cP, 4,000 cP, 5,000 cP, 10,000 cP, 15,000 cP, 20,000 cP, 25,000 cP, 30,000 cP, 35,000 cP, 40,000 cP, 45,000 cP, 50,000 cP, 55,000 cP, 60,000 cP, 65,000 cP, 70,000 cP, 75,000 cP, 80,000 cP, 85,000 cP, 90,000 cP, or 95,000 cP. In some embodiments, the viscosity of the hydrogel can be in the range of about 1,000 cP to about 20,000 cP. In other embodiments, the viscosity of the hydrogel can be in the range of about 12,000 cP to about 20,000 cP. These viscosity ranges can be approximate and can be modified to achieve specific characteristics desired and/or required in the composition.

In some embodiments, the formulations include any suitable buffering agents. In other embodiments, any suitable buffering agent is employed to yield and maintain the desired pH of the formulation. In yet other embodiments, other buffers suitable for use in the hydrogel formulations described herein include, but are not limited to, salts and acids of acetate, borate, glutamate, citrate, tartrate, benzoate, lactate, histidine or other amino acids, gluconate, phosphate, malate, succinate, formate, propionate, and carbonate. In some embodiments, other buffering agents are used as generally known in the art (see Handbook of Cosmetic and Personal Care Additives, 2nd ed., Ashe et al. eds. (2002) and Handbook of Pharmaceutical Excipients, 4th ed., Rowe et al. eds. (2003)). In some embodiments, suitable buffering agents are either in liquid or solid form. In another embodiment, the buffering agent is an acid or salt of a phosphate compound. In some embodiments, the buffering agent is sodium phosphate. The sodium phosphate employed herein can be any suitable form of sodium phosphate including, for example, monobasic sodium phosphate, dibasic sodium phosphate, tetrasodium pyrophosphate, or combinations thereof. Likewise, suitable buffering agents can include any suitable form of potassium phosphate including, but not limited to, monobasic potassium phosphate, dibasic potassium phosphate, tetrapotassium pyrophosphate, or combinations thereof. In some embodiments, suitable buffering agents include one or more of citric acid, lactic acid, sodium dihydrogen phosphate, ammonia solution, sodium hydroxide, sodium silicate, primary amines, secondary amines, DMEA, AMP95, and DMAMP80.

In some embodiments, any suitable amount of buffering agent may be included in the formulation. In some embodiments, the amount of buffering agent present in the hydrogel formulations is from about 0.01 weight-percent to about 5.0 weight-percent, based on the weight of the formulation. In some embodiments, the buffering agent can be present in an amount of from about 0.1 weight-percent to about 1.0 weight-percent. In other embodiments, the amount of buffering agent present in the hydrogel formulations is 0.01%, 0.08%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.25%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight of the formulation.

As used herein, the term "sodium phosphate monobasic" refers to the chemical formula of $NaH_2PO_4$, an inorganic compound of sodium with dihydrogen phosphate. Sodium phosphate monobasic is also referred to as sodium dihydrogen phosphate, sodium phosphate, monosodium phosphate, sodium biphosphate, acid sodium phosphate, monosodium orthophosphate, or primary sodium phosphate. As described herein, sodium phosphate may be used for adjustment of pH, as a thickening agent, or as a buffer. Sodium phosphate monobasic may be used in the wound healing composition in an amount of about 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of sodium phosphate is about 0.2% w/v.

As used herein, the term "hydrochloric acid" refers to a chloric acid HCl. Hydrochloric acid may be added to the wound healing composition to lower the pH. In some embodiments, HCl is added as a final step to decrease the pH. In some embodiments, HCl is used as a buffer. In some embodiments, HCl introduces ions, which causes the wound healing composition to thicken as a result of excess ions. Thus, HCl is used in some embodiments as a thickener. Accordingly, in some embodiments is provided a wound healing composition including hypochlorous acid, sodium phosphate, sodium magnesium silicate, dimethicone, and hydrochloric acid. Hydrochloric acid may be used in the wound healing composition in an amount of about 0.01%, 0.02%, 0.03%, 0.04%, 0.05%, 0.08% 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of HCl is about 0.08%. In some embodiments, HCl is present instead of sodium phosphate.

As used herein, the pH of the formulation is the numerical scale to specify the acidity or basicity of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the formulation is in a range from about 6.5 to about 7.8.

The wound healing composition described herein may further include an additive known in the art. Exemplary additives include emulsifiers, detergents, emollients, moisturizers, humectants, pigments, dyes, pearlescent compounds, nacreous pigments, bismuth oxychloride coated mica, titanium dioxide coated mica, colorants, fragrances, biocides, preservatives, alpha hydroxy acids, antioxidants, anti-microbial agents, anti-fungal agents, antiperspirant agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays and combinations thereof.

In some embodiments, the formulation is substantially free of organic matter. In other embodiments, substantially no organic material is present in the formulations as described. In yet other embodiments, organic material refers to organic compounds derived from the remains of organisms such as plants and animals and their waste products. In some embodiments, organic material refers to compounds such as proteins, lipids, nucleic acids, and carbohydrates. In yet other embodiments, substantially free of organic matter means less than about 0.1 ppt, less than about 0.01 ppt, less than about 0.001 ppt or less than about 0.0001 ppt of total organic material in the formulation.

In some embodiments, the formulations include any suitable salt. In other embodiments, the formulation includes one or more suitable salts. In some embodiments, the formulation includes sodium chloride. In other embodiments, the formulation includes one or more of lithium chloride, sodium chloride, potassium chloride, rubidium chloride, cesium chloride, magnesium chloride, calcium chloride, strontium chloride, copper chloride, copper sulfate, and iron chloride. In yet other embodiments, the salt includes one or more of a chloride salt, a phosphate salt, a nitrate salt, an acetate salt, a lithium salt, a sodium salt, a potassium salt, a magnesium salt, a calcium salt, and an iron salt.

In some embodiments, the salt includes one or more additives. Salt additives can include, but are not limited to, potassium iodide, sodium iodide, sodium iodate, dextrose, glucose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, lactate, phosphates, tris, borates, carbonates, citrates, and folic acid. In some embodiments, one or more additives are added at the salting step. In other embodiments, one or more additives are added at any point in the preparation of the electrolyzed saline solution. In yet other embodiments, one or more additives are added just prior to bottling.

In some embodiments, the prepared saline is generally free from contaminants, both organic and inorganic, and homogeneous down to the molecular level. In particular, because some metal ions can interfere with electro-catalytic surface reactions, it may be helpful for some metal ions to be removed and/or absent from the saline solution.

In another embodiment, the saline solution includes any suitable ionic soluble salt mixture (e.g., saline containing chlorides). In addition to NaCl, other non-limiting examples include LiCl, HCl, $CuCl_2$, $CuSO_4$, KCl, $MgCl_2$, $CaCl_2$, sulfates and phosphates. In some instances, strong acids such as sulfuric acid ($H_2SO_4$) and strong bases such as potassium hydroxide (KOH) and sodium hydroxide (NaOH) can be used as electrolytes due to their strong conducting abilities.

In some embodiments, the formulations include salt in any suitable concentrations. For example, the saline concentration in the formulation can be about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v. In other embodiments, the formulation includes about 0.28% salt.

In some embodiments, the wound healing composition described herein is characterized in having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the wound healing composition is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg.

In some embodiments is provided a method of making the wound healing composition formulation. In some embodiments, the method includes providing hypochlorite. In some embodiments, the hypochlorite is provided as a hypochlorite acid or salt. In some embodiments, the hypochlorite is provided as a hypochlorite solution. In some embodiments, the method of making the wound healing composition includes providing hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm. In some embodiments, a 12.5% solution of hypochlorite is provided in an amount of about 0.01% to about 1% w/v. In some embodiments, a 12.5% solution of hypochlorite is provided in an amount of about 0.06% w/v.

In some embodiments, the method of making the wound healing composition includes providing a hypochlorite solution. In some embodiments, the hypochlorite solution is prepared from hypochlorite acids or salts. In some embodiments, the hypochlorite salt is sodium hypochlorite. In some embodiments, the hypochlorite solution is prepared from sodium chloride. In some embodiments, the method includes running sodium chloride solution through electrolysis. In some embodiments, the sodium chloride solution is provided in an amount of about 0.1%, 0.15%, 0.2%, 0.25%, 0.3%, 0.35%, or 0.4% w/v. In some embodiments, the sodium chloride is 0.28%, and the resulting hypochlorite solution is about 300 ppm. In some embodiments, the method of making the wound healing composition includes diluting the hypochlorite solution to provide hypochlorite in an amount of about 10, 15, 20, 25, 30, 35, 40, 45, 50, 55, 60, 65, 70, 75, 80, 85, 90, 95, 100, 120, 150, 175, 200, 250, or 300 ppm or within a range defined by any two of the aforementioned amounts. In some embodiments, hypochlorite is provided in an amount of about 50 to 100 ppm. In some embodiments, the hypochlorite is provided in an amount of about 75 ppm. In some embodiments, a 12.5% solution of hypochlorite is provided in an amount of about 0.01% to about 1% w/v. In some embodiments, a 12.5% solution of hypochlorite is provided in an amount of about 0.06% w/v.

In some embodiments, methods for making formulations which contain redox-balanced mixtures of ROS and RS include generating redox-balanced mixtures of ROS and RS which are similar to redox-balanced mixtures of ROS and RS that exist naturally inside healthy living cells and/or biological systems. The redox-balanced mixtures of ROS and RS can include signaling molecules that are the same as those that are naturally produced inside of living cells and/or biological systems. In other embodiments, methods for making formulations which contain redox-balanced mixtures of ROS and RS include first determining a balanced target mixture of redox-signaling molecules inherent to healthy cells and measuring the concentrations of the ROS and RS contained therein, usually with fluorescent indicators. This balanced target mixture can be representative of a known biological system. This balanced target mixture can then be replicated in the formulation by electrolyzing a saline solution while varying any suitable electrolysis parameter (e.g., temperature, flow, pH, power-source modulation, salt makeup, salt homogeneity, and salt concentration). The resulting electrolyzed saline solution (ESS) may then include the replicated, mimicked, and/or mirrored balanced target mixture. In other embodiments, the formulation can be verified to have a similar makeup as the balanced target mixture by measuring concentrations of the reactive molecules (e.g., ROS and RS) contained within the formulation. In some cases, the concentrations of the reactive molecules contained within the formulation can be measured by any suitable analytical methods. In other cases, the concentrations of ROS and RS contained within the formulation can be measured by fluorescent indicators (e.g., R-Phycoerythrin (R-PE), Aminophenyl Fluorescein (APF) and Hydroxyphenyl Fluorescein (HPF)).

In some embodiments, the known biological system includes one or more of the cells and/or tissue of the skin. For example, the cells and/or tissue that include the skin can include one or more of an epidermis, a dermis, an epithelium, keratinocytes, Merkel cells, melanocytes, Langerhans cells, stratum corneum, stratum lucidum, stratum granulosum, stratum spinosum, stratum germinativum, basement membrane, and any other related cells or tissue.

In some embodiments, one or more of the fluorescent indicators, R-Phycoerythrin (RPE), Aminophenyl fluorescein (APF), and Hydroxyphenyl fluorescein (HPF) are used to measure concentrations of ROS and RS in the formulation. These fluorescent indicator molecules exhibit a change in fluorescence when they come into contact with specific redox species. These corresponding changes in fluorescence can then be measured using a fluorospectrometer to verify and quantify the existence and relative concentration of the corresponding redox species. A combination of measurements from these indicators can be utilized to measure the concentration of ROS and RS in the formulation. These ROS and RS measurements of the formulation can then be compared to ROS and RS measurements taken from the balanced target mixture. This comparison can then be used to vary any suitable electrolysis parameter (e.g., temperature, flow, pH, power-source modulation, salt makeup, salt homogeneity, and salt concentration) such that the ROS and RS measurements of the formulation approximate the ROS and RS measurements of the balanced target mixture. Any other suitable analytical technique can also be used to determine ROS and RS measurements of the formulation and/or ROS and RS measurements of the balanced target mixture to make a similar comparison and/or to vary any suitable electrolysis parameter (e.g., temperature, flow, pH, power-source modulation, salt makeup, salt homogeneity, and salt concentration) such that the ROS and RS measurements of the formulation approximate the ROS and RS measurements of the balanced target mixture.

In some embodiments, reactive oxygen species (ROS) and reduced species (RS) are generated by electrolysis of saline solutions. Electrolysis of saline solutions can be carried out by preparing a saline solution, inserting an inert anode and a spaced apart inert cathode into the saline solution, and applying a current across the electrodes. Some forms of electrolysis (e.g., electrolysis that utilizes a pulsing voltage potential) can generate and preserve a variety of ROS and RS molecules. These forms of electrolysis can facilitate generation of several generations of ROS molecules, including stabilized superoxides such as $O2^{*-}$. In some embodiments, these types of electrolysis generate 1st, 2nd, and 3rd generations of ROS molecules.

FIG. 1 illustrates some embodiments of 1st, 2nd, and 3rd generations of ROS molecules. FIG. 1 illustrates a diagram of the generation of various ROS molecules at the inert anode and the inert cathode, respectively. The molecules depicted in the space between the electrodes depict some of the initial reactant molecules. The molecules depicted to the left of the anode and to the right of the cathode depict the ROS molecules produced at the respective electrodes and their electrode potentials. The diagram divides the generated ROS molecules into their respective generation (e.g., 1st, 2nd, and 3rd generation). The ROS molecules produced in a particular generation utilize the ROS molecules produced in a previous generation as the initial reactant molecules. For example, the 2nd generation ROS molecules utilize the 1st generation ROS molecules as the initial reactant molecules. Although FIG. 1 only depicts three generations of ROS molecules, additional generations of ROS molecules can also be generated.

In some embodiments, the compositions and/or topical formulations disclosed herein include any suitable ROS molecules generated by electrolysis of saline solutions. In other embodiments, the compositions and/or topical formulations include any suitable chemical entities generated by electrolysis of saline solutions. In yet other embodiments, the formulations include, but are not limited to, one or more of the ROS molecules and/or chemical entities depicted in FIG. 1.

In some embodiments, the formulations include one or more of superoxides ($O_2^{*-}$, $HO_2^*$), hypochlorites ($OCl^-$, HOCl, NaClO), hypochlorates ($HClO_2$, $ClO_2$, $HClO_3$, $HClO_4$), oxygen derivatives ($O_2$, $O_3$, $O_4^{*-}$), hydrogen derivatives (H2, $H^-$), hydrogen peroxide ($H_2O_2$), hydroxyl free radical ($OH^{*-}$), ionic compounds ($Na^+$, $Cl^-$, $H^+$, $OH^-$, NaCl, HCl, NaOH), chlorine ($Cl_2$), water clusters ($n^*H_2O$-induced dipolar layers around ions), and any other variations. In other embodiments, the composition includes at least one species such as $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $OH^-$, $O_3$, $O_4^*$, $OH^{*-}$, $HOCl-O_2^{*-}$, $HOCl-O_3$, $O_2^*$, $HO_2^*$, NaCl, HCl, NaOH, water clusters, or a combination thereof.

In some embodiments, the formulations include at least one species such as $H_2$, $Cl_2$, $OCl^-$, HOCl, NaOCl, $HClO_2$, $ClO_2$, $HClO_3$, $HClO_4$, $H_2O_2$, $O_3$, $O_4^*$, $OH^{*-}$, $HOC-O_2^{*-}$, $HOCl-O_3$, $O_2^{*-}$, $HO_2^*$, water clusters, or a combination thereof. In some embodiments, the formulations include at least one species such as $HClO_3$, $HClO_4$, $H_2O_2$, $O_3$, $O_4^*$, $OH^{*-}$, $HOC-O_2^{*-}$, $HOCl-O_3$, $O_2^{*-}$, $HO_2^*$, water clusters, or a combination thereof. In some embodiments, the formulations include at least $O_2^{*-}$ and one HOCl.

In some embodiments, the formulations include $O_2$. In some embodiments, the formulations include $H_2$. In some embodiments, the composition can include $Cl^-$. In some embodiments, the composition can include $OCl^-$. In some embodiments, the composition can include HOCl. In some embodiments, the composition can include NaOCl. In one embodiment, the composition can include $HClO_2$. In some embodiments, the composition can include $ClO_2$. In some embodiments, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^*$. In one embodiment, the composition can include $OH^-$. In one embodiment, the composition can include $O_3$. In one embodiment, the composition can include $O_4^*$. In one embodiment, the composition can include $^1O_2$. In one embodiment, the composition can include $OH^{*-}$. In one embodiment, the composition can include $HOCl-O_2^{*-}$. In one embodiment, the composition can include $HOCl-O_3$. In one embodiment, the composition can include $O_2^{*-}$. In one embodiment, the composition can include $HO_2^*$. In one embodiment, the composition can include NaCl. In one embodiment, the composition can include HCl. In one embodiment, the composition can include NaOH. In one embodiment, the composition can include water clusters. Embodiments can include combinations thereof.

In some embodiments, the formulation can include stable complexes of ROS molecules. In some instances, superoxides and/or ozones can form stable Van der Waals molecular complexes with hypochlorites. In other instances, clustering of polarized water clusters around charged ions can also have the effect of preserving hypochlorite-superoxide and hypochlorite-ozone complexes. In some cases, these types of complexes can be built through electrolysis on the molecular level on catalytic substrates and may not occur spontaneously by mixing together the individual components. In other cases, hypochlorites can be produced spontaneously by the reaction of dissolved chlorine gas ($Cl^-$) and water. As such, in a neutral electrolyzed saline solution, one or more of these stable molecules and complexes may be generated: dissolved gases (e.g., $O_2$, $H_2$, $Cl^-$); hypochlorites (e.g., $OCl^-$, HOCl, NaOCl); hypochlorates (e.g., $HClO_2$, $ClO_2$, $HClO_3$, $HClO_4$); hydrogen peroxide (e.g., $H_2O_2$); ions (e.g., $Na^+$, $Cl^-$, $H^+$, $H^-$, $OH^-$); ozone (e.g., $O_3$, $O_4^{*-}$); singlet oxygen (e.g., $^1O$); hydroxyl free radical (e.g., $OH^{*-}$); superoxide complexes (e.g., $HOCl-O_2^{*-}$); and ozone complexes (e.g., $HOCl-O_3$). One or more of the above molecules can be found within the compositions and composition described herein.

In some embodiments, the electrolysis of the saline solution is performed under varying parameters. As the parameters are varied, various different molecules at various different concentrations are generated. In some embodiments, the composition includes about 0.1 ppt (part per trillion), about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of $OCl^-$. In some embodiments, $OCl^-$ can be present at 3 ppt. In other embodiments, $OCl^-$ can be present at 1 to 100 ppm (parts per million) or from 10 to 30 ppm or from 16 to 24 ppm. In particular embodiments, $OCl^-$ is present at 16 ppm, 17 ppm, 18 ppm, 19 ppm, 20 ppm, 21 ppm, 22 ppm, 23 ppm, 24 ppm or 25 ppm. In other embodiments, $OCl^-$ can be the predominant chlorine containing species in the composition.

In some embodiments, the chlorine concentration in the compound includes about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

In some embodiments, the chloride species is present in a concentration from about 1400 to about 1650 ppm. In other embodiments, the chloride species can be present from about 1400 to about 1500 ppm or from about 1500 to about 1600 ppm or from about 1600 to about 1650 ppm. In other embodiments, the chloride anion can be present in an amount that is predetermined based on the amount of NaCl added to the initial solution.

In some embodiments, the sodium species is present in the formulation in a concentration from about 1000 to about 1400 ppm. In other embodiments, the sodium species is present in a concentration from about 1100 to about 1200 ppm; from about 1200 to about 1300 ppm or from about 1300 to about 1400 ppm. For example, the sodium species can be present at about 1200 ppm. In other embodiments, the sodium anion can be present in an amount that is predetermined based on the amount of NaCl added to the initial solution.

The composition generally can include electrolytic and/or catalytic products of pure saline that mimic redox signaling molecular compositions of the native salt water compounds found in and around living cells. The formulation can be fine-tuned to mimic or mirror molecular compositions of different biological media. The formulation can have reactive species other than chlorine present. As described, species present in the compositions and compositions described herein can include, but are not limited to $O_2$, $H_2$, $Cl_2$, $OCl^-$, HOCl, NaOCl, $HClO_2$, $ClO_2$, $HClO_3$, $HClO_4$, $H_2O_2$, $Na^+$, $Cl^-$, $H^+$, $OH^-$, $O_3$, $O_4^*$, $OH^{*-}$, $HOCl-O_2^{*-}$, $HOCl-O_3$, $O_2^*$, $HO_2^*$, NaCl, HCl, NaOH $^1O$, and water clusters: $n*H_2O$-induced dipolar layers around ions, and any variations.

In some embodiments, the formulation is substantially stable. In other embodiments, the formulation is substantially stable which means, among other things, that one or more active ingredient(s) (e.g., ROS and/or RS) are present, measurable or detected throughout a shelf life of the formulation. In one embodiment, the ROS include one or more of superoxides and/or hydroxyl radicals. For example, in some embodiments the formulation includes at least some percentage of the ROS and RS that is present in the formulation after a certain number of years, such as at least 95% of the active ingredient(s) present in the formulation after 2 years, at least 90% of the active ingredient(s) present in the formulation after 3 years, at least 85% of the active ingredient(s) present in the formulation after 4 years, at least 80% of the active ingredient(s) present in the formulation after 5 years, at least 75% of the active ingredient(s) present in the formulation after 6 years, at least 70% of the active ingredient(s) present In the formulation after 7 years, at least 65% of the active ingredient(s) present In the formulation after 8 years, at least 60% of the active ingredient(s) present In the formulation after 9 years, at least 55% of the active ingredient(s) present in the formulation after 10 years and the like.

In some embodiments, ROS can include substantially stable oxygen radicals. For example, stable oxygen radicals can remain stable for about 3 months, about 6 months, about 9 months, about 12 months, about 15 months, about 18 months, about 21 months, between about 9 months and about 15 months, between about 12 months and about 18 months, at least about 9 months, at least about 12 months, at least about 15 months, at least about 18 months, about 24 months, about 30 months, about 50 months, about 100 months, about 200 months, about 300 months, about 400 months, about 500 months, about 1000 months, about 2000 months, or longer.

Stable oxygen radicals can be substantially stable. Substantially stable can mean that the stable oxygen radical can remain at a concentration greater than about 75% relative to the concentration on day 1 (day 1 meaning on the day or at the time it was produced), greater than about 80%, greater than about 85%, greater than about 90%, greater than about 95%, greater than about 96%, greater than about 97%, greater than about 98%, or greater than about 99% over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Substantially stable can mean that the stable oxygen radical can remain at a concentration greater than about 75% relative to the concentration on day 1 or the day is was produced, greater than about 80% relative to the concentration on day 1 or the day is was produced, greater than about 85% relative to the concentration on day 1 or the day is was produced, greater than about 90% relative to the concentration on day 1 or the day is was produced, greater than about 95% relative to the concentration on day 1 or the day is was produced, greater than about 96% relative to the concentration on day 1 or the day is was produced, greater than about 97% relative to the concentration on day 1 or the day is was produced, greater than about 98% relative to the concentration on day 1 or the day is was produced, or greater than about 99% relative to the concentration on day 1 or the day is was produced over a given time period as described above. For example, in one embodiment, the stable oxygen radical is at a concentration greater than about 95% relative to day 1 for at least 1 year. In another embodiment, the at least one oxygen radical is at a concentration greater than about 98% for at least 1 year. In other embodiments, the stable oxygen radical is greater than about 86% stable for at least 4 years, greater than about 79% stable for at least 6 years, greater than about 72% stable for at least 8 years, greater than about 65% stable for at least 10 years, or 100% stable for at least 20 years.

In still other embodiments, the stable oxygen radical is greater than about 95% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 96% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the stable oxygen radical is greater than about 97% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 98% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 99% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is 100% stable for at least 2 years, at least 3 years, at least 4 years, at least 5 years, at least 6 years, at least 7 years, at least 8 years, at least 9 years, at least 10 years, at least 15 years, or at least 20 years.

In some embodiments, the stability of the stable oxygen radicals is expressed as a decay rate over time. In other embodiments, substantially stable means a decay rate less than 1% per month, less than 2% per month, less than 3% per month, less than 4% per month, less than 5% per month, less than 6% per month, less than 10% per month, less than 3% per year, less than 4% per year, less than 5% per year, less than 6% per year, less than 7% per year, less than 8% per year, less than 9% per year, less than 10% per year, less than 15% per year, less than 20% per year, less than 25% per year, between less than 3% per month and less than 7% per year.

In some embodiments, stability of the stable oxygen radicals is expressed as a half-life. For example, the half-life of the stable oxygen radical can be about 6 months, about 1 year, about 2 years, about 3 years, about 4 years, about 5 years, about 10 years, about 15 years, about 20 years, about 24 years, about 30 years, about 40 years, about 50 years, greater than about 1 year, greater than about 2 years, greater than about 10 years, greater than about 20 years, greater than about 24 years, between about 1 year and about 30 years, between about 6 years and about 24 years, or between about 12 years and about 30 years.

In some embodiments, the stability of the stable oxygen radicals is expressed as a shelf life. For example, the composition can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

In some embodiments, the method of making the wound healing composition further includes providing a silicone polymer or a blend of silicone polymers. In some embodiments, the silicone polymer is a silicone polymer blend of dimethicone and cyclomethicone in a ratio of about 1:1. In some embodiments, the silicone polymer or blend thereof is provided in an amount of about 0.5%, 1%, 1.5%, 2%, 2.5%, 3%, 3.5%, 4%, 4.5%, 5%, 10%, or 15%, w/v, or within a range defined by any two of the aforementioned amounts. In some embodiments, the silicone polymer or blend thereof is provided in an amount of about 5% w/v.

In some embodiments, the method further includes providing sodium magnesium silicate. In some embodiments, the sodium magnesium silicate is provided in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or within a range defined by any two of the aforementioned amounts. In some embodiments, the sodium magnesium silicate is provided in an amount of about 3.25% w/v.

In some embodiments, the method of making the wound healing composition further includes providing sodium phosphate, HCl, water, or buffer or combinations thereof. In some embodiments, the sodium phosphate is provided in an amount of about 0.05%, 0.1%, 0.2%, 0.3%, 0.4%, 0.5%, 1%, 1.5%, 2%, or 2.5% w/v or within a range defined by any two of the aforementioned amounts. In some embodiments, sodium phosphate is provided in an amount of about 0.2% w/v.

In some embodiments, HCl may be used in the wound healing composition in an amount of about 0.01%, 0.02%, 0.03%, 0.04%, 0.05%, 0.1%, 0.2%, 0.3%, 0.4%, 0.5%, 1%, 1.5%, 2%, 2.5%, 3%, 3.5%, 4%, 4.5%, 5%, 6%, 7%, 10%, 15%, or greater w/v %, or in an amount within any two of the aforementioned values. In some embodiments, the amount of HCl is about 0.08%. In some embodiments, HCl is provided instead of sodium phosphate.

In some embodiments, the water and/or buffer is provided in an amount to make up the balance of the wound healing composition, and is provided in an amount of about 20%, 30%, 40%, 45%, 50%, 55%, 56%, 57%, 58%, 59%, 60%, 61%, 61.55%, 62%, 62.5%, 63%, 65%, 70%, 75%, 80%, or 90% w/v or within a range defined by any two of the aforementioned amounts.

As used herein, the term "buffer" refers to a buffering agent and is used for balancing the pH and/or osmolality of the wound healing composition. Examples of a buffer for use herein include, for example, salts of phosphates (such as sodium phosphate), borates, citrates, malates, formates, lactates, succinates, acetates, ascorbates, carbonates, bicarbonates, organic compound based buffers (including, for example, TRIS, HEPES, MOPS, MES, PIPES, TES, bicine, tricine, TAPSO), sodium ions, potassium ions, chloride ions (such as from HCl), bicarbonate ions, glucose, sucrose, peptides, proteins, a combination or mixture thereof or other agents that are chemically, functionally, or physiologically equivalent or similar. The wound healing composition compositions provided herein have an optimum pH and viscosity, with an osmolality that is hypo-osmotic, having an osmolality by vapor pressure of about 10, 20, 30, 35, 36, 37, 38, 39, 40, 41, 42, 43, 44, 45, 46, 47, 48, 49, 50, 55, 60, 70, 80, 90, or 100 mmol/kg, or within a range defined by any two of the aforementioned amounts. In some embodiments, the osmolality by vapor pressure is about 38 mmol/kg. In some embodiments, the osmolality by vapor pressure is about 49 mmol/kg. In some embodiments, the wound healing composition is characterized in having an osmolality by freezing point depression of about 10, 15, 20, 21, 22, 23, 24, 25, 26, 27, 28, 29, 30, 35, 40, 45, 50, 51, 52, 53, 54, 55, 56, 57, 58, 59, 60, 65, 70, 80, 90, or 100 mOsm/kg, or within a range defined by any two of the aforementioned amounts. In some embodiments, the osmolality by freezing point depression is about 22 mOsm/kg. In some embodiments, the osmolality by freezing point depression is about 54 mOsm/kg. The osmolality of the wound healing composition can be determined by vapor pressure osmometry or freezing point osmometry.

In some embodiments is provided a method of using a wound healing composition. In some embodiments, the method includes providing the wound healing composition and applying the wound healing composition to a wound in a subject afflicted with a wound. In some embodiments, the wound healing composition is provided as a ready-to-use formulation that includes hypochlorite or acids or salts thereof, silicone polymer or a blend of silicone polymers, and sodium magnesium silicate, and further may include sodium phosphate, HCl, water, or buffer. In some embodiments, the wound healing composition is provided in portions, and further additions and/or mixing is required prior to use. In some embodiments, the wound healing composition is applied topically to a wound.

In some embodiments, the wound healing formulation is an ointment, a cream, a spray, a spritz, a mist, a liquid, a gel, a lotion, or a solution. In some embodiments, the formulation is configured to be applied to a wound dressing material, including a bandage, a wipe, a gauze, a sponge, a mesh, or other absorbent wound dressing material. In some embodiments, the wound is skin damage, a burn, an abrasion, a laceration, an incision, a sore, a puncture wound, a penetration wound, a gunshot wound, or a crushing injury.

In some embodiments, the wound healing formulation is applied to the wound at least once daily. In some embodiments, the wound healing formulation is applied to the wound three times a day. In some embodiments, the wound healing composition is applied multiple times daily, once daily, multiple times weekly, once weekly, multiple times monthly, or once monthly, or within a time frame defined by any two of the aforementioned time frames. In some embodiments, the wound healing composition is applied liberally. In some embodiments, the wound healing composition is applied meagerly.

In some embodiments, the wound healing composition as disclosed herein is useful for disinfecting a wound. In some embodiments, the wound healing composition described herein is used in a healthcare facility setting. In some embodiments, the wound healing composition includes hypochlorite, or a salt or acid thereof, a blend of dimethicone and cyclomethicone, and sodium magnesium silicate. In some embodiments, the wound healing composition includes water and/or buffer, hypochlorous acid solution, a blend of dimethicone and cyclomethicone, sodium magnesium silicate, sodium phosphate, and HCl.

In some embodiments, applying the wound healing formulation provides a wound healing rate that is accelerated in comparison to a healing rate of a non-treated wound. In some embodiments, the formulation is applied in an amount effective to accelerate wound healing, promote wound closure, or cause wound regression. In some embodiments, the applying the formulation reduces, attenuates, or prevents bacterial growth or infection in the wound.

In some embodiments, the wound healing composition as disclosed herein is useful as medicament for wound healing or as a an ointment, a cream, a spray, a spritz, a mist, a liquid, a gel, a lotion, or a solution. In some embodiments, the composition is configured to be applied to a wound dressing material, including a bandage, a wipe, a gauze, a sponge, a mesh, or other absorbent wound dressing material.

In some embodiments, the formulations may further contain additives such as colorants, fragrances, buffers, oils, moisturizers, emollients, peptides, vitamins, minerals, oils, hyaluronic acids, ceramides, glycerins, glycerols, glycols, alcohols, caffeine, alpha hydroxyl acids (glycolic acids), plant extracts, physiologically acceptable carriers and/or excipients, and the like. In some embodiments, suitable colorants may include, but are not limited to, titanium dioxide, iron oxides, carbazole violet, chromium-cobaltaluminum oxide, 4-Bis[(2-hydroxyethyl)amino]-9, 10-anthracenedione bis(2-propenoic)ester copolymers, and the like. In some embodiments, any suitable fragrance can be used.

In some embodiments, the formulations include one or more additives in any suitable concentrations. For example, the one or more additives can be between about 0.1% w/v and 10% w/v of the formulation. The additive can also be between about 1% w/v and 8% w/v of the formulation. The additive can also be between about 2% w/v and 6% w/v. The additive can also be between about 4% w/v and 6% w/v. The additive can also be between about 1%, 2%, 3%, 4%, 5%, 6%, 7%, 8%, 9%, and 10% weight to volume of the formulation. In some embodiments, formulations including ROS and RS are produced in any suitable manner that results in a formulation containing effective amounts of ROS and RS. FIG. 2 illustrates embodiments of a process 10 for producing formulations including ROS and RS. Process 10 can include any suitable steps for producing topical formulations including ROS and RS. In some embodiments, process 10 includes an optional step 100 of preparing an electrolyzed saline solution, an optional step 200 of adding a rheology modifier, an optional step 300 of adding a buffering agent, an optional step 400 of adding an additive, and/or an optional step 500 of packaging the topical formulation. Optional steps 100, 200, 300, 400, and/or 500 can be carried out in any suitable order to produce topical formulations including ROS. For example, in some embodiments, rheology modifier is added to an electrolyzed saline solution, followed by addition of buffering agent, addition of additives, and packaging of the formulation. In other embodiments, buffering agent is added to the electrolyzed saline solution followed by rheology modifier. In yet other embodiments, rheology modifier and buffering agent are mixed together and then added to the electrolyzed saline solution. In some embodiments, electrolyzed saline solution, buffering agent, and additives are first mixed together and then rheology modifier is added.

In some embodiments, optional step 100 includes any suitable steps for preparing an electrolyzed saline solution (ESS). In other embodiments, the electrolyzed saline solution is prepared as described herein. Methods of producing the electrolyzed saline solution can include one or more of preparing an ultra-pure saline solution, inserting a set of inert catalytic electrodes, and controlling temperature and flow while applying current across the electrodes to activate a modulated electrolytic process to form stable molecular moieties and complexes such as RS molecules and ROS molecules. In some embodiments, optional step 100 includes preparing an ultra-pure saline solution including about 2.8 g/L of sodium chloride, inserting a set of inert catalytic electrodes, and controlling temperature and flow while applying about 3 A of current across the electrodes, while maintaining the ultra-pure saline solution at or below room temperature during 3 minutes of electrolysis. In other embodiments, optional step 100 includes preparing an ultra-pure saline solution including about 9.1 g/L of sodium chloride, inserting a set of inert catalytic electrodes, and controlling temperature and flow while applying about 3 A of current across the electrodes, while maintaining the ultra-pure saline solution at or below room temperature during 3 minutes of electrolysis.

Figure 3:
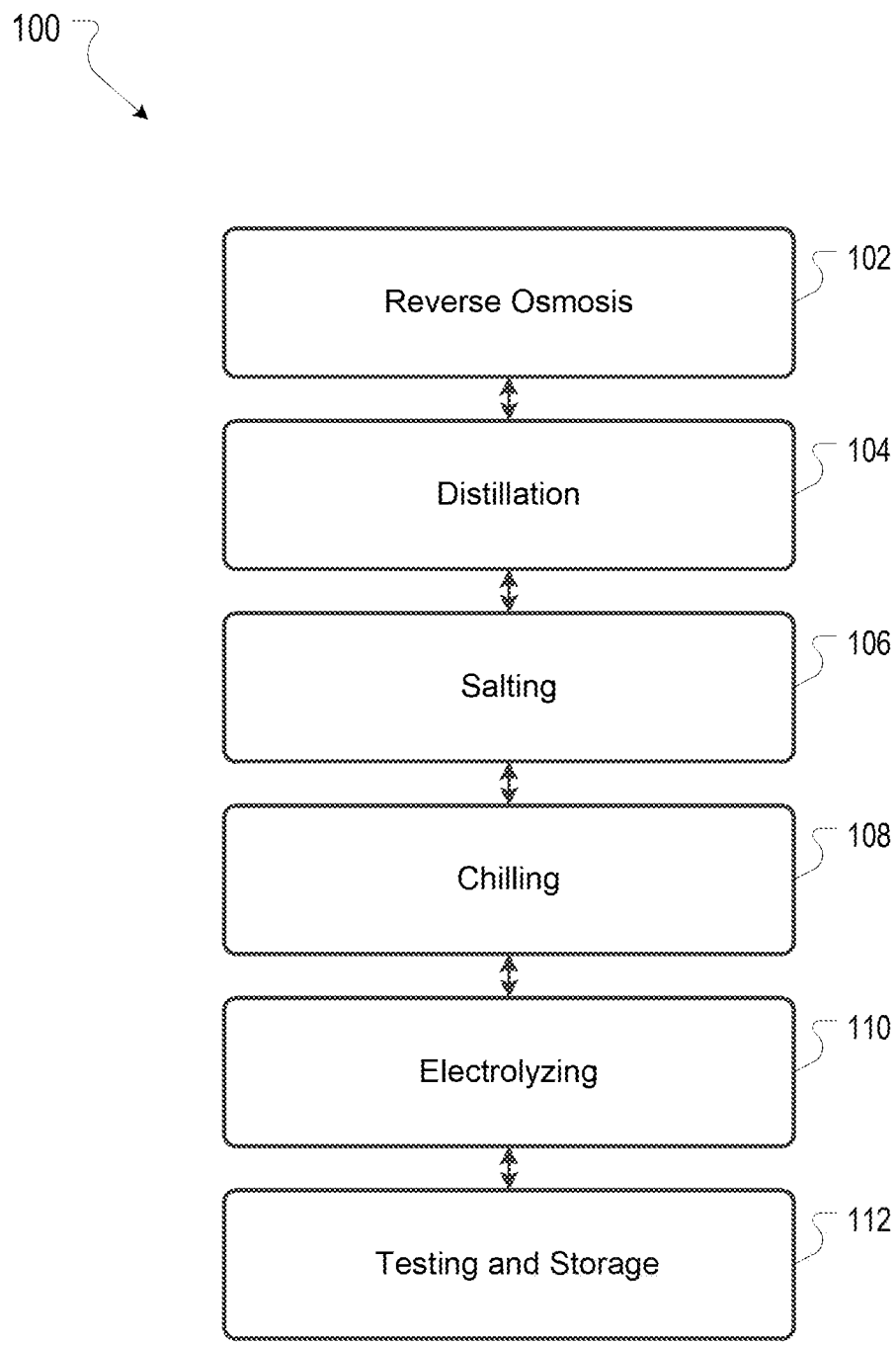
FIG. 3 illustrates a plan view of a process and system for producing electrolyzed saline solution to prepare a formulation according to the present description.

FIG. 3 illustrates embodiments of the optional step 100 for preparing an electrolyzed saline solution. The optional step 100 can include an optional step 102 of reverse osmosis, an optional step 104 of distillation, an optional step 106 of salting, an optional step 108 of chilling, an optional step 110 of electrolyzing, and/or an optional step 112 of storage and testing.

In some embodiments, the electrolyzed saline solution is prepared from water. This input water can be supplied from any suitable source. For example, water can be supplied from a variety of sources, including but not limited to, municipal water, spring water, filtered water, distilled water, microfiltered water, or the like.

In some embodiments, any suitable purification method is used to prepare the water. In other embodiments, any suitable purification method is used to remove contaminants from the water. For example, an optional step 102 of reverse osmosis filtration can be used to prepare the water. In some cases, reverse osmosis filtration includes removing contaminants from the input water by pretreating the input water with an activated carbon filter to remove the aromatic and volatile contaminants followed by reverse osmosis (RO) filtration to remove dissolved solids and most organic and inorganic contaminants. In some embodiments, the reverse osmosis process can be performed at a temperature of about 5° C., about 10° C., about 15° C., about 20° C., about 25° C., about 30° C., about 35° C., or the like.

In some embodiments, an optional step 104 of distillation is used. A distillation step can be used remove contaminants. In some instances, contaminants can be removed through the distillation step, resulting in dissolved solid measurement of less than 1 ppm. In addition to removing contaminants, distillation may also serve to condition the water with the correct structure and oxidation reduction potential (ORP) to facilitate the oxidative and reductive reaction potentials on the platinum electrodes in the subsequent electro-catalytic process. In some embodiments, the distillation process can vary, but can provide water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. In other embodiments the temperature of the distillation process can be performed at a temperature of about 5° C., about 10° C., about 15° C., about 20° C., about 25° C., about 30° C., about 35° C., or the like. In some embodiments, the distillation step can be repeated as needed to achieve a particular total dissolved solids level.

In some embodiments, optional step 100 includes one or more other known processes for water purification to reduce the amount of total dissolved solids. Other known processes for water can include filtration and/or purification process such deionization, carbon filtration, double-distillation, electrodeionization, resin filtration, microfiltration, ultrafiltration, ultraviolet oxidation, electrodialysis, or combinations thereof.

In some embodiments, water prepared by reverse osmosis, distillation, and/or other known processes is referred to as ultra-pure water. Ultra-pure water can have a total dissolved solids count of less than about 10 ppm, about 9 ppm, about 8 ppm, about 7 ppm, about 6 ppm, about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. In other embodiments, the reverse osmosis process and/or distillation process provide water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. The reverse osmosis process, the distillation process and/or other known processes can be repeated as needed to achieve a particular total dissolved solids level.

Figure 4:
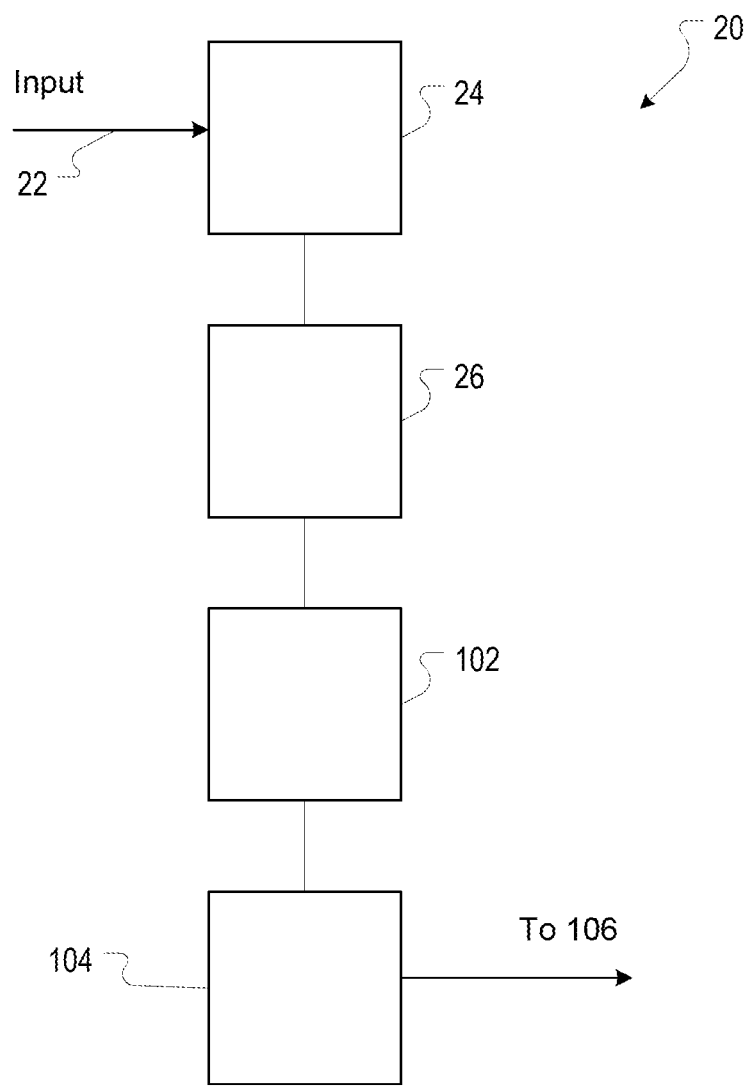
FIG. 4 illustrates an example system for preparing water for further processing into a formulation described herein.

As shown in FIG. 4, in some embodiments, a system 20 is used to purify the water prior to reverse osmosis and/or distillation. System 20 can include a water source 22. The water source 22 can be directed to a carbon filter system 24. Carbon filter 24 can be configured to remove oils, alcohols, and other volatile chemical residuals and particulates from the water. The post-carbon filter water can then pass into a water softener 26. The water softener 26 can be configured with resin beds configured to remove dissolved minerals. Then, as described above, the post-water softener water can pass through reverse osmosis step 102 and distillation step 104.

Referring again to FIG. 3, in some embodiments, any suitable method is used to add salt to the water to prepare the saline solution. In other embodiments, any suitable method is used to add salt to the ultra-pure water. For example, as shown in FIG. 3, an optional step 106 of salting can be used to add salt to the water. The salt can be any salt and/or mixture of salts suitable for preparing a saline solution. The salt can be in any suitable form (e.g., unrefined, refined, caked, de-caked, or the like). In one embodiment, the salt includes a sodium chloride (NaCl). In other embodiments, the salt include one or more of lithium chloride, sodium chloride, potassium chloride, rubidium chloride, cesium chloride, magnesium chloride, calcium chloride, strontium chloride, copper chloride, copper sulfate, and iron chloride. In yet other embodiments, the salt includes one or more of a chloride salt, a phosphate salt, a nitrate salt, an acetate salt, a lithium salt, a sodium salt, a potassium salt, a magnesium salt, a calcium salt, and an iron salt.

In some embodiments, the salt includes one or more additives. Salt additives can include, but are not limited to, potassium iodide, sodium iodide, sodium iodate, dextrose, glucose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, lactate, phosphates, tris, borates, carbonates, citrates, and folic acid. In some embodiments, one or more additives are added at the salting step. In other embodiments, one or more additives are added at any point in the preparation of the electrolyzed saline solution. In yet other embodiments, one or more additives are added after electrolysis.

In some embodiments, the prepared saline is generally free from contaminants, both organic and inorganic, and homogeneous down to the molecular level. In particular, because some metal ions can interfere with electro-catalytic surface reactions, it may be helpful for some metal ions to be removed and/or absent from the saline solution.

In another embodiment, the saline solution includes any suitable ionic soluble salt mixture (e.g., saline containing chlorides). In addition to NaCl, other non-limiting examples include LiCl, HCl, $CuCl_2$, $CuSO_4$, KCl, $MgCl_2$, $CaCl_2$, sulfates and phosphates. In some instances, strong acids such as sulfuric acid ($H_2SO_4$) and strong bases such as potassium hydroxide (KOH) and sodium hydroxide (NaOH) can be used as electrolytes due to their strong conducting abilities.

In some embodiments, the salt(s) and any additive(s) are added in any suitable form to the water. In other embodiments, the salt(s) and any additive(s) are added in a solid form to the water. In yet other embodiments, the salt(s) and any additive(s) are added to the water in the form of a concentrated brine solution. A brine solution can be used to introduce the salt into the water. The brine solution can be prepared at any suitable concentration and can be diluted at any suitable ratio. In yet other embodiments, a brine solution of sodium chloride is used to salt the water. The brine solution can have a NaCl concentration of about 540 g NaCl/gal, such as 537.5 g NaCl/gal.

In some embodiments, the brine solution is prepared with one or more of a physical mixing apparatus and/or a circulation/recirculation apparatus. In one embodiment, pure pharmaceutical grade sodium chloride is dissolved in the ultra-pure water to form a 15% w/v sub-saturated brine solution and continuously re-circulated and filtered until the salt has completely dissolved and all particles >0.1 microns are dissolved. In some cases, the recirculation and filtration can be carried out for several days. The filtered, dissolved brine solution can then be injected into tanks of distilled water in about a 1:352 ratio (brine:salt water) in order to form a 0.3% saline solution.

In some embodiments, the brine solution is added to the water to achieve a salt concentration of between about 1 g/gal water and about 25 g/gal water, between about 8 g/gal water and about 12 g/gal water, or between about 4 g/gal water and about 16 g/gal water. In a preferred example, the achieved salt concentration is 2.8 g/L of water. In another preferred example, the achieved salt concentration is 9.1 g/L of water. Once brine is added to the water at an appropriate amount, the solution can be thoroughly mixed. The temperature of the liquid during mixing can be at room temperature or controlled to a desired temperature or temperature range. To mix the solution, a physical mixing apparatus can be used or a circulation or recirculation can be used.

In some embodiments, the saline solution is maintained at any suitable temperature for electrolysis. In other embodiments, the saline solution is chilled in an optional step 108 of a chilling step as shown in FIG. 3. The saline solution can be chilled in any suitable manner for electrolysis. In some embodiments, various chilling and cooling methods are employed. For example cryogenic cooling using liquid nitrogen cooling lines can be used. Likewise, the saline solution can be run through propylene glycol heat exchangers to achieve any desired temperature. The chilling method and/or chilling time can vary depending on one or more of the volume of the saline solution, the starting temperature, and the desired chilled temperature.

In some embodiments, the saline solution is chilled prior to electrolysis. In other embodiments, the saline solution is continuously chilled during electrolysis. In yet other embodiments, the saline solution is continuously chilled and recirculated during electrolysis.

In some embodiments, the saline solution is electrolyzed in any suitable manner to generate the electrolyzed saline solution. In other embodiments, the saline solution can undergo electrochemical processing through the use of at least one electrode in an electrolyzing step 110 of FIG. 3. Each electrode can include a conductive metal. Electrode metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. I some embodiments, each electrode is formed of titanium and plated with platinum. The platinum surfaces on the electrodes by themselves can be optimal to catalyze the required reactions. The platinum plating can be configured as a rough, double layered platinum plating configured to assure that local "reaction centers" (sharply pointed extrusions) are active and prevent the reactants from making contact with the underlying electrode titanium substrate.

In one embodiment, rough platinum-plated mesh electrodes in a vertical, coaxial, cylindrical geometry are used, with, for example, not more than 2.5 cm, not more than 5 cm, not more than 10 cm, not more than 20 cm, or not more than 50 cm separation between the anode and cathode. The current run through each electrode can be between about 2 amps and about 15 amps, between about 4 amps and about 14 amps, at least about 2 amps, at least about 4 amps, at least about 6 amps, or any range created using any of these values. In one embodiment, 7 amps of current is applied across each electrode. In one example, 1 amp of current is run through the electrodes. In one example, 2 amps of current are run through the electrodes. In one example, 3 amps of current are run through the electrodes. In one example, 4 amps of current are run through the electrodes. In one example, 5 amps of current are applied to the electrodes. In one example, 6 amps of current are applied to the electrodes. In one example, 7 amps of current are applied to the electrodes. In a preferred example, 3 amps of current are applied to the electrodes.

In some embodiments, current is applied to the electrodes for a sufficient time to electrolyze the saline solution. The saline solution can be chilled during the electrochemical process. The solution can also be mixed during the electrochemical process. This mixing can be performed to ensure substantially complete electrolysis. In some embodiments, electrolysis products formed at the anode surface are effectively transported to the cathode surfaces to provide the reactants necessary to generate stable complexes on the cathode surfaces. Maintaining a high degree of homogeneity in the saline solution circulated between the catalytic surfaces can also be helpful to generate stable complexes. In some embodiments, a constant flow of about 2-8 ml/cm$^2$ per second of the saline solution can be used with typical a mesh electrode spacing of 2 cm. This constant flow of saline solution can be maintained, in part, by the convective flow of gasses released from the electrodes during electrolysis.

In some embodiments, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.5° C. throughout electrolysis. The temperature of the solution at the time or duration of the electrolysis can be below 10° C. In a preferred embodiment, the temperature of the solution at the time or duration of the electrolysis is 10° C. or 9° C. or 8° C. or 7° C. or 6° C. or 5° C. or 4° C. or 3° C. or 2° C. or 1° C. or –1° C. or –2° C. or –3° C. or –4° C. or –5° C. or –6° C. or –7° C. or –8° C. or –9° C. or –10° C. The temperature can be within a range as well such as between 1 to 10° C. or, 3 to 7° C. or 4 to 6° C. Preferably the temperature during electrolysis is from 4 to 6° C. Most preferably, the temperature during electrolysis is from 4.5 to 5.8° C.

In some embodiments, electric fields between the electrodes can cause movement of ions. This movement of ions can enable exchange of reactants and products between the electrodes. In some embodiments, no membranes or barriers are placed between the electrodes. In other embodiments, the electrolysis process is performed in a single container as a batch process.

The saline solution can be electrolyzed for an amount of time required based on the particular results desired. For example, the saline solution can be electrolyzed from about 1 minute to about 5 days. Preferably, the saline solution can be electrolyzed from about 20 minutes to about 2 days. More preferably, the saline solution is electrolyzed for 1-60 minutes for every 1 L, 10-40 minutes for every 1 L, or 20-30 minutes for every 1 L. For example, the saline solution can be electrolyzed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes or 60 minutes for each 1 L of saline solution.

The saline solution can be electrolyzed for any amount of time in between 1 to 60 minutes for every 1 L of saline solution. For example, the saline solution can be electrolyzed for a time between 1 and 2 minutes or for a time between 2 to 3 minutes etc. For example, the saline solution can be electrolyzed for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes or about 60 minutes for each 1 L of saline solution. Most preferably the saline solution is electrolyzed for 15 to 25 minutes or any time in between. For example, the saline solution is electrolyzed for about 15 to about 25 minutes or any time in between.

The variables of voltage, amps, frequency, time and current required depend on the compound and/or ion themselves and their respective bond strengths. To that end, the variables of voltage, amps, frequency, time and current are compound and/or ion dependent and are not limiting factors. That notwithstanding, the voltage used can be less than 40V, such as 30V or 20V or 10V or any voltage in between. The voltage can also modulate and at any time vary within a range of from 1 to 40V or from 10 to 30V or from 20 to 30V. In one embodiment, the voltage can range during a single cycle of electrolyzing. The range can be from 1 to 40V or from 10 to 30V or from 20 to 30V. These ranges are non-limiting but are shown as examples.

Waveforms with an AC ripple also referred to as pulse or spiking waveforms include: any positive pulsing currents such as pulsed waves, pulse train, square wave, saw tooth wave, spiked waveforms, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid state diodes, silicon-controlled rectifiers and the like. Pulsed waveforms can be made with a transistor regulated power supply, a dropper type power supply, a switching power supply and the like.

A transformer may be used. Examples of transformers that can be used include center tapped transformers, autotransformers, capacitor voltage transformers, distribution transformers, power transformers, phase angle regulating transformers, Scott-T transformers, polyphase transformers, grounding transformers, leakage transformers, resonant transformers, audio transformers, output transformers, laminated core toroidal autotransformers, variable autotransformers, induction regulators, stray field transformers, solyphase transformer, constant voltage transformer, ferrite core planar transformers, oil cooled transformers, cast resin transformers, isolating transformers, instrument transformers, current transformers, potential transformers, pulse transformers, air-core transformers, ferrite-core transformers, transmission line transformers, balun audio transformers, loudspeaker transformers, output transformers, small signal transformers, interstage coupling transformers, hedgehog or variocoupler transformers.

Pulsing potentials in the power supply of the production units can also be built in. Lack of filter capacitors in the rectified power supply can cause the voltages to drop to zero a predetermined amount of times per second. For example, at 60 Hz the voltage can spike 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals. In one embodiment, the pulsing potentials can vary based on the desired functional parameters and capabilities of the apparatus and equipment and to that end can vary from very high potentials to low potentials and from very high frequencies to very low frequencies. In one embodiment, the voltage potential must go down to zero periodically. The voltage can go to 0 V as many times per second as is physically possible. In some embodiments, the voltage is 0 V between 100 and 200 times per second. In a preferred embodiment, the voltage goes down to 0 V 120 times per second.

In some embodiments, there is no limit to the how high the voltage potential can go. For example, the voltage potential can pulse from 0V to 40V. In some embodiments, the voltage range can change or be changed so that the range changes as often or as little as desired within any given amount of time. This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second. When the V goes down to zero it is believe that the 0 V allows for ions to drift apart/migrate and reorganize before the next increase in V. It is theorized that this spiking in V allows for and promotes a variable range of frequencies influencing many different types of compounds and/or ions so that this process occurs.

In one embodiment, periodic moments of 0 volts are required. Again, when the V goes down to zero it is believe that the 0 V allows for ions to drift apart/migrate and reorganize before the next increase in V. Therefore, without being bound to theory, it is believed that this migration of ions facilitates the 1st, 2nd, and 3rd generations of species as shown in FIG. 1. Stabilized superoxides, such as $O_2^{*-}$, are produced by this method. In another embodiment, the V is always either zero or a positive potential. In some embodiments, diodes are used. The V may drop to zero as many times per second as the frequency is adjusted. As the frequency is increased the number of times the V drops is increased. The frequency can be from 1 Hz to infinity or to 100 MHz. Preferably, the frequency is from 20 Hz to 100 Hz. More preferably, the frequency is from 40 Hz to 80 Hz. Most preferably, the frequency is 60 Hz. In another embodiment, the frequency changes during the course of the electrolyzing process. For example, the frequency at any given moment is in the range from 20 Hz to 100 Hz. In another more preferred embodiment, the frequency at any given moment is in the range from 40 Hz to 80 Hz.

In some embodiments, after current has been applied to the saline solution for a suitable time, an electrolyzed solution is created. In other embodiments, an electrolyzed solution is created with beneficial properties (e.g., cellulite treating properties). The electrolyzed saline solution can be stored and/or tested for particular properties in an optional testing and storage step 112 of method 100.

In some embodiments, the electrolyzed saline solution is tested in any suitable manner for any suitable characteristics. For example, the electrolyzed saline solution can be subjected to quality assurance testing. Quality assurance test can include, without limitation, one or more of determination of pH, determination of presence of contaminants (e.g., heavy metals, chlorate, and/or any other contaminants), determination of oxidative reductive potential, determination of free chlorine concentrations, determination of total chlorine concentration, determination of reactive molecule concentration, and/or any other suitable testing. In some instances quality assurance testing is done on every batch after electrolysis. In some cases, a sample can be taken from each electrolysis batch and analyzed. Testing to determine the presence of contaminants such as heavy metals or chlorates can be performed. Additionally, pH testing, free chlorine testing, and total chlorine testing can be performed.

In some cases, a chemical chromospectroscopic mass spectroscopy analysis can also be performed on the sample to determine if contaminants from the production process are present.

In some embodiments, the electrolyzed saline solution is tested for the presence of and/or concentration of ROS and RS species. For example, the electrolyzed saline solution can be assayed to determine if the electrolyzed saline solution mimics the desired balanced target mixture of redox-signaling molecules that are found in healthy living cells. If assays reveal that the electrolyzed saline solution mimics the desired balanced target mixture of redox-signaling molecules that are found in healthy living cells, the electrolyzed saline solution can then be used to prepare the topical formulation. If the assays reveal that the electrolyzed saline solution does not replicate the desired balanced target mixture of redox-signaling molecules that are found in healthy living cells, the batch can be rejected and a new batch of electrolyzed saline solution can be prepared while varying any suitable electrolysis parameter (e.g., temperature, flow, pH, power-source modulation, salt makeup, salt homogeneity, and salt concentration) such that the ROS and RS measurements of the electrolyzed saline solution can replicate the ROS and RS measurements of the balanced target mixture.

In some embodiments, one or more of the fluorescent indicators, R-Phycoerythrin (RPE), Aminophenyl fluorescein (APF) and Hydroxyphenyl fluorescein (HPF) are used to measure concentrations of ROS and RS in the electrolyzed saline solution. These fluorescent indicator molecules exhibit a change in fluorescence when they contact specific redox species. These corresponding changes in fluorescence can then be measured to verify and quantify the existence and relative concentration of the corresponding redox species. A combination of measurements from these indicators can be utilized to measure the concentration of ROS and RS in the electrolyzed saline solution. These measured concentrations of ROS and RS can then be compared to verify that the electrolyzed saline solution replicates the desired balanced target mixture of redox-signaling molecules that are found in healthy living cells.

In some embodiments, any suitable assay is used to determine if the electrolyzed saline solution replicates the balanced target mixture of redox-signaling molecules that are found in healthy living cells. For example, assays to measure the concentration of ROS and RS in the electrolyzed saline solution can include assays to measure pH, potassium iodide titration with $Na_2S_2O_3$ to determine $ClO^-$, inductively coupled plasma mass spectroscopy (ICP-MS) to detect metals and non-metals (e.g., to determine content of ions such as chlorine), $^{35}Cl$ NMR to determine content of ions such as chlorine, proton NMR to determine characteristics such as organic material content, and $^{31}P$ NMR to determine content of ions such as OH*. In other embodiments, any suitable assay is also used to determine the stability of the electrolyzed saline solution.

In some embodiments, the electrolyzed saline solution is used directly to prepare the topical formulation. In other embodiments, the electrolyzed saline solution is stored in any suitable manner before preparation of the topical formulation. For example, the electrolyzed saline solution can be stored at any suitable temperature in biocompatible containers. In some instances, the electrolyzed saline solution can be stored in non-reactive amber glass bottles. In other instances, the electrolyzed saline solution can be stored in non-reactive polymer bottles.

Referring again to FIG. 2, in some embodiments the formulation is prepared by adding one or more of rheology modifier, buffering agent, and/or additive(s) to the electrolyzed saline solution (e.g., as shown in optional steps 200, 300, 400, and 500). As described above, the addition of one or more of the components to the electrolyzed saline solution can be done in any suitable order or fashion.

In some embodiments, In optional step 200, rheology modifier is added to the electrolyzed saline solution in any suitable fashion to prepare the topical formulation. For example, the rheology modifier can be mixed with the electrolyzed saline solution to form a viscous solution before other components are added. In some instances, the rheology modifier can be added into the electrolyzed saline solutions as the solution is being mixed to allow for even dispersion of the rheology modifier. In other instances, purified water or any other suitable solution can be added to the mixture of electrolyzed saline solution and rheology modifier to achieve the desired viscosity.

In some embodiments, optional step 200 includes adding rheology modifier in any suitable amount to achieve the desired viscosity of the topical formulation. For example, the weight percent of the electrolyzed saline solution in the topical formulation can be from about 50% w/v to about 99.9% w/v. In some embodiments, the weight percent of the electrolyzed saline solution in the topical formulation is from about 90 to 99.1% by weight or from about 95 to 99.1%. In other embodiments, the weight percent of the electrolyzed saline solution in the topical formulation is about 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In yet other embodiments, weight percent of the electrolyzed saline solution in the topical formulation is about 98% or 99% by weight. These weight percentages can be approximate and can be modified to achieve specific characteristics desired and/or required in the topical formulation.

In some embodiments, the rheology modifier is added to the electrolyzed saline solution at any suitable temperature and/or at any suitable pH. For example, in some cases, a lower temperature may result in longer hydration times for the rheology modifier. Likewise, in some cases, a higher temperature may result in shorter hydration times. Therefore, in some instances, the temperature can be tailored to provide a suitable hydration time to prepare the topical formulation. In other embodiments, the pH of the rheology modifier and electrolyzed saline solution mixture is adjusted to achieve suitable hydration of the rheology modifier. For example, in the case of acrylic acid polymers, the mixture can be neutralized by addition of a strong base to form a polymer salt to achieve a suitable viscosity. In yet other embodiments, co-polymers are added to the rheology modifier to achieve a suitable viscosity. For example, copolymers such as allyl sucrose and/or allylpentaerythritol can be added to achieve a suitable viscosity.

In some embodiments, buffering agent includes any suitable buffering agent. As described above, the buffering agent can include any suitable buffering agent compatible with the topical formulation. In other embodiments, optional step 300 includes adding buffering agent to the topical formulation in any suitable manner. In some cases, the buffering agent is added to the mixture of rheology modifier and electrolyzed saline solution. In other cases, the buffering agent is added to the electrolyzed saline solution. In some embodiments, the buffering agent is prepared as a pH-adjusted stock solution that is added to the topical formulation. In other embodiments, the buffering agent is added as a solid. In yet other embodiments, the buffering agent is added to the topical formulation and then the pH is adjusted to a suitable pH. For example, a strong acid and/or a strong base can be added to the mixture of the buffering agent and other components to adjust the pH to a suitable pH. In some embodiments, the buffering agent is added to the topical formulation immediately before use.

In some embodiments, optional step 400 includes adding any suitable additive(s) in any suitable fashion to the topical formulation. In other embodiments, any suitable additive(s) are added at any point in process 10. Indeed, additives may be added at any point in the preparation of the electrolyzed saline solution (e.g., during salting, during chilling, and/or during electrolysis). Likewise, additives may be added before, during, and/or after adding rheology modifier, adding buffering agent and/or packaging. In yet other embodiments, additive(s) may be added to the topical formulation immediately before use In some embodiments, optional step 500 includes packaging the topical formulation in any suitable manner. Packaging can include dispensing the topical formulation into suitable containers. Suitable containers can include, without limitation, glass containers, amber glass containers, ceramic containers, polymer containers, squeeze bottles, squeeze tubes, squeezable pouches, manual pump dispenser, and any other suitable container. Packaging can include single use aliquots in single use packaging such as pouches. The topical formulation can be packaged in plastic bottles having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or any range created using any of these values. The plastic bottles can also be plastic squeezable pouches having similar volumes.

In some embodiments, packaging is generally free of any dyes, metal specks or chemicals that can be dissolved by acids or oxidizing agents. In other embodiments, any bottles, package caps, bottling filters, valves, lines and heads used in packaging are specifically rated for acids and oxidizing agents. In some cases, package caps with any organic glues, seals or other components sensitive to oxidation may be avoided since they could neutralize and weaken the product over time.

In some embodiments, the packaging used herein reduces decay of free radical species (ROS and/or RS) found within the topical formulations. In other embodiments, the packaging described does not further the decay process. In other words, the packaging used can be inert with respect to the ROS and/or RS species in the topical formulations. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of ROS and/or RS in the composition. In one embodiment, a bottle can only result In about 3% decay/month of superoxide. In another embodiment, a pouch can only result In about 4% decay/month of superoxide.

The present application provides methods of treating a wound in a subject afflicted with a wound by administering a therapeutic amount of the described formulation to a subject in need. In some embodiments, administering the formulation includes administering a therapeutic amount of the topical formulation to a subject in any suitable manner. A subject can include a human, a mammal, an animal, an animal kept as a pet, livestock, zoo animals, and the like. In other embodiments, the formulation is administered by topically applying a therapeutic amount of the formulation to the wound or surrounding area of the subject. In yet other embodiments, the formulation is applied to areas that are affected by a wound.

In some embodiments, the formulation is applied directly to an affected area of the subject's skin. In other embodiments, the topical formulation is applied directly to the affected area by one or more of a dropper, a brush, a cotton swab, an applicator stick, a roller ball applicator, as a mist or aerosol, as a transdermal patch, by wiping with a wipe, by spreading the formulation on the area with fingers, or by any other similar methods. The formulation can be applied to the affected area in any suitable therapeutic amount. In some embodiments, the formulation is configured to be applied to a wound dressing material, including a bandage, a wipe, a gauze, a sponge, a mesh, or other absorbent wound dressing material. In some embodiments, the topical formulation is administered and/or applied to the subject in gram units such as from about 0.05 g to about 2 g or as desired by the subject. When applied to the subject, it can be applied once, twice, three times, four times or more a day. It can be applied every other day, every three days, every four days, every five days, every six days, every week, every two weeks, every three weeks, or every month. Each application to the subject can be about 0.05 g, about 0.06 g, about 0.07 g, about 0.08 g, about 0.09 g, about 0.1 g, about 0.2 g, about 0.3 g, about 0.4 g, about 0.5 g, about 0.6 g, about 0.7 g, about 0.8 g, about 0.9 g, about 1.0 g, about 1.1 g, about 1.2 g, about 1.3 g, about 1.4 g, about 1.5 g, about 1.6 g, about 1.7 g, about 1.8 g, about 1.9 g, or about 2.0 g. In one embodiment, the formulation can be applied to the subject at a rate of about 0.4 g once a day.

In other embodiments, the administration and/or application to the subject can be acute or long term. For example, the composition can be administered to the subject for a day, a week, a month, a year or longer. In other embodiments, the composition can simply be applied to the subject as needed.

The present application provides methods of treating a wound in a subject by administering a therapeutic amount of the described formulation to a subject. In some embodiments, the formulation is administered by topically applying a therapeutic amount of the formulations to areas of the subject's wound.

In other embodiments, the treating with the formulation can be acute or long term. For example, the formulation can be administered to the subject for a day, a week, a month, a year or longer to treat a wound. In some cases, the formulation can be administered daily for at least six weeks to treat the wound. In other cases, the formulation can be administered daily for at least twelve weeks to treat the wound. In other embodiments, the formulation can simply be applied to the subject as needed to treat the wound.

In some embodiments, treating the wound includes applying the formulation to affected area or region, and application of the composition increases the elasticity of the skin at the treated area. In some cases, the elasticity of an area of skin at or near the wound can be measured before treatment. The affected area can then be treated and the elasticity of the treated area can be measured. In other cases, the treated area can exhibit an increase in elasticity. In some instances, the increase in elasticity of the treated area can be up to about 1%, about 2%, about 3%, about 4%, about 5%, about 6%, about 7%, about 8%, about 9%, about 10%, about 15%, about 20%, about 25%, about 30%, about 35%, and about 40%. In other instances, the increase in elasticity can be seen after 1 day, after 2 days, after 3 day, after 4 days, after 5 days, after 6 days, after 1 week, after 2 weeks, after 3 weeks, after 4 weeks, after 5 weeks, after 6 weeks, after 7 weeks, after 8 weeks, after 9 weeks, after 10 weeks, after 11 weeks, after 12 weeks, after 13 weeks, after 14 weeks, and after 15 weeks.

In some embodiments, treating the wound includes applying the formulation to the wound to decrease the appearance of wrinkles and fine lines in the treated area. In some cases, the appearance of fine lines and wrinkles in affected skin can be measured before treatment. The affected area can then be treated and the appearance of fine lines and wrinkles of the treated area can be measured. In other cases, the treated area can exhibit a decrease in the appearance of fine lines and wrinkles. In some instances, the decrease in appearance of fine lines and wrinkles of the treated area can be up to about 1%, about 2%, about 3%, about 4%, about 5%, about 6%, about 7%, about 8%, about 9%, about 10%, about 15%, about 20%, about 25%, about 30%, about 35%, and about 40%.

In some embodiments, treating the wound includes methods for applying the formulation to the wound. These methods can include one or more of: gently washing the affected area with a mild cleanser to ensure that the wound and surrounding area is clean; dispensing a therapeutically effective amount of the formulation; applying the amount of the formulation to a finger or applicator; and allowing the formulation to absorb into the wound and affected region.

In some embodiments, the formulation is used as part of a system of wound management to treat a wound and a surrounding region affected by the wound. For example, in some embodiments, the system includes one or more of an antimicrobial agent, an antibiotic, an anti-inflammatory, or an analgesic. In other embodiments, the system is configured to be effective against one or more of skin damage, a burn, an abrasion, a laceration, an incision, a sore, a puncture wound, a penetration wound, a gunshot wound, or a crushing injury.

The invention is generally disclosed herein using affirmative language to describe the numerous embodiments. The invention also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the invention as it is described herein above and/or in the claims.

Example 1

Electrolyzed Solution Preparation

An electrolyzed solution was produced as described above and then characterized. Briefly, input water was subjected to reverse osmosis at a temperature of about 15-20° C. to yield purified water with about 8 ppm of total dissolved solids. The water was distilled to yield distilled water with about 0.5 ppm of total dissolved solids. Sodium chloride brine solution was added to the distilled water to yield a saline solution of about 2.8 grams sodium chloride per liter (about 0.28% sodium chloride). The saline solution was thoroughly mixed by recirculation and the salinity was confirmed by handheld conductivity meter. The saline solution was chilled to about 4.5 to 5.8° C. The chilled saline solution was then electrolyzed with platinum coated titanium electrodes with a current of 7 amps per electrode while the saline solution was circulated. The voltage was maintained between 9 and 12 volts. The saline solution was maintained between 4.5 to 5.8° C. during electrolysis. The resulting electrolyzed saline solution had a pH of about 7.4. The composition was received and stored at about 4° C. when not being used. The electrolyzed saline solution was then analyzed using a variety of different characterization techniques.

Chlorine NMR

The electrolyzed saline solution sample was analyzed with chlorine NMR $^{35}$Cl NMR). Control solutions of 5% sodium hypochlorite were prepared at different pH values by titrating with concentration nitric acid. The control sodium hypochlorite solutions had pH values of 12.48, 9.99, 6.99, 5.32, and 3.28. The control sodium hypochlorite solutions and the electrolyzed saline solution sample were then analyzed by $^{35}$Cl NMR spectroscopy. The electrolyzed saline solution sample was analyzed without directly without dilution.

The $^{35}$Cl NMR spectroscopy experiments were performed using a 400 MHz Bruker spectrometer equipped with a BBO probe. The $^{35}$Cl NMR experiments were performed at a frequency of 39.2 MHz using single pulse experiments. A recycle delay of 10 seconds was used and 128 scans were acquired per sample. A solution of NaCl in water was used as an external chemical shift reference. All experiments were performed at room temperature.

Figure 5:
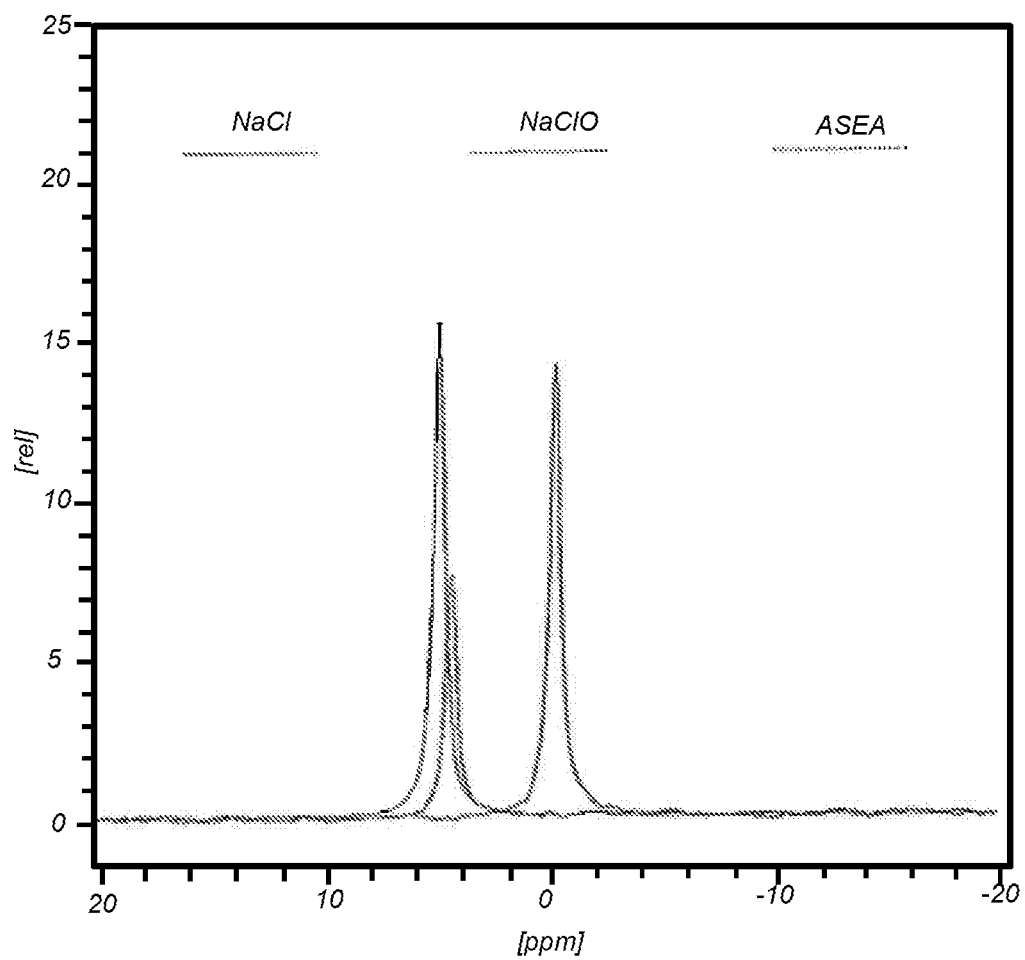
FIG. 5 illustrates a $^{35}Cl$ spectrum of NaCl, NaClO solution at a pH of 12.48, and an electrolyzed saline solution for preparing a formulation as described herein.

The $^{35}$Cl NMR spectra were collected for the NaCl chemical shift reference solution, the control NaClO solutions adjusted to different pH values, and the electrolyzed saline solution sample. FIG. 5 illustrates overlapping $^{35}$Cl NMR spectra of the NaCl chemical shift reference, a NaClO control solution at a pH of 12.48, and the electrolyzed saline solution sample. The chemical shift scale was referenced by setting the Cl peak to 0 ppm. The NaClO solutions with a pH above 7 exhibited identical spectra with a peak at approximately 5.1 ppm. In the NaClO control samples below a pH value of 7.0, the ClO$^-$ peak disappeared and was replaced by much broader, less easily identifiable peaks. The electrolyzed saline solution sample exhibited one peak at approximately 4.7 ppm. This peak likely corresponded to ClO$^-$ found in the sample. This peak at 4.7 ppm was integrated to estimate the concentration of ClO$^-$ in the sample. The integrated peak indicated that the concentration of ClO$^-$ in the sample was 2.99 ppt.

Proton NMR

The electrolyzed saline solution sample was analyzed with proton NMR. A test sample was prepared by adding 550 μL of the electrolyzed saline solution sample and 50 μL of $D_2O$ (Cambridge Isotope Laboratories) to an NMR tube and vortexing for 10 seconds. $^1H$ NMR experiments were performed on a 700 MHz Bruker spectrometer equipped with a QNP cryogenically cooled probe. Experiments used a single pulse with pre-saturation on the water resonance experiment. A total of 1024 scans were taken. All experiments were performed at room temperature.

Figure 6:
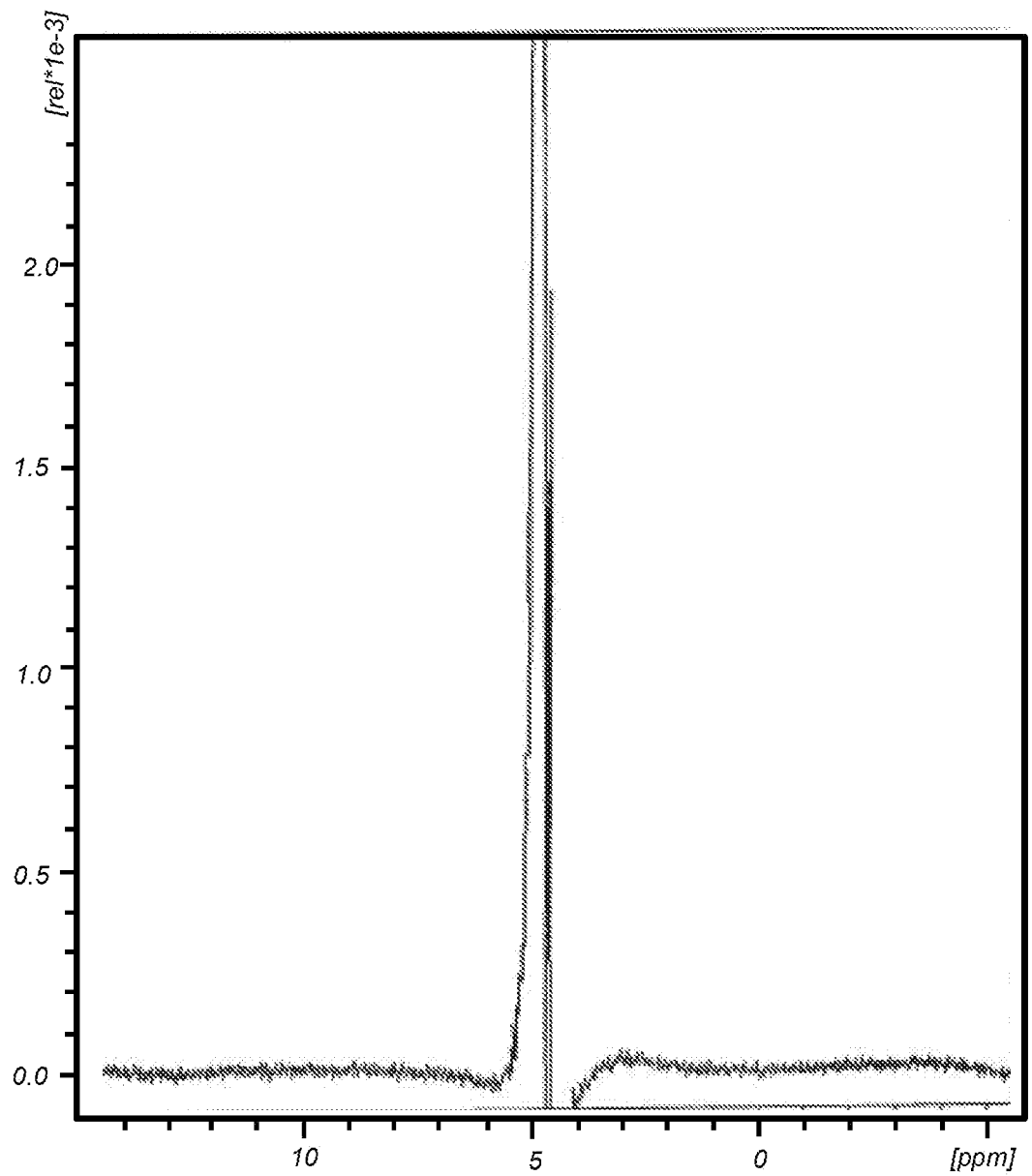
FIG. 6 illustrates a $^1H$ NMR spectrum of an electrolyzed saline solution for preparing a formulation of the present disclosure.

A $^1H$ NMR spectrum of the test sample was determined and is presented in FIG. 6. Only peaks associated with water were able to be distinguished from this spectrum. No peaks corresponding to organic material were detected. The spectrum shows that very little if any organic material can be detected in the composition using this method.

Phosphorous NMR and Mass Spectrometry

The electrolyzed saline solution sample was analyzed with phosphorous NMR and mass spectroscopy. DIPPMPO (5-(diisopropoxyphosphoryl)-5-1-pyrroline-N-oxide) (VWR) samples were prepared. A first test sample was prepared by measuring about 5 mg of DIPPMPO into a 2 ml centrifuge tube and adding 550 µL of the electrolyzed saline solution followed by 50 µL of $D_2O$. A control sample was prepared by measuring about 5 mg of DIPPMPO into a 2 ml centrifuge tube and adding 550 µL of water followed by 50 µL of $D_2O$. A second test sample was also prepared with the electrolyzed saline solution sample but without DIPPMPO. These solutions were vortexed and transferred to NMR tubes for analysis. Samples for mass spectrometry analysis were prepared by dissolving about 5 mg of DIPPMPO in 600 µL of the electrolyzed saline solution and vortexing and then diluting the sample by adding 100 µL of sample and 900 µL of water to a vial and vortexing.

NMR experiments were performed using a 700 MHz Bruker spectrometer equipped with a QNP cryogenically cooled probe. Experiments performed were a single 30° pulse at a 31p frequency of 283.4 MHz. A recycle delay of 2.5 seconds and 16384 scans were used. Phosphoric acid was used as an external standard. All experiments were performed at room temperature.

Mass spectrometry experiments were performed by directly injecting the mass spectroscopy sample into a Waters/Synapt Time of Flight mass spectrometer. The sample was directly injected into the mass spectrometer, bypassing the LC, and monitored in both positive and negative ion mode.

Figure 7:
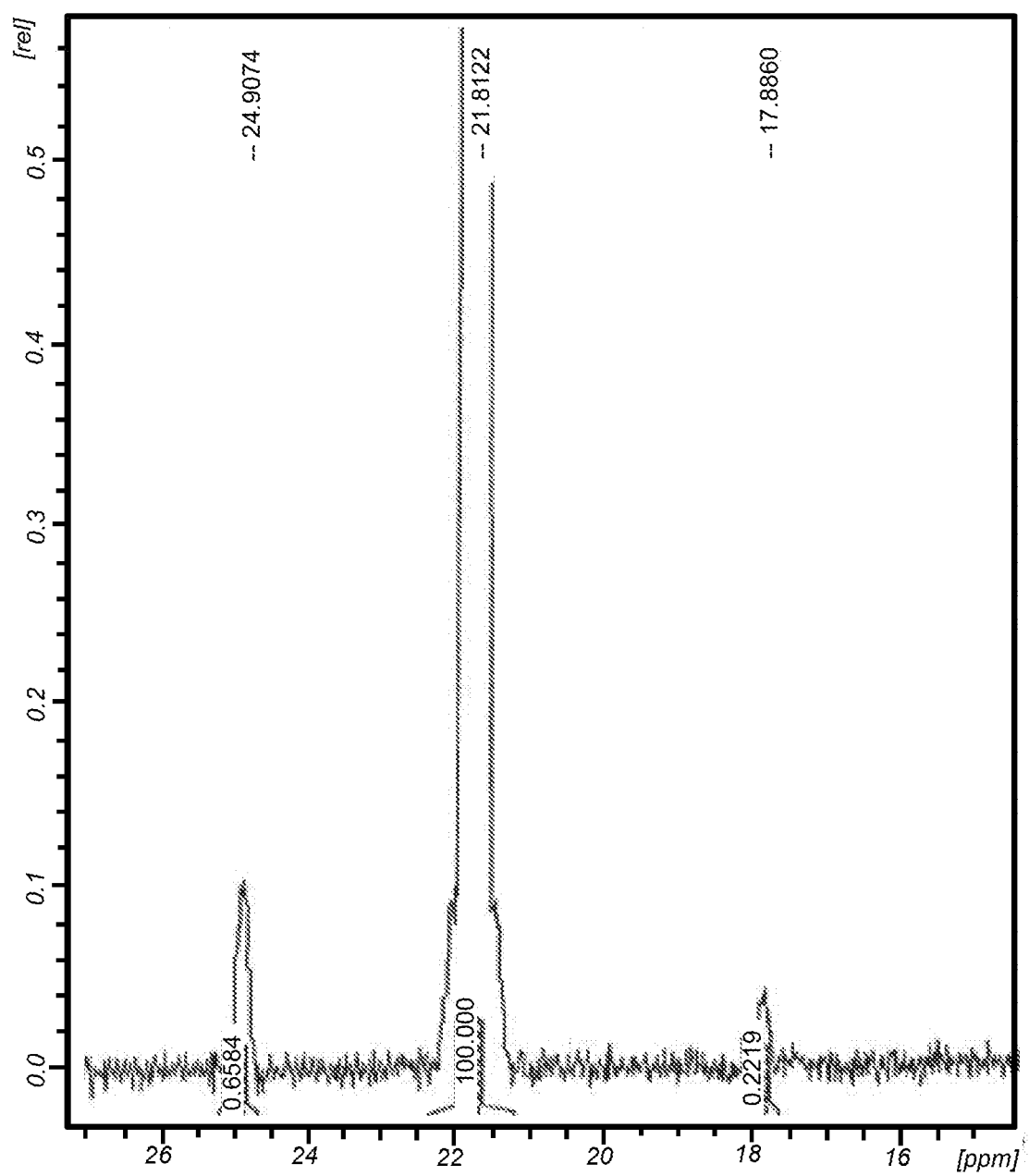
FIG. 7 illustrates a $^{31}P$ NMR spectrum of DIPPMPO combined an electrolyzed saline solution for preparing a formulation described herein.

The $^{31}P$ NMR spectra were collected for DIPPMPO in water, the electrolyzed saline solution sample alone, and the electrolyzed saline solution sample with DIPPMPO added to it. An external reference of phosphoric acid was used as a chemical shift reference. FIG. 7 illustrates a $^{31}P$ NMR spectrum of DIPPMPO combined with the electrolyzed saline solution sample. The peak at 21.8 ppm was determined to be DIPPMPO and is seen in both the spectrum of DIPPMPO with the electrolyzed saline solution sample (FIG. 7) and without the electrolyzed saline solution sample (not pictured). The peak at 24.9 ppm is most probably DIPPMPO/OH* as determined in other DIPPMPO studies. This peak may be seen in DIPPMPO mixtures both with and without the electrolyzed saline solution sample, but is detected at a much greater concentration in the solution with the electrolyzed saline solution sample. In the DIPPMPO mixture with the electrolyzed saline solution sample, there is another peak at 17.9 ppm. This peak may be from another radical species in the electrolyzed saline solution sample such as OOH· or possibly a different radical complex. The approximate concentrations of spin trap complexes in the electrolyzed saline solution sample/DIPPMPO solution are illustrated in Table 1:

TABLE 1

| Solution | Concentration |
| --- | --- |
| DIPPMPO | 36.6 mM |
| DIPPMPO/OH• | 241 µM |
| DIPPMPO/radical | 94 µM |

Figure 8:
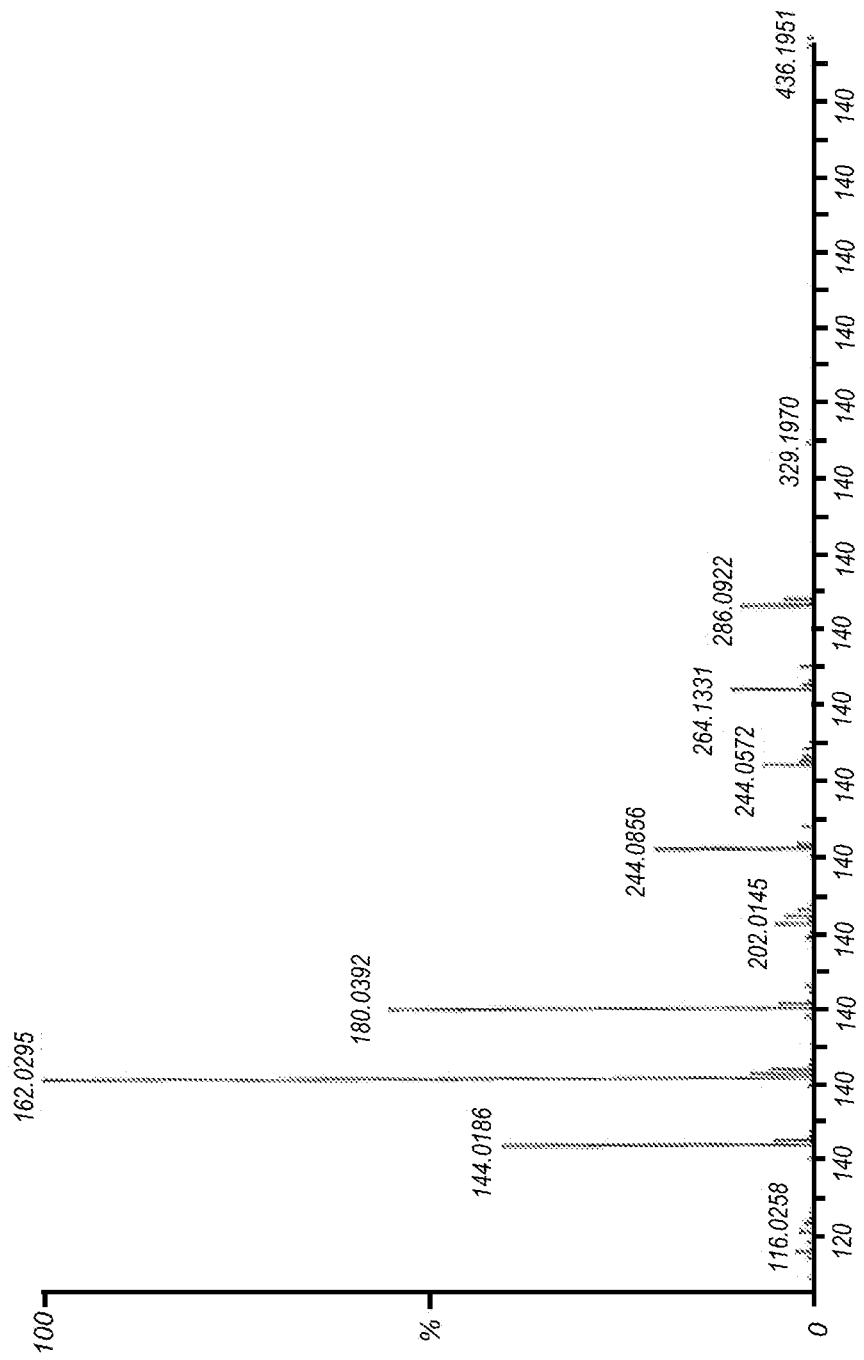
FIG. 8 illustrates a positive ion mode mass spectrum showing a parent peak and fragmentation pattern for DIPPMPO with m/z peaks at 264, 222, and 180 of an electrolyzed saline solution for preparing a formulation described herein.

Mass spectral data was collected in an attempt to determine the composition of the unidentified radical species. The mass spectrum shows a parent peak and fragmentation pattern for DIPPMPO with m/z peaks at 264, 222, and 180, as seen in FIG. 8. FIG. 8 also shows peaks for the DIPPMPO/Na adduct and subsequent fragments at 286, 244, and 202 m/z. Finally, FIG. 8 demonstrates peaks for one DIPPMPO/radical complex with m/z of 329. The negative ion mode mass spectrum also had a corresponding peak at m/z of 327. There are additional peaks at 349, 367, and 302 at a lower intensity as presented in FIG. 8. None of these peaks could be positively confirmed. However, there are possible structures that would result in these mass patterns. One possibility for the peak generated at 329 could be a structure formed from a radical combining with DIPPMPO. Possibilities of this radical species include a nitroxyl-peroxide radical (HNO—HOO·) that may have formed in the composition as a result of reaction with nitrogen from the air. Another peak at 349 could also be a result of a DIPPMPO/radical combination. Here, a possibility for the radical may be hypochlorite-peroxide (HOCl—HOO·). However, the small intensity of this peak and small intensity of the corresponding peak of 347 in the negative ion mode mass spectrum indicate this could be a very low concentration impurity and not a compound present in the electrolyzed saline solution sample.

ICP/MS Analysis

The electrolyzed saline solution sample was analyzed with inductively-coupled plasma mass spectroscopy to determine hypochlorite concentration. Samples were analyzed on an Agilent 7500 series inductively-coupled plasma mass spectrometer (ICP-MS). A stock solution of 5% sodium hypochlorite was used to prepare a series of dilutions of 300 ppb, 150 ppb, 75 ppb, 37.5 ppb, 18.75 ppb, 9.375 ppb, 4.6875 ppb, 2.34375 ppb, and 1.171875 ppb hypochlorite in deionized Milli-Q water. These hypochlorite standards were used to establish a standard curve.

Based on NMR hypochlorite concentration data, a series of dilutions were prepared of 164.9835 ppb, 82.49175 ppb, 41.245875 ppb, 20.622937 ppb, 10.311468 ppb, and 5.155734 ppb hypochlorite. These theoretical values were then compared with the values determined by ICP-MS analysis. The instrument parameters are listed in Table 2:

TABLE 2

| Elements analyzed | $^{35}Cl$ and $^{37}Cl$ |
| --- | --- |
| # of points per mass | 20 |
| # of repetitions | 5 |
| Total acquisition time | 68.8 s |
| Uptake speed | 0.50 rps |
| Uptake time | 33 s |
| Stabilization time | 40 s |
| Tune | No Gas |
| Nebulizer flow rate | 1 ml/min |
| Torch power | 1500 W |

The results of the ICP-MS analysis are listed in Table 3:

TABLE 3

| Dilution | Measured Concentration (ppb) | Concentration by NMR (ppb) |
|---|---|---|
| 1 | 81 | 82 |
| 2 | 28 | 41 |
| 3 | 24 | 21 |
| 4 | 13 | 10 |
| 5 | 8 | 5 |

Dilutions were compared graphically to the ICP-MS signals and fit to a linear equation ($R^2=0.9522$). Assuming linear behavior of the ICP-MS signal, the concentration of hypochlorite in the composition was measured to be 3.02 ppt. Concentration values were determined by calculating the concentration of dilutions of the initial composition and estimating the initial composition hypochlorite concentration to be 3 ppt (as determined from $^{35}Cl$ NMR analysis). The ICP-MS data correlate well with the $^{35}Cl$ NMR data, confirming a hypochlorite concentration of roughly 3 ppt. It should be noted that ICP-MS analysis is capable of measuring total chlorine atom concentration in solution, but not specific chlorine species. The NMR data indicate that chlorine predominantly exists as $ClO^-$ in the composition.

EPR

The electrolyzed saline solution sample was analyzed with electron paramagnetic resonance spectroscopy. Two different test samples were prepared for EPR analysis. The electrolyzed saline solution sample with nothing added was one sample. The other sample was prepared by adding 31 mg of DIPPMPO to 20 ml of the electrolyzed saline solution sample (5.9 mM), vortexing, and placing the sample in a 4° C. refrigerator overnight. Both samples were placed in a small capillary tube which was then inserted into a normal 5 mm EPR tube for analysis.

EPR experiments were performed on a Bruker EMX 10/12 EPR spectrometer. EPR experiments were performed at 9.8 GHz with a centerfield position of 3500 Gauss and a sweepwidth of 100 Gauss. A 20 mW energy pulse was used with modulation frequency of 100 kHz and modulation amplitude of IG. Experiments used 100 scans. All experiments were performed at room temperature.

Figure 9:
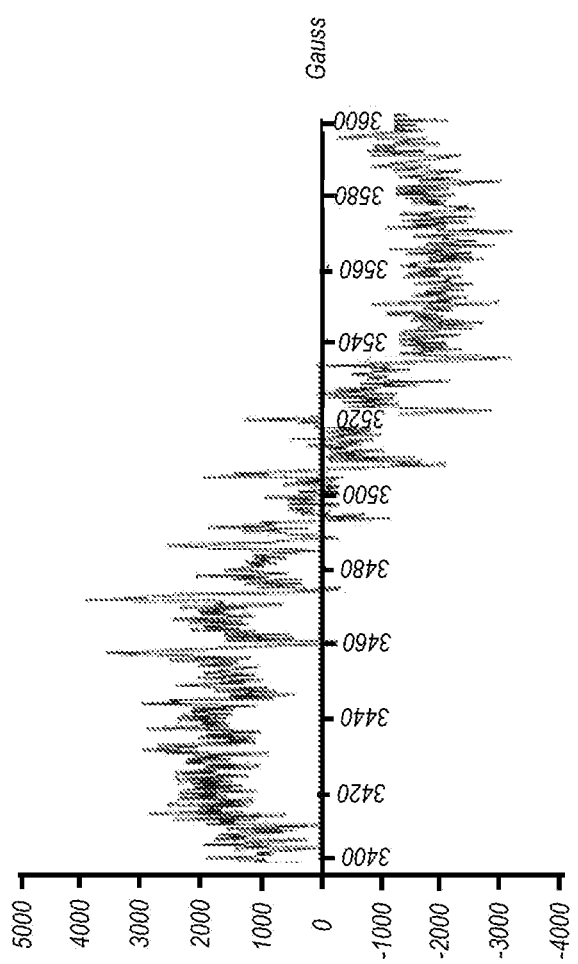
FIG. 9 illustrates an EPR spectrum for an electrolyzed saline solution sample for preparing a formulation described herein.

EPR analysis was performed on the electrolyzed saline solution sample with and without DIPPMPO mixed into the solution. FIG. 9 shows the EPR spectrum generated from DIPPMPO mixed with the electrolyzed saline solution sample. The composition alone showed no EPR signal after 100 scans (not presented). FIG. 9 illustrates an EPR splitting pattern for a free electron. This electron appears to be split by three different nuclei. The data indicate that this is a characteristic splitting pattern of OH-radical interacting with DMPO (similar to DIPPMPO). This pattern can be described by $^{14}N$ splitting the peak into three equal peaks and IH three bonds away splitting that pattern into two equal triplets. If these splittings are the same, it leads to a quartet splitting where the two middle peaks are twice as large as the outer peaks. This pattern may be seen in FIG. 9 twice, with the larger peaks at 3457 and 3471 for one quartet and 3504 and 3518 for the other quartet. In this case, the $^{14}N$ splitting and the $^1H$ splitting are both roughly 14 G, similar to an OH* radical attaching to DMPO. The two quartet patterns in FIG. 9 are created by an additional splitting of 47 G. This splitting is most likely from coupling to $^{31}p$, and similar patterns have been seen previously. The EPR spectrum in FIG. 9 indicates that there is a DIPPMPO/OH* radical species in the electrolyzed saline solution sample.

Potassium Iodide (KI) Titration with $Na_2S_2O_3$

The electrolyzed saline solution sample was analyzed by KI titration with $Na_2S_2O_3$. The titration was performed to determine the amount of $ClO^-$ in the electrolyzed saline solution by reacting $ClO^-$ in the electrolyzed saline solution with KI and acid to make $I_2$ and $Cl^-$. The $I_2$ is brown in color and becomes clear upon complete reaction with $S_2O_3^-$ and $2I^-$.

The reagents were KI (42 mM) in glacial acetic acid solution (KIGAA) and 0.100 M $Na_2S_2O_3$ solution. The 42 mM KI solution was prepared by adding 1.758 g of KI and 5 ml of glacial acetic acid to a 250 ml Erlenmeyer flask and bringing the volume to 250 ml with DI $H_2O$. 0.100 M $Na_2S_2O_3$ solution was created by adding 2.482 g of $Na_2S_2O_3$ to a 100 mL volumetric flask, then adding DI $H_2O$ until 100 ml was reached. Three samples of the electrolyzed saline solution were tested.

Sample 1: 50 ml of electrolyzed saline solution was added to 50 ml KIGAA and mixed. The burette was rinsed three times with DI $H_2O$ then rinsed with $Na_2S_2O_3$ and filled with $Na_2S_2O_3$ to 4 ml. Initial burette reading started at 6 ml and ended at 5.69 ml. A total of 0.31 ml was added to complete the titration. Results indicated about 16 ppm of $ClO^-$ ($3.1 \times 10^{-4}$ M $ClO^-$) was present in the test sample.

Sample 2: 75 ml electrolyzed saline solution was added to a 50 ml KIGAA and allowed to mix. Initial burette reading was 14 ml and final was about 13.55 ml. A total of 0.45 ml was added. Results indicated about 16 ppm of $ClO^-$ ($3.1 \times 10^{-4}$ M $ClO^-$) was present in the test sample.

Sample 3: 100 ml electrolyzed saline solution was added to 50 ml KIGAA. Initial burette reading was at 15 ml and the final reading was at about 14.37 ml. Approximately 0.63 ml was added in total. Results indicated about 16 ppm of $ClO^-$ ($3.1 \times 10^{-4}$ M $ClO^-$) was present in the test sample. After three sample tests it appears that the $ClO^-$ concentration of the electrolyzed saline solution is about to $3.1 \times 10^{-4}$ M or 16 ppm as determined by KI titration with $Na_2S_2O_3$.

Example 2

Characterization and Analysis of Electrolyzed Solution

An electrolyzed saline solution sample was analyzed with for ROS content and concentration by fluorescent assay. The electrolyzed saline solution sample was prepared as described above in Example 1, with the exception that the saline solution contained 9.1 g/L of sodium chloride. The electrolyzed saline solution sample was tested for superoxides and hypochlorites as described herein. Specifically, the presence of superoxides was tested with the Nanodrop 3300 and R-phycoerytherin (R-PE) as the reagent and the presence of hypochlorites was tested with the Nanodrop 3300 and aminophenyl fluorescein (APF) as the reagent. The tests revealed the presence of both superoxides as well as hypochlorites.

The assay was carried out with the fluorescent dyes, R-Phycoerytherin (R-PE), Hydroxyphenyl fluorescein (HPF) and Aminophenyl fluorescein (APF). These fluorescent dyes are commonly used to determine relative ROS concentrations inside active biological systems and cells. The dyes change fluorescence when exposed to certain ROS species. The resulting change in fluorescence can be correlated to the concentration of ROS present. 2/2'-Axobis (2-methylpropionamide) dihydrochloride, a molecule that produces known amounts of ROS, was used to generate a standard curve. This is not an absolute measurement, but provides a standard curve to determine ROS concentrations. The assay is linear over a 2 log 10 range of ROS concentrations. Saline solution was used as a negative control and AAPH (2,2'-Azobis (2-amidinopropane) dihydrochloride) served as a positive control.

Phycoerythrin and R-phycoerythrin were purchased from Sigma Chemical Corporation, St. Louis, MO. AAPH (2,2'-azobis(2-amidino-propane) dihydrochloride) was purchased from Wako Chemicals USA, Richmond, VA. An 8 or 16 place fluorescence reader manufactured by Pacific Technologies, Redmond, WA was used. Temperature was controlled at 37° C. during the 12-20 h experimental run. The samples were measured every 0.5 to 2 min. Appropriate cut-off filters were employed to detect the fluorescence emissions of the phycoerythrins. Data were collected to determine the relative change of fluorescence over the time course of the experiment. SigmaPlot Pro v. 7 software (SPSS Software, Chicago, IL) was used to determine the area under the curve. The area under the curve (AUC) are plotted against the log 10 mM AAPH concentration to provide a standard curve from which to estimate the levels of ROS in the electrolyzed saline samples. The concentrations of ROS for five different electrolyzed saline samples and for two control saline solution samples were then determined. The results are recorded below in Table 4.

TABLE 4

| Sample | Mean AUC | ROS Content mM AAPH equivalents |
|---|---|---|
| electrolyzed saline sample | 479 | 3.3 |
| electrolyzed saline sample | 543 | 2.2 |
| electrolyzed saline sample | 441 | 4.5 |
| electrolyzed saline sample | 523 | 2.98 |
| electrolyzed saline sample | 516 | 3.2 |
| Saline | 974 | 0.095 |
| Saline | 956 | 0.075 |

The control saline solutions always contained less than 0.1 mM AAPH equivalents of ROS. The electrolyzed saline samples always contained >1.0 mM ROS.

Example 3

Preparation of Topical Formulation

Topical formulations were prepared with metal silicate sold under the tradename LAPONITE XL21™ as a rheology modifier, dimethicone sold under the tradename DIMETHICONE SATIN™ as an additive, and sodium phosphate monobasic as the buffering agent. In general, the topical formulations were prepared by first preparing electrolyzed saline solution (ESS) as described above with a saline solution including 0.28 g/L of sodium chloride. The metal silicate was then dissolved in deionized water and then combined with the electrolyzed saline solution. The dimethicone and buffering agent were then added. The final pH and final hypochlorite levels of the topical formulations were measured.

The topical formulation was prepared by electrolyzing a large batch (125 to 250 gallons) 0.28% sodium chloride solution for 66 hours as described above. The hypochlorite concentration of the electrolyzed saline solution was measured by EPA method 334.0 and found to be about 220 ppm. The pH of the electrolyzed saline solution was found to be about pH 8.6. In a separate vessel, metal silicate (sold under the tradename Laponite XL21™) and deionized water were combined until the mixture thickened. The electrolyzed saline solution was combined with the gelled mixture of deionized water and Laponite XL21. Sodium phosphate monobasic and dimethicone were then added to the mixture. The final mixture resulted in the electrolyzed saline solution being diluted four-fold to result in a sodium chloride concentration of about 0.07%. The final Laponite XL21 concentration was about 3.25%. The final sodium phosphate monobasic concentration was about 0.2%. The final dimethicone concentration was about 5%. The final pH was between 6.7 and 7.4.

Example 4

Preparation of Wound Healing Compositions

The following example demonstrates the method of preparing the wound healing composition and various compositions or formulations thereof.

A wound healing composition was prepared with the ingredients as provided in Table 5. Hypochlorite or a salt or acid thereof was added to water, a blend of dimethicone and cyclomethicone, sodium magnesium silicate, hydrochloric acid, and sodium phosphate in the preparation of a wound healing composition.

TABLE 5

| Wound Healing Composition | |
|---|---|
| Ingredient | Quantity |
| Water and/or buffer | balance |
| Hypochlorite (12.5%) | 0.6% |
| Sodium Magnesium Silicate (as Laponite XL21) | 3.25% w/v |
| Sodium Phosphate; or | 0.2% w/v; |
| Hydrochloric Acid | 0.08% w/v |
| Dimethicone Satin | 5% w/v |

The wound healing composition described in Table 5 is used for the treatment of wounds, as described herein.

EMBODIMENTS

Additional and alternative embodiments are provided and described below. Some embodiments disclosed herein pertain to eye serum compositions including electrolyzed saline redox-balanced solutions and methods of using these eye serums. In some embodiments, is a topical formulation of electrolyzed saline redox-balanced solution configured to be applied to skin surrounding the eye. The electrolyzed saline redox-balanced solution includes a balanced mixture of chemically reduced and oxidized species including an electrolyzed saline solution containing reactive oxygen species (ROS) including one or more of chemically reduced and oxidized species including, but not limited to, hypochlorous acid (HOCl), hypochlorites (OCl⁻, NaClO), dissolved oxygen ($O_2$), chlorine ($Cl_2$), hydrogen ($H_2$) gas, hydrogen peroxide ($H_2O_2$), hydrogen ions (H⁺), hypochloride (ClO), superoxides (*$O_2^-$, $HO_2$), ozone ($O_3$), activated hydrogen ions (H⁻), chloride ions (Cl⁻), hydroxides (OH⁻), singlet oxygen (*$O_2$) and other forms of reactive oxygen species (ROS) such as *OCl and *HO⁻.

In some embodiments, eye serums are topical preparations that are formulated to treat the skin surrounding the eye. The skin surrounding the eye area can be distinct from skin found on the face or other parts of the body. Skin surrounding the eye area can be up to 89% thinner than skin found on other parts of the body and can be susceptible to damage and other conditions. Skin surrounding the eyes can be prone to wrinkling, crow's feet, appearance of fine lines, puffiness, and other similar conditions. The appearance of any of these conditions in the skin surrounding the eye can cause the sufferer to appear and/or feel older and less attractive. The sufferer can even experience embarrassment and/or self-consciousness from any of these or other similar conditions that affect the skin surrounding the eye.

Therefore, in some embodiments are provided compositions and methods to treat conditions that affect the skin surrounding the eye. Such compositions and methods are disclosed herein.

In some embodiments, the disclosed eye serum compositions, methods of preparing eye serum compositions, and methods of using eye serum compositions include methods for preparing a stable topical formulation that include electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; mirroring the target mixture of chemically reduced and oxidized species in the electrolyzed saline solution to the reduced species and reactive oxygen species found in a known biological system; adding a rheology modifier; adding a buffering agent; and adding a silicone oil. In other embodiments, the target mixture of chemically reduced and oxidized molecules includes one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. In other embodiments, mirroring further includes measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. In other embodiments, the stable topical formulation includes sodium chloride at a concentration of about 0.07% to about 0.28%. In other embodiments, the rheology modifier includes a metal silicate. In other embodiments, the buffering agent includes a phosphate buffer. In yet other embodiments, the silicone oil includes dimethicone.

In some embodiments, the disclosed eye serum compositions, methods of preparing eye serum compositions, and methods of using eye serum compositions include methods for preparing an eye serum composition including electrolyzing a saline solution having a sodium chloride concentration between about 0.05% and about 0.30% by weight using a voltage between about 0 V and about 30 V across an inert anode and a spaced apart inert cathode thereby generating a target mixture of chemically reduced and oxidized molecules within the saline solution; adding a rheology modifier; and adding a silicone oil. The rheology modifier can include a metal silicate. The metal silicate can include a sodium magnesium fluorosilicate. The silicone oil can include dimethicone. The eye serum can include a buffering agent. The method can include ensuring a final hypochlorite concentration of about 40 ppm.

In some embodiments, the disclosed eye serum compositions, methods of preparing eye serum compositions, and methods of using eye serum compositions include methods for treating a skin surrounding an eye including providing a subject; providing an eye serum including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; and applying the eye serum to a skin surrounding an eye of the subject. Applying the eye serum can include applying the formulation daily.

In some embodiments, the disclosed eye serum compositions, methods of preparing eye serum compositions, and methods of using eye serum compositions include a topical eye serum formulation including an electrolyzed saline solution including a target mixture of chemically reduced and oxidized molecules prepared by applying a voltage between about 0 V and about 30 V to a saline solution having a sodium chloride concentration between about 0.07% and about 0.28% by weight; a rheology modifier; a silicone oil; and a buffering agent, where the target mixture of chemically reduced and oxidized species in the electrolyzed saline solution mirrors the reduced species and reactive oxygen species found in a known biological system. The target mixture of chemically reduced and oxidized molecules can include one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. Mirroring can include measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. The stable topical formulation can include sodium chloride at a concentration of about 0.07% to about 0.28%. The rheology modifier includes a metal silicate. The buffering agent can include a phosphate buffer. The silicone oil can include dimethicone.

In some embodiments, the disclosed eye serum compositions, methods of preparing eye serum compositions, and methods of using eye serum compositions include a kit including an eye serum including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution. In some embodiments, the kit further includes one or more of a facial cleanser, a skin toner, and a moisturizer.

In some embodiments, are provided eye serum formulations (and/or compositions) containing redox-balanced mixtures of reactive oxygen species (ROS) and reduced species (RS), methods for making eye serum formulations which contain redox-balanced mixtures of ROS and RS, and methods of using these eye serum formulations which contain redox-balanced mixtures of ROS and RS.

In some embodiments, the eye serum formulations containing balanced mixtures of ROS and RS include any suitable topical formulation. In other embodiments, the topical formulations include any suitable formulation configured for topical application to a subject. In yet other embodiments, the topical formulations include any suitable formulation configured for topical application to skin surrounding an eye in the subject. For example, the topical formulations can include one or more of a liquid or a solid. In some cases the topical formulation can include a liquid, a spray, a spritz, a mist, a liquid configured to be applied via a wipe, or any other suitable liquid formulation. In other cases the topical formulation can include any suitable gel formulation. For example, in some embodiments, gel formulations include hydrogels, creams, ointments, emollients, balms, liniments, unguents, colloids, emulsions, dispersions, sols, sol-gels, salves, or the like, or combinations thereof.

In some embodiments, the topical formulations include at least one reactive oxygen species (ROS). ROS can include, but are not limited to superoxides ($O_2^{*-}$, $HO_2^*$), hypochlorites ($OCl^-$, HOCl, NaClO), hypochlorates ($HClO_2$, $ClO_2$, $HClO_3$, $HClO_4$), oxygen derivatives ($O_2$, $O_3$, $O_4^{*-}$), hydrogen derivatives (H2, $H^-$), hydrogen peroxide ($H_2O_2$), hydroxyl free radical ($OH^{*-}$), ionic compounds ($Na^+$, $Cl^-$, $H^+$, $OH^-$, NaCl, HCl, NaOH), chlorine ($Cl_2$), water clusters (n*$H_2$O-induced dipolar layers around ions), and combinations thereof. Some ROS can be electron acceptors and some can be electron donors.

In some embodiments, these topical formulations are used in the personal care or cosmetics industry and/or as cosmeceuticals. In other embodiments, these topical formulations are applied topically to the skin of a subject to treat various conditions. In yet other embodiments, these topical formulations are applied topically to treat conditions such as crow's feet, fine lines around the eyes, wrinkles, dark circles, dryness, sagging skin, and/or other similar conditions. In some embodiments, the topical formulations are configured to reduce the appearance of fine lines, reduce wrinkling, promote collagen production, rejuvenate skin, improve elasticity, reduce puffiness, even out skin tone, hydrate skin, firm skin, lift sagging skin, promote a healthier appearance, promote a younger-looking appearance.

In some embodiments, methods for making formulations which contain redox-balanced mixtures of ROS and RS include generating redox-balanced mixtures of ROS and RS which are similar to redox-balanced mixtures of ROS and RS that exist naturally inside healthy living cells and/or biological systems. The redox-balanced mixtures of ROS and RS can include signaling molecules that are the same as those that are naturally produced inside of living cells and/or biological systems. In other embodiments, methods for making formulations which contain redox-balanced mixtures of ROS and RS include first determining a balanced target mixture of redox-signaling molecules inherent to healthy cells and measuring the concentrations of the ROS and RS contained therein, usually with fluorescent indicators. This balanced target mixture can be representative of a known biological system. This balanced target mixture can then be replicated in the formulation by electrolyzing a saline solution while varying any suitable electrolysis parameter (e.g., temperature, flow, pH, power-source modulation, salt makeup, salt homogeneity, and salt concentration). The resulting electrolyzed saline solution (ESS) may then include the replicated, mimicked, and/or mirrored balanced target mixture. In other embodiments, the formulation can be verified to have a similar makeup as the balanced target mixture by measuring concentrations of the reactive molecules (e.g., ROS and RS) contained within the formulation. In some cases, the concentrations of the reactive molecules contained within the formulation can be measured by any suitable analytical methods. In other cases, the concentrations of ROS and RS contained within the formulation can be measured by fluorescent indicators (e.g., R-Phycoerythrin (R-PE), Aminophenyl Fluorescein (APF) and Hydroxyphenyl Fluorescein (HPF)).

In some embodiments, the known biological system includes one or more of the cells and/or tissue that include the skin surrounding the eye area. For example, the cells and/or tissue that include the skin surrounding the eye area can include one or more of an epidermis, a dermis, an epithelium, keratinocytes, Merkel cells, melanocytes, Langerhans cells, stratum corneum, stratum granulosum, stratum spinosum, stratum germinativum, basement membrane, and any other related cells or tissue.

In some embodiments, one or more of the fluorescent indicators, R-Phycoerythrin (RPE), Aminophenyl fluorescein (APF) and Hydroxyphenyl fluorescein (HPF) are used to measure concentrations of ROS and RS in the formulation. These fluorescent indicator molecules exhibit a change in fluorescence when they come into contact with specific redox species. These corresponding changes in fluorescence can then be measured using a fluorospectrometer to verify and quantify the existence and relative concentration of the corresponding redox species. A combination of measurements from these indicators can be utilized to measure the concentration of ROS and RS in the formulation. These ROS and RS measurements of the formulation can then be compared to ROS and RS measurements taken from the balanced target mixture. This comparison can then be used to vary any suitable electrolysis parameter (e.g., temperature, flow, pH, power-source modulation, salt makeup, salt homogeneity, and salt concentration) such that the ROS and RS measurements of the formulation approximate the ROS and RS measurements of the balanced target mixture. Any other suitable analytical technique can also be used to determine ROS and RS measurements of the formulation and/or ROS and RS measurements of the balanced target mixture to make a similar comparison and/or to vary any suitable electrolysis parameter (e.g., temperature, flow, pH, power-source modulation, salt makeup, salt homogeneity, and salt concentration) such that the ROS and RS measurements of the formulation approximate the ROS and RS measurements of the balanced target mixture.

In some embodiments, reactive oxygen species (ROS) and reduced species (RS) are generated by electrolysis of saline solutions. Electrolysis of saline solutions can be carried out by preparing a saline solution, inserting an inert anode and a spaced apart inert cathode into the saline solution, and applying a current across the electrodes. Some forms of electrolysis (e.g., electrolysis that utilizes a pulsing voltage potential) can generate and preserve a variety of ROS and RS molecules. These forms of electrolysis can facilitate generation of several generations of ROS molecules, including stabilized superoxides such as O2*-. In some embodiments, these types of electrolysis generate 1st, 2nd, and 3rd generations of ROS molecules.

FIG. 1 illustrates some embodiments of 1st, 2nd, and 3rd generations of ROS molecules. FIG. 1 illustrates a diagram of the generation of various ROS molecules at the inert anode and the inert cathode, respectively. The molecules depicted in the space between the electrodes depict some of the initial reactant molecules. The molecules depicted to the left of the anode and to the right of the cathode depict the ROS molecules produced at the respective electrodes and their electrode potentials. The diagram divides the generated ROS molecules into their respective generation (e.g., 1st, 2nd, and 3rd generation). The ROS molecules produced in a particular generation utilize the ROS molecules produced in a previous generation as the initial reactant molecules. For example, the 2nd generation ROS molecules utilize the 1st generation ROS molecules as the initial reactant molecules. Although FIG. 1 only depicts three generations of ROS molecules, additional generations of ROS molecules can also be generated.

In some embodiments, the compositions and/or topical formulations disclosed herein include any suitable ROS molecules generated by electrolysis of saline solutions. In other embodiments, the compositions and/or topical formulations include any suitable chemical entities generated by electrolysis of saline solutions. In yet other embodiments, the formulations include, but are not limited to, one or more of the ROS molecules and/or chemical entities depicted in FIG. 1.

In some embodiments, the formulations include one or more of superoxides ($O_2^{*-}$, $HO_2^*$), hypochlorites ($OCl^-$, $HOCl$, $NaClO$), hypochlorates ($HClO_2$, $ClO_2$, $HClO_3$, $HClO_4$), oxygen derivatives ($O_2$, $O_3$, $O_4^{*-}$), hydrogen derivatives (H2, $H^-$), hydrogen peroxide ($H_2O_2$), hydroxyl free radical ($OH^{*-}$), ionic compounds ($Na^+$, $Cl^-$, $H^+$, $OH^-$, $NaCl$, $HCl$, $NaOH$), chlorine ($Cl_2$), water clusters ($n*H_2O$-induced dipolar layers around ions), and any other variations. In other embodiments, the composition includes at least one species such as $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $OH^-$, $O_3$, $O_4^*$, $OH^{*-}$, $HOCl-O_2^{*-}$, $HOCl-O_3$, $O_2^*$, $HO_2^*$, $NaCl$, $HCl$, $NaOH$, water clusters, or a combination thereof.

In some embodiments, the formulations include at least one species such as $H_2$, $Cl_2$, $OCl^-$, $HOCl$, $NaOCl$, $HClO_2$, $ClO_2$, $HClO_3$, $HClO_4$, $H_2O_2$, $O_3$, $O_4^*$, $OH^{*-}$, $HOC-O_2^{*-}$, $HOCl-O_3$, $O_2^{*-}$, $HO_2^*$, water clusters, or a combination thereof. In some embodiments, the formulations include at least one species such as $HClO_3$, $HClO_4$, $H_2O_2$, $O_3$, $O_4^*$, $OH^{*-}$, $HOC-O_2^{*-}$, $HOCl-O_3$, $O_2^{*-}$, $HO_2^*$, water clusters, or a combination thereof. In some embodiments, the formulations include at least $O_2^{*-}$ and one $HOCl$.

In some embodiments, the formulations include $O_2$. In some embodiments, the formulations include $H_2$. In some embodiments, the composition can include $Cl^-$. In some embodiments, the composition can include $OCl^-$. In some embodiments, the composition can include $HOCl$. In some embodiments, the composition can include $NaOCl$. In one embodiment, the composition can include $HClO_2$. In some embodiments, the composition can include $ClO_2$. In some embodiments, the composition can include $HClO_3$. In one embodiment, the composition can include $HClO_4$. In one embodiment, the composition can include $H_2O_2$. In one embodiment, the composition can include $Na^+$. In one embodiment, the composition can include $Cl^-$. In one embodiment, the composition can include $H^+$. In one embodiment, the composition can include $H^*$. In one embodiment, the composition can include $OH^-$. In one embodiment, the composition can include $O_3$. In one embodiment, the composition can include $O_4^*$. In one embodiment, the composition can include $^1O_2$. In one embodiment, the composition can include $OH^{*-}$. In one embodiment, the composition can include $HOCl-O_2^{*-}$. In one embodiment, the composition can include $HOCl-O_3$. In one embodiment, the composition can include $O_2^-$. In one embodiment, the composition can include $HO_2^*$. In one embodiment, the composition can include $NaCl$. In one embodiment, the composition can include $HCl$. In one embodiment, the composition can include $NaOH$. In one embodiment, the composition can include water clusters. Embodiments can include combinations thereof.

In some embodiments, the formulation can include stable complexes of ROS molecules. In some instances, superoxides and/or ozones can form stable Van der Waals molecular complexes with hypochlorites. In other instances, clustering of polarized water clusters around charged ions can also have the effect of preserving hypochlorite-superoxide and hypochlorite-ozone complexes. In some cases, these types of complexes can be built through electrolysis on the molecular level on catalytic substrates and may not occur spontaneously by mixing together the individual components. In other cases, hypochlorites can be produced spontaneously by the reaction of dissolved chlorine gas ($Cl^-$) and water. As such, in a neutral electrolyzed saline solution, one or more of these stable molecules and complexes may be generated: dissolved gases (e.g., $O_2$, $H_2$, $Cl^-$); hypochlorites (e.g., $OCl^-$, $HOCl$, $NaOCl$); hypochlorates (e.g., $HClO_2$, $ClO_2$, $HClO_3$, $HClO_4$); hydrogen peroxide (e.g., $H_2O_2$); ions (e.g., $Na^+$, $Cl^-$, $H^+$, $H^-$, $OH^-$); ozone (e.g., $O_3$, $O_4^{*-}$); singlet oxygen (e.g., $^1O$); hydroxyl free radical (e.g., $OH^{*-}$); superoxide complexes (e.g., $HOCl-O_2^{*-}$); and ozone complexes (e.g., $HOCl-O_3$). One or more of the above molecules can be found within the compositions and composition described herein.

In some embodiments, the electrolysis of the saline solution is performed under varying parameters. As the parameters are varied, various different molecules at various different concentrations are generated. In some embodiments, the composition includes about 0.1 ppt (part per trillion), about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of $OCl^-$. In some embodiments, $OCl^-$ can be present at 3 ppt. In other embodiments, $OCl^-$ can be present at 1 to 100 ppm (parts per million) or from 10 to 30 ppm or from 16 to 24 ppm. In particular embodiments, $OCl^-$ is present at 16 ppm, 17 ppm, 18 ppm, 19 ppm, 20 ppm, 21 ppm, 22 ppm, 23 ppm, 24 ppm or 25 ppm. In other embodiments, $OCl^-$ can be the predominant chlorine containing species in the composition.

In some embodiments, the chlorine concentration in the compound includes about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

In some embodiments, the chloride species is present in a concentration from about 1400 to about 1650 ppm. In other embodiments, the chloride species can be present from about 1400 to about 1500 ppm or from about 1500 to about 1600 ppm or from about 1600 to about 1650 ppm. In other embodiments, the chloride anion can be present in an amount that is predetermined based on the amount of NaCl added to the initial solution.

In some embodiments, the sodium species is present in the formulation in a concentration from about 1000 to about 1400 ppm. In other embodiments, the sodium species is present in a concentration from about 1100 to about 1200 ppm; from about 1200 to about 1300 ppm or from about 1300 to about 1400 ppm. For example, the sodium species can be present at about 1200 ppm. In other embodiments, the sodium anion can be present in an amount that is predetermined based on the amount of NaCl added to the initial solution.

The composition generally can include electrolytic and/or catalytic products of pure saline that mimic redox signaling molecular compositions of the native salt water compounds found in and around living cells. The formulation can be fine-tuned to mimic or mirror molecular compositions of different biological media. The formulation can have reactive species other than chlorine present. As described, species present in the compositions and compositions described herein can include, but are not limited to $O_2$, $H_2$, $Cl_2$, $OCl^-$, $HOCl$, $NaOCl$, $HClO_2$, $ClO_2$, $HClO_3$, $HClO_4$, $H_2O_2$, $Na^+$, $Cl^-$, $H^+$, $OH^-$, $O_3$, $O_4^*$, $OH^{*-}$, $HOCl-O_2^{*-}$, $HOCl-O_3$, $O_2^*$, $HO_2^*$, $NaCl$, $HCl$, $NaOH$ $^1O$, and water clusters: $n*H_2O$-induced dipolar layers around ions, and any variations.

In some embodiments, the formulation is substantially stable. In other embodiments, the formulation is substantially stable which means, among other things, that one or more active ingredient(s) (e.g., ROS and/or RS) are present, measurable or detected throughout a shelf life of the formulation. In one embodiment, the ROS include one or more of superoxides and/or hydroxyl radicals. For example, in some embodiments the formulation may include at least some percentage of the ROS and RS that is present in the formulation after a certain number of years, such as at least 95% of the active ingredient(s) present in the formulation after 2 years, at least 90% of the active ingredient(s) present in the formulation after 3 years, at least 85% of the active ingredient(s) present in the formulation after 4 years, at least 80% of the active ingredient(s) present in the formulation after 5 years, at least 75% of the active ingredient(s) present in the formulation after 6 years, at least 70% of the active ingredient(s) present In the formulation after 7 years, at least 65% of the active ingredient(s) present In the formulation after 8 years, at least 60% of the active ingredient(s) present In the formulation after 9 years, at least 55% of the active ingredient(s) present in the formulation after 10 years and the like.

In some embodiments, ROS can include substantially stable oxygen radicals. For example, stable oxygen radicals can remain stable for about 3 months, about 6 months, about 9 months, about 12 months, about 15 months, about 18 months, about 21 months, between about 9 months and about 15 months, between about 12 months and about 18 months, at least about 9 months, at least about 12 months, at least about 15 months, at least about 18 months, about 24 months, about 30 months, about 50 months, about 100 months, about 200 months, about 300 months, about 400 months, about 500 months, about 1000 months, about 2000 months, or longer.

Stable oxygen radicals can be substantially stable. Substantially stable can mean that the stable oxygen radical can remain at a concentration greater than about 75% relative to the concentration on day 1 (day 1 meaning on the day or at the time it was produced), greater than about 80%, greater than about 85%, greater than about 90%, greater than about 95%, greater than about 96%, greater than about 97%, greater than about 98%, or greater than about 99% over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Substantially stable can mean that the stable oxygen radical can remain at a concentration greater than about 75% relative to the concentration on day 1 or the day is was produced, greater than about 80% relative to the concentration on day 1 or the day is was produced, greater than about 85% relative to the concentration on day 1 or the day is was produced, greater than about 90% relative to the concentration on day 1 or the day is was produced, greater than about 95% relative to the concentration on day 1 or the day is was produced, greater than about 96% relative to the concentration on day 1 or the day is was produced, greater than about 97% relative to the concentration on day 1 or the day is was produced, greater than about 98% relative to the concentration on day 1 or the day is was produced, or greater than about 99% relative to the concentration on day 1 or the day is was produced over a given time period as described above. For example, in one embodiment, the stable oxygen radical is at a concentration greater than about 95% relative to day 1 for at least 1 year. In another embodiment, the at least one oxygen radical is at a concentration greater than about 98% for at least 1 year. In other embodiments, the stable oxygen radical is greater than about 86% stable for at least 4 years, greater than about 79% stable for at least 6 years, greater than about 72% stable for at least 8 years, greater than about 65% stable for at least 10 years, or 100% stable for at least 20 years.

In still other embodiments, the stable oxygen radical is greater than about 95% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 96% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the stable oxygen radical is greater than about 97% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 98% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 99% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is 100% stable for at least 2 years, at least 3 years, at least 4 years, at least 5 years, at least 6 years, at least 7 years, at least 8 years, at least 9 years, at least 10 years, at least 15 years, or at least 20 years.

In some embodiments, the stability of the stable oxygen radicals is expressed as a decay rate over time. In other embodiments, substantially stable means a decay rate less than 1% per month, less than 2% per month, less than 3% per month, less than 4% per month, less than 5% per month, less than 6% per month, less than 10% per month, less than 3% per year, less than 4% per year, less than 5% per year, less than 6% per year, less than 7% per year, less than 8% per year, less than 9% per year, less than 10% per year, less than 15% per year, less than 20% per year, less than 25% per year, between less than 3% per month and less than 7% per year.

In some embodiments, stability of the stable oxygen radicals is expressed as a half-life. For example, the half-life of the stable oxygen radical can be about 6 months, about 1 year, about 2 years, about 3 years, about 4 years, about 5 years, about 10 years, about 15 years, about 20 years, about 24 years, about 30 years, about 40 years, about 50 years, greater than about 1 year, greater than about 2 years, greater than about 10 years, greater than about 20 years, greater than about 24 years, between about 1 year and about 30 years, between about 6 years and about 24 years, or between about 12 years and about 30 years.

In some embodiments, the stability of the stable oxygen radicals is expressed as a shelf life. For example, the composition can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

In some embodiments, the formulation is substantially free of organic matter. In other embodiments, substantially no organic material is present in the formulations as described. In yet other embodiments, organic material refers to organic compounds derived from the remains of organisms such as plants and animals and their waste products. In some embodiments, organic material refers to compounds such as proteins, lipids, nucleic acids, and carbohydrates. In yet other embodiments, substantially free of organic matter means less than about 0.1 ppt, less than about 0.01 ppt, less than about 0.001 ppt or less than about 0.0001 ppt of total organic material in the formulation.

In some embodiments, the formulations include any suitable salt. In other embodiments, the formulation includes one or more suitable salts. In some embodiments, the formulation includes sodium chloride. In other embodiments, the formulation includes one or more of lithium chloride, sodium chloride, potassium chloride, rubidium chloride, cesium chloride, magnesium chloride, calcium chloride, strontium chloride, copper chloride, copper sulfate, and iron chloride. In yet other embodiments, the salt includes one or more of a chloride salt, a phosphate salt, a nitrate salt, an acetate salt, a lithium salt, a sodium salt, a potassium salt, a magnesium salt, a calcium salt, and an iron salt.

In some embodiments, the salt includes one or more additives. Salt additives can include, but are not limited to, potassium iodide, sodium iodide, sodium iodate, dextrose, glucose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, lactate, phosphates, tris, borates, carbonates, citrates, and folic acid. In some embodiments, one or more additives are added at the salting step. In other embodiments, one or more additives are added at any point in the preparation of the electrolyzed saline solution. In yet other embodiments, one or more additives are added just prior to bottling.

In some embodiments, the prepared saline is generally free from contaminants, both organic and inorganic, and homogeneous down to the molecular level. In particular, because some metal ions can interfere with electro-catalytic surface reactions, it may be helpful for some metal ions to be removed and/or absent from the saline solution.

In another embodiment, the saline solution includes any suitable ionic soluble salt mixture (e.g., saline containing chlorides). In addition to NaCl, other non-limiting examples include LiCl, HCl, $CuCl_2$, $CuSO_4$, KCl, $MgCl_2$, $CaCl_2$, sulfates and phosphates. In some instances, strong acids such as sulfuric acid ($H_2SO_4$) and strong bases such as potassium hydroxide (KOH) and sodium hydroxide (NaOH) can be used as electrolytes due to their strong conducting abilities.

In some embodiments, the formulations include salt in any suitable concentrations. For example, the saline concentration in the electrolyzed solution can be about 0.01% w/v, about 0.02% w/v, about 0.03% w/v, about 0.04% w/v, about 0.05% w/v, about 0.06% w/v, about 0.07% w/v, about 0.08% w/v, about 0.09% w/v, about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v. In other embodiments, the formulation includes about 0.28% salt.

In some embodiments, the formulations include any suitable rheology modifier. For example, rheology modifiers can include Newtonian fluids and/or soft solids that respond with plastic flow rather than by deforming elastically in response to an applied force. In other embodiments, rheology modifiers are selected and used in the formulations based on the desired characteristics of the rheology modifier and on the compatibility of the rheology modifier with redox signaling molecular compositions. In yet other embodiments, rheology modifiers include thickening agents, viscosity modifiers and/or gelling agents (e.g., acrylic acid-based polymers, cellulosic thickeners, metal silicates, and any other suitable rheology modifiers). In some embodiments, the formulations include one or more acrylic acid-based polymers (e.g., high molecular weight, cross-linked, acrylic acid-based polymers, such as poly(acrylic acid), PAA, carbomer, or polymers having the general structure of $(C_3H_4O_2)_n$). In other embodiments, the acrylic acid-based polymers are cross-linked with suitable copolymers (e.g., allyl sucrose, allylpentaerythritol, or any other suitable copolymer). In yet other embodiments, suitable copolymers of acrylic acid can be modified by long chain ($C_{10}$-$C_{30}$) alkyl acrylates and can be cross-linked with copolymer (e.g., allylpentaerythritol). In some embodiments, acrylic acid polymers are converted to a salt to reach a desired viscosity. In some embodiments, rheology modifiers include any polymeric co-thickener (e.g., carboxymethyl cellulose, cellulose ethers, xanthan, guar, natural gums, polyurethanes, ASE and HASE polyacrylic acid polymers.

In some embodiments, rheology modifiers include any suitable natural clay. For example, rheology modifiers can include natural clays such as bentonite or other similar clays. In other instances, rheology modifiers can include hectorite.

In some embodiments, rheology modifiers include any suitable synthetic silicate clay. In other embodiments, synthetic silicate clay includes magnesium and sodium silicate. In other embodiments, rheology modifiers include any suitable metal silicate gelling agent. In yet other embodiments, the metal silicate gelling agent includes one or metal silicates including an alkali metal, an alkaline earth metal, or any combinations thereof. In some embodiments, suitable alkali metals or alkaline earth metals can include, but are not limited to, lithium, sodium, potassium, magnesium, calcium, and the like. In some embodiments, the metal silicate gelling agent can be a sodium magnesium silicate or a derivative thereof. In other embodiments, the metal silicate gelling agent can include sodium magnesium fluorosilicate. For example, the metal silicate sold under the tradename LAPONITE™ can be used as a rheology modifier. In some cases, the metal silicate sold under the tradename LAPONITE XL21™ can be used as a rheology modifier.

In some embodiments, the rheology modifier includes one or more colloidal layered silicates. In other embodiments, the rheology modifier includes one or more of lithium magnesium sodium silicate, lithium magnesium sodium silicate and tetrasodium pyrophosphate, and/or sodium magnesium fluorosilicate and tetrasodium pyrophosphate. In yet other embodiments, the rheology modifier includes one or more of a colloid, a gel, a temporary sol, and/or a permanent sol. In some embodiments, the rheology modifier includes a personal care grade colloidal layered silicate. In other embodiments, the rheology modifier includes one or more colloidal layered silicates sold under the tradenames LAPONITE RD™, LAPONITE RDS™, LAPONITE S482™, LAPONITE SL25™, LAPONITE EP™, LAPONITE JS™, LAPONITE XLG™, LAPONITE XLS™, LAPONITE XL21™, and LAPONITE D™.

In some embodiments, the rheology modifiers can be present in the hydrogel formulation in any suitable amount. In other embodiments, the formulation includes about 0.1% by weight to about 10% by weight of rheology modifier. In yet other embodiments, the amount of modifier can be from about 1.0% to about 5% by weight. In some embodiments, the amount of modifier can be 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.25%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight. In other embodiments, the amount of modifier is 1% or 2% by weight. In yet other embodiments, these weight percentages can be approximate and can be modified to achieve specific characteristics desired and/or required in the composition.

In some embodiments, the viscosity of the hydrogel formulation can be any suitable viscosity such that the formulation can be topically applied to a subject. In some embodiments, the viscosity of the hydrogel formulation can be in the range of about 1,000 to about 100,000 centipoise (cP). In some embodiments, the viscosity of the hydrogel can be 1,000 cP, 2,000 cP, 3,000 cP, 4,000 cP, 5,000 cP, 10,000 cP, 15,000 cP, 20,000 cP, 25,000 cP, 30,000 cP, 35,000 cP, 40,000 cP, 45,000 cP, 50,000 cP, 55,000 cP, 60,000 cP, 65,000 cP, 70,000 cP, 75,000 cP, 80,000 cP, 85,000 cP, 90,000 cP, or 95,000 cP. In some embodiments, the viscosity of the hydrogel can be in the range of about 1,000 cP to about 20,000 cP. In other embodiments, the viscosity of the hydrogel can be in the range of about 12,000 cP to about 20,000 cP. These viscosity ranges can be approximate and can be modified to achieve specific characteristics desired and/or required in the composition.

In some embodiments, the formulations include any suitable buffering agents. In other embodiments, any suitable buffering agent is employed to yield and maintain the desired pH of the formulation. In yet other embodiments, other buffers suitable for use in the hydrogel formulations described herein include, but are not limited to, salts and acids of acetate, borate, glutamate, citrate, tartrate, benzoate, lactate, histidine or other amino acids, gluconate, phosphate, malate, succinate, formate, propionate, and carbonate. In some embodiments, other buffering agents are used as generally known in the art (see Handbook of Cosmetic and Personal Care Additives, 2nd ed., Ashe et al. eds. (2002) and Handbook of Pharmaceutical Excipients, 4th ed., Rowe et al. eds. (2003)). In some embodiments, suitable buffering agents are either in liquid or solid form. In another embodiment, the buffering agent is an acid or salt of a phosphate compound. In some embodiments, the buffering agent is sodium phosphate. The sodium phosphate employed herein can be any suitable form of sodium phosphate including, for example, monobasic sodium phosphate, dibasic sodium phosphate, tetrasodium pyrophosphate, or combinations thereof. Likewise, suitable buffering agents can include any suitable form of potassium phosphate including, but not limited to, monobasic potassium phosphate, dibasic potassium phosphate, tetrapotassium pyrophosphate, or combinations thereof. In some embodiments, suitable buffering agents include one or more of citric acid, lactic acid, sodium dihydrogen phosphate, ammonia solution, sodium hydroxide, sodium silicate, primary amines, secondary amines, DMEA, AMP95, and DMAMP80.

In some embodiments, any suitable amount of buffering agent may be included in the formulation. In some embodiments, the amount of buffering agent present in the hydrogel formulations is from about 0.01 weight-percent to about 5.0 weight-percent, based on the weight of the formulation. In some embodiments, the buffering agent can be present in an amount of from about 0.1 weight-percent to about 1.0 weight-percent. In other embodiments, the amount of buffering agent present in the hydrogel formulations is 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.25%, 3.3%, 3.4%, 3.5%, 3.6%, 3.7%, 3.8%, 3.9%, 4%, 4.1%, 4.2%, 4.3%, 4.4%, 4.5%, 4.6%, 4.7%, 4.8%, 4.9%, or 5% by weight of the formulation.

In some embodiments, the pH of the formulation is any suitable pH. In other embodiments, the pH of the formulation is generally from about 3 to about 9. In some embodiments, the pH of the formulation can be from 5.0 to 8.0. In some embodiments, the pH of the formulation can be from 6.0 to 8.0. In some embodiments, the pH of the formulation is between about 7.0 and 8.0. In yet other embodiments, the pH of the formulation is between about 7.2 and 7.8. In some embodiments, the pH of the formulation is between about 6.5 and 7.7. In other embodiments, the pH of the formulation is between about 6.7 and 7.5. In yet other embodiments, the pH of the formulation is between about 6.7 and 7.4. In some embodiments, the pH of the formulation is 6.5, 6.6, 6.7, 6.8, 6.9, 7.0, 7.1, 7.2, 7.3, 7.4, or 7.5.

In some embodiments, the formulations may further contain additives such as colorants, fragrances, buffers, oils, moisturizers, emollients, peptides, vitamins, minerals, oils, hyaluronic acids, ceramides, glycerins, glycerols, glycols, alcohols, caffeine, alpha hydroxyl acids (glycolic acids), plant extracts, physiologically acceptable carriers and/or excipients, and the like. In some embodiments, suitable colorants may include, but are not limited to, titanium dioxide, iron oxides, carbazole violet, chromium-cobalt-aluminum oxide, 4-Bis[(2-hydroxyethyl)amino]-9, 10-anthracenedione bis(2-propenoic)ester copolymers, and the like. In some embodiments, any suitable fragrance can be used.

In some embodiments, additives include any component that improves the look and/or feel of the formulation. For example, an additive can be included in the formulation to impart a certain texture such as a silky, slippery, and/or satiny feel to the formulation. In some instances the additive can include any suitable organosilicon compound, silicone-based organic polymer, silicone oil, and/or polymerized siloxane. For example, the additive can include polydimethylsiloxane or dimethicone. In some instances, the additive can include dimethicone with a tradename of DIMETHICONE SATIN™. In other instances the dimethicone can have a formula of $C_6H_{18}OSi_2$. In some embodiments, the silicone polymers can include one or more cyclosiloxanes.

In some embodiments, the formulations include one or more additives in any suitable concentrations. For example, the one or more additives can be between about 0.1% w/v and 10% w/v of the formulation. The additive can also be between about 1% w/v and 8% w/v of the formulation. The additive can also be between about 2% w/v and 6% w/v. The additive can also be between about 4% w/v and 6% w/v. The additive can also be between about 1%, 2%, 3%, 4%, 5%, 6%, 7%, 8%, 9%, and 10% weight to volume of the formulation. In some embodiments, topical formulations including ROS and RS are produced in any suitable manner that results in a topical formulation containing effective amounts of ROS and RS. FIG. 2 illustrates embodiments of a process 10 for producing topical formulations including ROS and RS. Process 10 can include any suitable steps for producing topical formulations including ROS and RS. In some embodiments, process 10 includes an optional step 100 of preparing an electrolyzed saline solution, an optional step 200 of adding a rheology modifier, an optional step 300 of adding a buffering agent, an optional step 400 of adding an additive, and/or an optional step 500 of packaging the topical formulation. Optional steps 100, 200, 300, 400, and/or 500 can be carried out in any suitable order to produce topical formulations including ROS. For example, in some embodiments, rheology modifier is added to an electrolyzed saline solution, followed by addition of buffering agent, addition of additives, and packaging of the formulation. In other embodiments, buffering agent is added to the electrolyzed saline solution followed by rheology modifier. In yet other embodiments, rheology modifier and buffering agent are mixed together and then added to the electrolyzed saline solution. In some embodiments, electrolyzed saline solution, buffering agent, and additives are first mixed together and then rheology modifier is added.

In some embodiments, optional step 100 includes any suitable steps for preparing an electrolyzed saline solution CESS). In other embodiments, the electrolyzed saline solution is prepared as described herein. Methods of producing the electrolyzed saline solution can include one or more of preparing an ultra-pure saline solution, inserting a set of inert catalytic electrodes, and controlling temperature and flow while applying current across the electrodes to activate a modulated electrolytic process to form stable molecular moieties and complexes such as RS molecules and ROS molecules. In some embodiments, optional step 100 includes preparing an ultra-pure saline solution including about 2.8 g/L of sodium chloride, inserting a set of inert catalytic electrodes, and controlling temperature and flow while applying about 3 A of current across the electrodes, while maintaining the ultra-pure saline solution at or below room temperature during 3 minutes of electrolysis. In other embodiments, optional step 100 includes preparing an ultra-pure saline solution including about 9.1 g/L of sodium chloride, inserting a set of inert catalytic electrodes, and controlling temperature and flow while applying about 3 A of current across the electrodes, while maintaining the ultra-pure saline solution at or below room temperature during 3 minutes of electrolysis.

FIG. 3 illustrates embodiments of the optional step 100 for preparing an electrolyzed saline solution. The optional step 100 can include an optional step 102 of reverse osmosis, an optional step 104 of distillation, an optional step 106 of salting, an optional step 108 of chilling, an optional step 110 of electrolyzing, and/or an optional step 112 of storage and testing.

In some embodiments, the electrolyzed saline solution is prepared from water. This input water can be supplied from any suitable source. For example, water can be supplied from a variety of sources, including but not limited to, municipal water, spring water, filtered water, distilled water, microfiltered water, or the like.

In some embodiments, any suitable purification method is used to prepare the water. In other embodiments, any suitable purification method is used to remove contaminants from the water. For example, an optional step 102 of reverse osmosis filtration can be used to prepare the water. In some cases, reverse osmosis filtration includes removing contaminants from the input water by pretreating the input water with an activated carbon filter to remove the aromatic and volatile contaminants followed by reverse osmosis (RO) filtration to remove dissolved solids and most organic and inorganic contaminants. In some embodiments, the reverse osmosis process can be performed at a temperature of about 5° C., about 10° C., about 15° C., about 20° C., about 25° C., about 30° C., about 35° C., or the like.

In some embodiments, an optional step 104 of distillation is used. A distillation step can be used remove contaminants. In some instances, contaminants can be removed through the distillation step, resulting in dissolved solid measurement of less than 1 ppm. In addition to removing contaminants, distillation may also serve to condition the water with the correct structure and oxidation reduction potential (ORP) to facilitate the oxidative and reductive reaction potentials on the platinum electrodes in the subsequent electro-catalytic process. In some embodiments, the distillation process can vary, but can provide water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. In other embodiments the temperature of the distillation process can be performed at a temperature of about 5° C., about 10° C., about 15° C., about 20° C., about 25° C., about 30° C., about 35° C., or the like. In some embodiments, the distillation step can be repeated as needed to achieve a particular total dissolved solids level.

In some embodiments, optional step 100 includes one or more other known processes for water purification to reduce the amount of total dissolved solids. Other known processes for water can include filtration and/or purification process such deionization, carbon filtration, double-distillation, electrodeionization, resin filtration, microfiltration, ultrafiltration, ultraviolet oxidation, electrodialysis, or combinations thereof.

In some embodiments, water prepared by reverse osmosis, distillation, and/or other known processes is referred to as ultra-pure water. Ultra-pure water can have a total dissolved solids count of less than about 10 ppm, about 9 ppm, about 8 ppm, about 7 ppm, about 6 ppm, about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. In other embodiments, the reverse osmosis process and/or distillation process provide water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. The reverse osmosis process, the distillation process and/or other known processes can be repeated as needed to achieve a particular total dissolved solids level.

As shown in FIG. 4, in some embodiments, a system 20 is used to purify the water prior to reverse osmosis and/or distillation. System 20 can include a water source 22. The water source 22 can be directed to a carbon filter system 24. Carbon filter 24 can be configured to remove oils, alcohols, and other volatile chemical residuals and particulates from the water. The post-carbon filter water can then pass into a water softener 26. The water softener 26 can be configured with resin beds configured to remove dissolved minerals. Then, as described above, the post-water softener water can pass through reverse osmosis step 102 and distillation step 104.

Referring again to FIG. 3, in some embodiments, any suitable method is used to add salt to the water to prepare the saline solution. In other embodiments, any suitable method is used to add salt to the ultra-pure water. For example, as shown in FIG. 3, an optional step 106 of salting can be used to add salt to the water. The salt can be any salt and/or mixture of salts suitable for preparing a saline solution. The salt can be in any suitable form (e.g., unrefined, refined, caked, de-caked, or the like). In one embodiment, the salt includes a sodium chloride (NaCl). In other embodiments, the salt include one or more of lithium chloride, sodium chloride, potassium chloride, rubidium chloride, cesium chloride, magnesium chloride, calcium chloride, strontium chloride, copper chloride, copper sulfate, and iron chloride. In yet other embodiments, the salt includes one or more of a chloride salt, a phosphate salt, a nitrate salt, an acetate salt, a lithium salt, a sodium salt, a potassium salt, a magnesium salt, a calcium salt, and an iron salt.

In some embodiments, the salt includes one or more additives. Salt additives can include, but are not limited to, potassium iodide, sodium iodide, sodium iodate, dextrose, glucose, sodium fluoride, sodium ferrocyanide, tricalcium phosphate, calcium carbonate, magnesium carbonate, fatty acids, magnesium oxide, silicon dioxide, calcium silicate, sodium aluminosilicate, calcium aluminosilicate, ferrous fumarate, iron, lactate, phosphates, tris, borates, carbonates, citrates, and folic acid. In some embodiments, one or more additives are added at the salting step. In other embodiments, one or more additives are added at any point in the preparation of the electrolyzed saline solution. In yet other embodiments, one or more additives are added after electrolysis.

In some embodiments, the prepared saline is generally free from contaminants, both organic and inorganic, and homogeneous down to the molecular level. In particular, because some metal ions can interfere with electro-catalytic surface reactions, it may be helpful for some metal ions to be removed and/or absent from the saline solution.

In another embodiment, the saline solution includes any suitable ionic soluble salt mixture (e.g., saline containing chlorides). In addition to NaCl, other non-limiting examples include LiCl, HCl, $CuCl_2$, $CuSO_4$, KCl, $MgCl_2$, $CaCl_2$, sulfates and phosphates. In some instances, strong acids such as sulfuric acid ($H_2SO_4$) and strong bases such as potassium hydroxide (KOH) and sodium hydroxide (NaOH) can be used as electrolytes due to their strong conducting abilities.

In some embodiments, the salt(s) and any additive(s) are added in any suitable form to the water. In other embodiments, the salt(s) and any additive(s) are added in a solid form to the water. In yet other embodiments, the salt(s) and any additive(s) are added to the water in the form of a concentrated brine solution. A brine solution can be used to introduce the salt into the water. The brine solution can be prepared at any suitable concentration and can be diluted at any suitable ratio. In yet other embodiments, a brine solution of sodium chloride is used to salt the water. The brine solution can have a NaCl concentration of about 540 g NaCl/gal, such as 537.5 g NaCl/gal.

In some embodiments, the brine solution is prepared with one or more of a physical mixing apparatus and/or a circulation/recirculation apparatus. In one embodiment, pure pharmaceutical grade sodium chloride is dissolved in the ultra-pure water to form a 15% w/v sub-saturated brine solution and continuously re-circulated and filtered until the salt has completely dissolved and all particles >0.1 microns are dissolved. In some cases, the recirculation and filtration can be carried out for several days. The filtered, dissolved brine solution can then be injected into tanks of distilled water in about a 1:352 ratio (brine:salt water) in order to form a 0.3% saline solution.

In some embodiments, the brine solution is added to the water to achieve a salt concentration of between about 1 g/gal water and about 25 g/gal water, between about 8 g/gal water and about 12 g/gal water, or between about 4 g/gal water and about 16 g/gal water. In a preferred example, the achieved salt concentration is 2.8 g/L of water. In another preferred example, the achieved salt concentration is 9.1 g/L of water. Once brine is added to the water at an appropriate amount, the solution can be thoroughly mixed. The temperature of the liquid during mixing can be at room temperature or controlled to a desired temperature or temperature range. To mix the solution, a physical mixing apparatus can be used or a circulation or recirculation can be used.

In some embodiments, the saline solution is maintained at any suitable temperature for electrolysis. In other embodiments, the saline solution is chilled in an optional step 108 of a chilling step as shown in FIG. 3. The saline solution can be chilled in any suitable manner for electrolysis. In some embodiments, various chilling and cooling methods are employed. For example cryogenic cooling using liquid nitrogen cooling lines can be used. Likewise, the saline solution can be run through propylene glycol heat exchangers to achieve any desired temperature. The chilling method and/or chilling time can vary depending on one or more of the volume of the saline solution, the starting temperature, and the desired chilled temperature.

In some embodiments, the saline solution is chilled prior to electrolysis. In other embodiments, the saline solution is continuously chilled during electrolysis. In yet other embodiments, the saline solution is continuously chilled and recirculated during electrolysis.

In some embodiments, the saline solution is electrolyzed in any suitable manner to generate the electrolyzed saline solution. In other embodiments, the saline solution can undergo electrochemical processing through the use of at least one electrode in an electrolyzing step 110 of FIG. 3.

Each electrode can include a conductive metal. Electrode metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. I some embodiments, each electrode is formed of titanium and plated with platinum. The platinum surfaces on the electrodes by themselves can be optimal to catalyze the required reactions. The platinum plating can be configured as a rough, double layered platinum plating configured to assure that local "reaction centers" (sharply pointed extrusions) are active and prevent the reactants from making contact with the underlying electrode titanium substrate.

In one embodiment, rough platinum-plated mesh electrodes in a vertical, coaxial, cylindrical geometry are used, with, for example, not more than 2.5 ern, not more than 5 cm, not more than 10 cm, not more than 20 cm, or not more than 50 cm separation between the anode and cathode. The current run through each electrode can be between about 2 amps and about 15 amps, between about 4 amps and about 14 amps, at least about 2 amps, at least about 4 amps, at least about 6 amps, or any range created using any of these values. In one embodiment, 7 amps of current is applied across each electrode. In one example, 1 amp of current is run through the electrodes. In one example, 2 amps of current are run through the electrodes. In one example, 3 amps of current are run through the electrodes. In one example, 4 amps of current are run through the electrodes. In one example, 5 amps of current are applied to the electrodes. In one example, 6 amps of current are applied to the electrodes. In one example, 7 amps of current are applied to the electrodes. In a preferred example, 3 amps of current are applied to the electrodes.

In some embodiments, current is applied to the electrodes for a sufficient time to electrolyze the saline solution. The saline solution can be chilled during the electrochemical process. The solution can also be mixed during the electrochemical process. This mixing can be performed to ensure substantially complete electrolysis. In some embodiments, electrolysis products formed at the anode surface are effectively transported to the cathode surfaces to provide the reactants necessary to generate stable complexes on the cathode surfaces. Maintaining a high degree of homogeneity in the saline solution circulated between the catalytic surfaces can also be helpful to generate stable complexes. In some embodiments, a constant flow of about 2-8 ml/cm$^2$ per second of the saline solution can be used with typical a mesh electrode spacing of 2 cm. This constant flow of saline solution can be maintained, in part, by the convective flow of gasses released from the electrodes during electrolysis.

In some embodiments, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.5° C. throughout electrolysis. The temperature of the solution at the time or duration of the electrolysis can be below 10° C. In a preferred embodiment, the temperature of the solution at the time or duration of the electrolysis is 10° C. or 9° C. or 8° C. or 7° C. or 6° C. or 5° C. or 4° C. or 3° C. or 2° C. or 1° C. or −1° C. or −2° C. or −3° C. or −4° C. or −5° C. or −6° C. or −7° C. or −8° C. or −9° C. or −10° C. The temperature can be within a range as well such as between 1 to 10° C. or, 3 to 7° C. or 4 to 6° C. Preferably the temperature during electrolysis is from 4 to 6° C. Most preferably, the temperature during electrolysis is from 4.5 to 5.8° C.

In some embodiments, electric fields between the electrodes can cause movement of ions. This movement of ions can enable exchange of reactants and products between the electrodes. In some embodiments, no membranes or barriers are placed between the electrodes. In other embodiments, the electrolysis process is performed in a single container as a batch process.

The saline solution can be electrolyzed for an amount of time required based on the particular results desired. For example, the saline solution can be electrolyzed from about 1 minute to about 5 days. Preferably, the saline solution can be electrolyzed from about 20 minutes to about 2 days. More preferably, the saline solution is electrolyzed for 1-60 minutes for every 1 L, 10-40 minutes for every 1 L, or 20-30 minutes for every 1 L. For example, the saline solution can be electrolyzed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes or 60 minutes for each 1 μL of saline solution.

The saline solution can be electrolyzed for any amount of time in between 1 to 60 minutes for every 1 μL of saline solution. For example, the saline solution can be electrolyzed for a time between 1 and 2 minutes or for a time between 2 to 3 minutes etc. For example, the saline solution can be electrolyzed for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes or about 60 minutes for each 1 μL of saline solution. Most preferably the saline solution is electrolyzed for 15 to 25 minutes or any time in between. For example, the saline solution is electrolyzed for about 15 to about 25 minutes or any time in between.

The variables of voltage, amps, frequency, time and current required depend on the compound and/or ion themselves and their respective bond strengths. To that end, the variables of voltage, amps, frequency, time and current are compound and/or ion dependent and are not limiting factors. That notwithstanding, the voltage used can be less than 40V, such as 30V or 20V or 10V or any voltage in between. The voltage can also modulate and at any time vary within a range of from 1 to 40V or from 10 to 30V or from 20 to 30V. In one embodiment, the voltage can range during a single cycle of electrolyzing. The range can be from 1 to 40V or from 10 to 30V or from 20 to 30V. These ranges are non-limiting but are shown as examples.

Waveforms with an AC ripple also referred to as pulse or spiking waveforms include: any positive pulsing currents such as pulsed waves, pulse train, square wave, saw tooth wave, spiked waveforms, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid state diodes, silicon-controlled rectifiers and the like. Pulsed waveforms can be made with a transistor regulated power supply, a dropper type power supply, a switching power supply and the like.

A transformer may be used. Examples of transformers that can be used include center tapped transformers, auto-transformers, capacitor voltage transformers, distribution transformers, power transformers, phase angle regulating transformers, Scott-T transformers, polyphase transformers, grounding transformers, leakage transformers, resonant transformers, audio transformers, output transformers, laminated core toroidal autotransformers, variable autotransformers, induction regulators, stray field transformers, solyphase transformer, constant voltage transformer, ferrite core planar transformers, oil cooled transformers, cast resin transformers, isolating transformers, instrument transformers, current transformers, potential transformers, pulse transformers, air-core transformers, ferrite-core transformers, transmission line transformers, balun audio transformers, loudspeaker transformers, output transformers, small signal transformers, inter-stage coupling transformers, hedgehog or variocoupler transformers.

Pulsing potentials in the power supply of the production units can also be built in. Lack of filter capacitors in the rectified power supply can cause the voltages to drop to zero a predetermined amount of times per second. For example, at 60 Hz the voltage can spike 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals. In one embodiment, the pulsing potentials can vary based on the desired functional parameters and capabilities of the apparatus and equipment and to that end can vary from very high potentials to low potentials and from very high frequencies to very low frequencies. In one embodiment, the voltage potential must go down to zero periodically. The voltage can go to 0 V as many times per second as is physically possible. In some embodiments, the voltage is 0 V between 100 and 200 times per second. In a preferred embodiment, the voltage goes down to 0 V 120 times per second.

In some embodiments, there is no limit to the how high the voltage potential can go. For example, the voltage potential can pulse from 0V to 40V. In some embodiments, the voltage range can change or be changed so that the range changes as often or as little as desired within any given amount of time. This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second. When the V goes down to zero it is believe that the 0 V allows for ions to drift apart/migrate and reorganize before the next increase in V. It is theorized that this spiking in V allows for and promotes a variable range of frequencies influencing many different types of compounds and/or ions so that this process occurs.

In one embodiment, periodic moments of 0 volts are required. Again, when the V goes down to zero it is believe that the 0 V allows for ions to drift apart/migrate and reorganize before the next increase in V. Therefore, without being bound to theory, it is believed that this migration of ions facilitates the 1st, 2nd, and 3rd generations of species as shown in FIG. 1. Stabilized superoxides, such as $O_2^{*-}$, are produced by this method. In another embodiment, the V is always either zero or a positive potential. In some embodiments, diodes are used. The V may drop to zero as many times per second as the frequency is adjusted. As the frequency is increased the number of times the V drops is increased. The frequency can be from 1 Hz to infinity or to 100 MHz. Preferably, the frequency is from 20 Hz to 100 Hz. More preferably, the frequency is from 40 Hz to 80 Hz. Most preferably, the frequency is 60 Hz. In another embodiment, the frequency changes during the course of the electrolyzing process. For example, the frequency at any given moment is in the range from 20 Hz to 100 Hz. In another more preferred embodiment, the frequency at any given moment is in the range from 40 Hz to 80 Hz.

In some embodiments, after current has been applied to the saline solution for a suitable time, an electrolyzed solution is created. In other embodiments, an electrolyzed solution is created with beneficial properties (e.g., cellulite treating properties). The electrolyzed saline solution can be stored and/or tested for particular properties in an optional testing and storage step 112 of method 100.

In some embodiments, the electrolyzed saline solution is tested in any suitable manner for any suitable characteristics. For example, the electrolyzed saline solution can be subjected to quality assurance testing. Quality assurance test can include, without limitation, one or more of determination of pH, determination of presence of contaminants (e.g., heavy metals, chlorate, and/or any other contaminants), determination of oxidative reductive potential, determination of free chlorine concentrations, determination of total chlorine concentration, determination of reactive molecule concentration, and/or any other suitable testing. In some instances quality assurance testing is done on every batch after electrolysis. In some cases, a sample can be taken from each electrolysis batch and analyzed. Testing to determine the presence of contaminants such as heavy metals or chlorates can be performed. Additionally, pH testing, free chlorine testing, and total chlorine testing can be performed. In some cases, a chemical chromospectroscopic mass spectroscopy analysis can also be performed on the sample to determine if contaminants from the production process are present.

In some embodiments, the electrolyzed saline solution is tested for the presence of and/or concentration of ROS and RS species. For example, the electrolyzed saline solution can be assayed to determine if the electrolyzed saline solution mimics the desired balanced target mixture of redox-signaling molecules that are found in healthy living cells. If assays reveal that the electrolyzed saline solution mimics the desired balanced target mixture of redox-signaling molecules that are found in healthy living cells, the electrolyzed saline solution can then be used to prepare the topical formulation. If the assays reveal that the electrolyzed saline solution does not replicate the desired balanced target mixture of redox-signaling molecules that are found in healthy living cells, the batch can be rejected and a new batch of electrolyzed saline solution can be prepared while varying any suitable electrolysis parameter (e.g., temperature, flow, pH, power-source modulation, salt makeup, salt homogeneity, and salt concentration) such that the ROS and RS measurements of the electrolyzed saline solution can replicate the ROS and RS measurements of the balanced target mixture.

In some embodiments, one or more of the fluorescent indicators, R-Phycoerythrin (RPE), Aminophenyl fluorescein (APF) and Hydroxyphenyl fluorescein (HPF) are used to measure concentrations of ROS and RS in the electrolyzed saline solution. These fluorescent indicator molecules exhibit a change in fluorescence when they contact specific redox species. These corresponding changes in fluorescence can then be measured to verify and quantify the existence and relative concentration of the corresponding redox species. A combination of measurements from these indicators can be utilized to measure the concentration of ROS and RS in the electrolyzed saline solution. These measured concentrations of ROS and RS can then be compared to verify that the electrolyzed saline solution replicates the desired balanced target mixture of redox-signaling molecules that are found in healthy living cells.

In some embodiments, any suitable assay is used to determine if the electrolyzed saline solution replicates the balanced target mixture of redox-signaling molecules that are found in healthy living cells. For example, assays to measure the concentration of ROS and RS in the electrolyzed saline solution can include assays to measure pH, potassium iodide titration with $Na_2S_2O_3$ to determine $ClO^-$, inductively coupled plasma mass spectroscopy (ICP-MS) to detect metals and non-metals (e.g., to determine content of ions such as chlorine), $^{35}Cl$ NMR to determine content of ions such as chlorine, proton NMR to determine characteristics such as organic material content, and $^{31}P$ NMR to determine content of ions such as OH*. In other embodiments, any suitable assay is also used to determine the stability of the electrolyzed saline solution.

In some embodiments, the electrolyzed saline solution is used directly to prepare the topical formulation. In other embodiments, the electrolyzed saline solution is stored in any suitable manner before preparation of the topical formulation. For example, the electrolyzed saline solution can be stored at any suitable temperature in biocompatible containers. In some instances, the electrolyzed saline solution can be stored in non-reactive amber glass bottles. In other instances, the electrolyzed saline solution can be stored in non-reactive polymer bottles.

Referring again to FIG. 2, in some embodiments the formulation is prepared by adding one or more of rheology modifier, buffering agent, and/or additive(s) to the electrolyzed saline solution (e.g., as shown in optional steps 200, 300, 400, and 500). As described above, the addition of one or more of the components to the electrolyzed saline solution can be done in any suitable order or fashion.

In some embodiments, In optional step 200, rheology modifier is added to the electrolyzed saline solution in any suitable fashion to prepare the topical formulation. For example, the rheology modifier can be mixed with the electrolyzed saline solution to form a viscous solution before other components are added. In some instances, the rheology modifier can be added into the electrolyzed saline solutions as the solution is being mixed to allow for even dispersion of the rheology modifier. In other instances, purified water or any other suitable solution can be added to the mixture of electrolyzed saline solution and rheology modifier to achieve the desired viscosity.

In some embodiments, optional step 200 includes adding rheology modifier in any suitable amount to achieve the desired viscosity of the topical formulation. For example, the weight percent of the electrolyzed saline solution in the topical formulation can be from about 50% w/v to about 99.9% w/v. In some embodiments, the weight percent of the electrolyzed saline solution in the topical formulation is from about 90 to 99.1% by weight or from about 95 to 99.1%. In other embodiments, the weight percent of the electrolyzed saline solution in the topical formulation is about 95.1%, 95.2%, 95.3%, 95.4%, 95.5%, 95.6%, 95.7%, 95.8%, 95.9%, 96.0%, 96.1%, 96.2%, 96.3%, 96.4%, 96.5%, 96.7%, 96.8%, 96.9%, 97.0%, 97.1%, 97.2%, 97.3%, 97.4%, 97.5%, 97.6%, 97.7%, 97.8%, 97.9%, 98.0%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, or 99.9%. In yet other embodiments, weight percent of the electrolyzed saline solution in the topical formulation is about 98% or 99% by weight. These weight percentages can be approximate and can be modified to achieve specific characteristics desired and/or required in the topical formulation.

In some embodiments, the rheology modifier is added to the electrolyzed saline solution at any suitable temperature and/or at any suitable pH. For example, in some cases, a lower temperature may result in longer hydration times for the rheology modifier. Likewise, in some cases, a higher temperature may result in shorter hydration times. Therefore, in some instances, the temperature can be tailored to provide a suitable hydration time to prepare the topical formulation. In other embodiments, the pH of the rheology modifier and electrolyzed saline solution mixture is adjusted to achieve suitable hydration of the rheology modifier. For example, in the case of acrylic acid polymers, the mixture can be neutralized by addition of a strong base to form a polymer salt to achieve a suitable viscosity. In yet other embodiments, co-polymers are added to the rheology modifier to achieve a suitable viscosity. For example, copolymers such as allyl sucrose and/or allylpentaerythritol can be added to achieve a suitable viscosity.

In some embodiments, buffering agent includes any suitable buffering agent. As described above, the buffering agent can include any suitable buffering agent compatible with the topical formulation. In other embodiments, optional step 300 includes adding buffering agent to the topical formulation in any suitable manner. In some cases, the buffering agent is added to the mixture of rheology modifier and electrolyzed saline solution. In other cases, the buffering agent is added to the electrolyzed saline solution. In some embodiments, the buffering agent is prepared as a pH-adjusted stock solution that is added to the topical formulation. In other embodiments, the buffering agent is added as a solid. In yet other embodiments, the buffering agent is added to the topical formulation and then the pH is adjusted to a suitable pH. For example, a strong acid and/or a strong base can be added to the mixture of the buffering agent and other components to adjust the pH to a suitable pH. In some embodiments, the buffering agent is added to the topical formulation immediately before use.

In some embodiments, optional step 400 includes adding any suitable additive(s) in any suitable fashion to the topical formulation. In other embodiments, any suitable additive(s) are added at any point in process 10. Indeed, additives may be added at any point in the preparation of the electrolyzed saline solution (e.g., during salting, during chilling, and/or during electrolysis). Likewise, additives may be added before, during, and/or after adding rheology modifier, adding buffering agent and/or packaging. In yet other embodiments, additive(s) may be added to the topical formulation immediately before use In some embodiments, optional step 500 includes packaging the topical formulation in any suitable manner. Packaging can include dispensing the topical formulation into suitable containers. Suitable containers can include, without limitation, glass containers, amber glass containers, ceramic containers, polymer containers, squeeze bottles, squeeze tubes, squeezable pouches, manual pump dispenser, and any other suitable container. Packaging can include single use aliquots in single use packaging such as pouches. The topical formulation can be packaged in plastic bottles having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or any range created using any of these values. The plastic bottles can also be plastic squeezable pouches having similar volumes.

In some embodiments, packaging is generally free of any dyes, metal specks or chemicals that can be dissolved by acids or oxidizing agents. In other embodiments, any bottles, package caps, bottling filters, valves, lines and heads used in packaging are specifically rated for acids and oxidizing agents. In some cases, package caps with any organic glues, seals or other components sensitive to oxidation may be avoided since they could neutralize and weaken the product over time.

In some embodiments, the packaging used herein reduces decay of free radical species (ROS and/or RS) found within the topical formulations. In other embodiments, the packaging described does not further the decay process. In other words, the packaging used can be inert with respect to the ROS and/or RS species in the topical formulations. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of ROS and/or RS in the composition. In one embodiment, a bottle can only result in about 3% decay/month of superoxide. In another embodiment, a pouch can only result in about 4% decay/month of superoxide.

The present application provides methods of preventing and/or treating conditions that affect skin surrounding the eye by administering a therapeutic amount of the described topical formulation to a subject. In some embodiments, administering the topical formulation includes administering a therapeutic amount of the topical formulation to a subject in any suitable manner. A subject can include a human, a mammal, an animal, an animal kept as a pet, livestock, zoo animals, and the like. In other embodiments, the topical formulation is administered by topically applying a therapeutic amount of the formulation to the skin surrounding the eye of the subject. In yet other embodiments, the topical formulation is applied to areas of the subject's skin that surround the eye that are affected by a condition. For example, the topical formulation can be applied to areas of the subject's skin that are above the eye, that are below the eye, that are on either side of the eye, that are above the cheekbone, and that are adjacent to the eyelids. In some cases the topical formulation can be applied to the eyebrow, the eyelids, the skin adjacent to the inside corner of the eye, and the skin adjacent to the outside corner of the eye.

In some embodiments, the topical formulation is applied directly to an affected area of the subject's skin. In other embodiments, the topical formulation is applied directly to the affected area by one or more of a dropper, a brush, a cotton swab, an applicator stick, a roller ball applicator, as a mist or aerosol, as a transdermal patch, by wiping with a wipe, by spreading the topical formulation on the area with fingers, or by any other similar methods. The topical formulation can be applied to the affected area in any suitable therapeutic amount. In some embodiments, the topical formulation is be administered and/or applied to the subject in gram units such as from about 0.05 g to about 2 g or as desired by the subject. When applied to the subject, it can be applied once, twice, three times, four times or more a day. It can be applied every other day, every three days, every four days, every five days, every six days, every week, every two weeks, every three weeks, or every month. Each application to the subject can be about 0.05 g, about 0.06 g, about 0.07 g, about 0.08 g, about 0.09 g, about 0.1 g, about 0.2 g, about 0.3 g, about 0.4 g, about 0.5 g, about 0.6 g, about 0.7 g, about 0.8 g, about 0.9 g, about 1.0 g, about 1.1 g, about 1.2 g, about 1.3 g, about 1.4 g, about 1.5 g, about 1.6 g, about 1.7 g, about 1.8 g, about 1.9 g, or about 2.0 g. In one embodiment, the formulation can be applied to the subject at a rate of about 0.4 g once a day. In another embodiment, the formulation can be applied to the subject at a rate of about a pea-sized aliquot per eye per day.

In other embodiments, the administration and/or application to the subject can be acute or long term. For example, the composition can be administered to the subject for a day, a week, a month, a year or longer. In other embodiments, the composition can simply be applied to the subject as needed.

The present application provides methods of preventing and/or treating a condition affecting the skin adjacent to the eye by administering a therapeutic amount of the described topical formulation to a subject. In some embodiments, the topical formulation is administered by topically applying a therapeutic amount of the formulations to areas of the subject's skin that are adjacent to the eye. In other embodiments, the topical formulation is administered by topically applying a therapeutic amount of the formulations to areas of the subject's skin adjacent to the eye that are affected by crow's feet, fine lines, wrinkles, dark eye circles, puffy eye bags, puffiness, dryness, uneven skin tone, sun damage and/or sagging skin. In other embodiments, the topical formulation is administered by topically applying a therapeutic amount of the formulations to areas of the subject's skin to prevent one or more of crow's feet, fine lines, wrinkles, dark eye circles, puffy eye bags, puffiness, dryness, uneven skin tone, sun damage and/or sagging skin. For example, the topical formulation can be applied to one or more areas of the subject's skin that above the eye, that are below the eye, that are one either side of the eye, that are above the cheekbone, and that are adjacent to the eyelids. In some cases the topical formulation can be applied to the eyebrow, the eyelids, the skin adjacent to the inside corner of the eye, and the skin adjacent to the outside corner of the eye. In some cases, the topical formulation can be applied prophylactically to areas of the subject's skin such as above the eye, below the eye, on either side of the eye, above the cheekbone, adjacent to the eyelids, the eyebrow, the eyelids, the skin adjacent to the inside corner of the eye, and the skin adjacent to the outside corner of the eye.

In other embodiments, the preventing and/or treating with the topical formulation can be acute or long term. For example, the topical formulation can be administered to the subject for a day, a week, a month, a year or longer to prevent and/or treat conditions affecting the skin surrounding the eye. In some cases, the topical formulation can be administered daily for at least six weeks to treat the skin surrounding the eye. In other cases, the topical formulation can be administered daily for at least twelve weeks to treat the skin surrounding the eye. In other embodiments, the topical formulation can simply be applied to the subject as needed to prevent and/or to treat conditions affecting the skin surrounding the eye.

In some embodiments, treating the skin surrounding the eye includes applying the topical formulation to affected skin to increase elasticity of the skin at the treated area. In some cases, the elasticity of an area of skin surrounding the eye can be measured before treatment. The affected area can then be treated and the elasticity of the treated area can be measured. In other cases, the treated area can exhibit an increase in elasticity. In some instances, the increase in elasticity of the treated area can be up to about 1%, about 2%, about 3%, about 4%, about 5%, about 6%, about 7%, about 8%, about 9%, about 10%, about 15%, about 20%, about 25%, about 30%, about 35%, and about 40%. In other instances, the increase in elasticity can be seen after 1 day, after 2 days, after 3 day, after 4 days, after 5 days, after 6 days, after 1 week, after 2 weeks, after 3 weeks, after 4 weeks, after 5 weeks, after 6 weeks, after 7 weeks, after 8 weeks, after 9 weeks, after 10 weeks, after 11 weeks, after 12 weeks, after 13 weeks, after 14 weeks, and after 15 weeks.

In some embodiments, treating the skin surrounding the eye includes applying the topical formulation to the affected skin to decrease the appearance of wrinkles and fine lines in the treated area. In some cases, the appearance of fine lines and wrinkles in affected skin can be measured before treatment. The affected area can then be treated and the appearance of fine lines and wrinkles of the treated area can be measured. In other cases, the treated area can exhibit a decrease in the appearance of fine lines and wrinkles. In some instances, the decrease in appearance of fine lines and wrinkles of the treated area can be up to about 1%, about 2%, about 3%, about 4%, about 5%, about 6%, about 7%, about 8%, about 9%, about 10%, about 15%, about 20%, about 25%, about 30%, about 35%, and about 40%.

In some embodiments, treating the skin surrounding the eye includes methods for applying the topical formulation to the skin surrounding the eye. These methods can include one or more of: gently washing the face with a mild cleanser to ensure that the skin surrounding the eye is clean; dispensing a pea-sized amount of the topical formulation; applying the pea-sized amount of the topical formulation to a finger or applicator; dotting the topical formulation under the eye from one corner to the other corner; dotting the topical formulation along the top eyelid and underneath the eyebrow; gently tapping the dotted topical formulation to help the topical formulation absorb into the skin; and waiting for topical formulation to be absorbed.

In some embodiments, the topical formulation is used as part of a system of skin care management to prevent and/or treat conditions that affect the skin surrounding the eye. For example, in some embodiments, the system includes one or more of a cleanser, a toner, a moisturizer, and or an eye serum. In some embodiments, the cleanser is formulated to gently remove dirt, oil, makeup, and/or dead skin from the face. In other embodiments, the toner is formulated to rebalance the pH of the skin after washing with the cleanser. In yet other embodiments, the moisturizer is formulated to restore moisture to the skin. In some embodiment, the eye serum is formulated and applied as described above. In other embodiments, the system is configured to be effective against one or more of oily skin, dry skin, sensitive skin, sun-damaged skin, age-damaged skin, acne-affected skin, and combination skin.

Alternative Embodiments

A first embodiment includes a method for preparing a stable topical formulation including: electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; mirroring the target mixture of chemically reduced and oxidized species In the electrolyzed saline solution to the reduced species and reactive oxygen species found in a known biological system; adding a rheology modifier; adding a buffering agent; and adding a silicone oil.

In some embodiments of the first embodiment, the target mixture of chemically reduced and oxidized molecules includes one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. In some embodiments, mirroring further includes measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. In some embodiments, the stable topical formulation includes sodium chloride at a concentration of about 0.07% to about 0.28%. In some embodiments, the rheology modifier includes a metal silicate. In some embodiments, the buffering agent includes a phosphate buffer. In some embodiments, the silicone oil includes dimethicone.

A second embodiment includes a method for preparing an eye serum composition, the method including: electrolyzing a saline solution having a sodium chloride concentration between about 0.05% and about 0.30% by weight using a voltage between about 0 V and about 30 V across an inert anode and a spaced apart inert cathode thereby generating a target mixture of chemically reduced and oxidized molecules within the saline solution; adding a rheology modifier; and adding a silicone oil.

In some embodiments of the second embodiment, the rheology modifier includes a metal silicate. In some embodiments, the metal silicate includes a sodium magnesium fluorosilicate. In some embodiments, the silicone oil includes dimethicone. In some embodiments, the eye serum further includes a buffering agent. In some embodiments, the second embodiment further includes ensuring a final hypochlorite concentration of about 40 ppm.

A third embodiment includes a method for treating a skin surrounding an eye, the method including: providing a subject; providing an eye serum including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution; and applying the eye serum to a skin surrounding an eye of the subject.

In some embodiments of the third embodiment, the target mixture of chemically reduced and oxidized molecules includes one or more of hypochlorous acid, hypochlorites, dissolved oxygen, chlorine, hydrogen gas, hydrogen peroxide, hydrogen ion, hypochloride, superoxides, ozone, activated hydrogen ions, chloride ions, hydroxides, singlet oxygen, *OCl, and *HO$^-$. In some embodiments, the method further includes mirroring the target mixture of chemically reduced and oxidized species in the electrolyzed saline solution to the reduced species and reactive oxygen species found in a known biological system by measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. In some embodiments, the rheology modifier includes a metal silicate. In some embodiments, the metal silicate includes sodium magnesium fluorosilicate. In some embodiments, the eye serum further includes a phosphate buffer. In some embodiments, the eye serum includes a pH of about 6.7 to 7.4. In some embodiments, applying the eye serum includes applying the formulation daily.

A fourth embodiment includes a topical eye serum formulation including: an electrolyzed saline solution including a target mixture of chemically reduced and oxidized molecules prepared by applying a voltage between about 0 V and about 30 V to a saline solution having a sodium chloride concentration between about 0.07% and about 0.28% by weight; a rheology modifier; a silicone oil; and a buffering agent. In some embodiments, the target mixture of chemically reduced and oxidized species in the electrolyzed saline solution mirrors the reduced species and reactive oxygen species found in a known biological system.

In some embodiments of the fourth embodiment, the target mixture of chemically reduced and oxidized molecules includes one or more of hypochlorous acid, hypochlorites, dissolved oxygen, chlorine, hydrogen gas, hydrogen peroxide, hydrogen ions, hypochloride, superoxides, ozone, activated hydrogen ions, chloride ions, hydroxides, singlet oxygen, *OCl, and *HO$^-$. In some embodiments, mirroring further includes measuring concentrations of reactive oxygen species in the electrolyzed saline solution using a fluorospectrometer and at least one fluorescent dye selected from R-phycoerytherin, hydroxyphenyl fluorescein, and aminophenyl fluorescein. In some embodiments, the stable topical formulation includes sodium chloride at a concentration of about 0.07% to about 0.28%. In some embodiments, the rheology modifier includes a metal silicate. In some embodiments, the buffering agent includes a phosphate buffer. In some embodiments, the silicone oil includes dimethicone.

A fifth embodiment includes a kit including an eye serum including a silicone oil, a rheology modifier, and a electrolyzed saline solution, the electrolyzed saline solution prepared by electrolyzing a saline solution having a salt concentration between about 0.01% and about 1.0% by weight using a voltage between about 0 V and about 30 V across an inert anode and a spaced apart inert cathode thereby generating a target mixture of chemically reduced and oxidized molecules within the saline solution. In some embodiments, the kit further includes one or more of a facial cleanser, a skin toner, and a moisturizer.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a"

and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of treating a burn in a subject afflicted with a burn, the method comprising:
    applying to a burn a therapeutically effective amount of a formulation consisting of:
        an electrolyzed saline solution having a salt concentration between 0.1% and 1% by weight, hypochlorite present in an amount of between 0.6 and 1% w/v, hypochlorous acid, dissolved oxygen, chlorine, hydrogen gas, hydrogen peroxide, hydrogen ions, hypochloride, ozone, activated hydrogen ions, chloride ions, hydroxides, singlet oxygen, *OCl, *HO$^-$, and superoxides of *O$_2$— and HO$_2$;
        a buffer, wherein the formulation has a pH ranging from 6.7 to 7.5;
        sodium magnesium silicate; and
        dimethicone,
    wherein the formulation has an osmolality measurement ranging from about 22 mOsm/kg to about 54 mOsm/kg; and
    allowing the formulation to absorb into the burn, thereby treating the burn.

2. The method of claim 1, wherein applying comprises topically administering the formulation to the burn.

3. The method of claim 1, wherein the formulation is an ointment, cream, spray, gel, lotion, or solution.

4. The method of claim 1, wherein the formulation is applied to the burn at least once daily.

5. The method of claim 1, wherein the formulation is applied to the burn three times a day.

6. The method of claim 1, wherein a rate of healing of the burn is accelerated as compared to a rate of healing of a non-treated burn.

7. The method of claim 1, wherein the therapeutically effective amount is an amount effective to accelerate burn healing, promote burn closure, or cause burn regression.

8. The method of claim 1, wherein the applying the formulation reduces, attenuates, or prevents bacterial growth or infection in the burn.

9. The method of claim 1, wherein the buffer is in an amount of about 0.2% w/v, wherein the sodium magnesium silicate is in an amount of about 3.25% w/v, and wherein the dimethicone is in an amount of about 5.0% w/v.

10. The method of claim 1, wherein the buffer is an acetate, an ascorbate, a carbonate, a phosphate, a citrate, or an organic based buffer.

11. The method of claim 1, wherein the buffer comprises sodium phosphate monobasic.

12. A system for healing a burn, comprising:
    a wound dressing material having a therapeutically effective amount of a formulation applied thereto, wherein the wound is a burn,
    wherein the formulation consists of:
        an electrolyzed saline solution having a salt concentration between 0.1% and 1% by weight, hypochlorite present in an amount of between 0.6 and 1% w/v, hypochlorous acid, dissolved oxygen, chlorine, hydrogen gas, hydrogen peroxide, hydrogen ions, hypochloride, ozone, activated hydrogen ions, chloride ions, hydroxides, singlet oxygen, *OCl, *HO$^-$, and superoxides of *O$_2$— and HO$_2$;
        a buffer present in an amount of about 0.2% w/v, wherein the formulation has a pH ranging from 6.7 to 7.5;
        sodium magnesium silicate; and
        dimethicone,
    wherein the formulation has an osmolality measurement ranging from about 22 mOsm/kg to about 54 mOsm/kg.

13. The system of claim 12, wherein the wound dressing material is a bandage, a wipe, a gauze, a sponge, a mesh, or an absorbent wound dressing material.

14. The system of claim 12, wherein the hypochlorite is in an amount of about 0.6% w/v, wherein the buffer is in an amount of about 0.2% w/v, wherein the sodium magnesium silicate is in an amount of about 3.25% w/v, and wherein the dimethicone is in an amount of about 5.0% w/v.

15. The method of claim 1, wherein the burn is a thermal burn, a radiation burn, or a chemical burn.

16. The method of claim 1, wherein the formulation is applied to a wound dressing material prior to application to the burn.

17. A method of treating a burn on an individual, the method comprising:

topically applying to the burn a therapeutically effective amount of a formulation consisting of:

an electrolyzed saline solution having a salt concentration between 0.1% and 1% by weight, hypochlorite present in an amount of about 0.6% w/v, hypochlorous acid, dissolved oxygen, chlorine, hydrogen gas, hydrogen peroxide, hydrogen ions, hypochloride, ozone, activated hydrogen ions, chloride ions, hydroxides, singlet oxygen, *OCl, *HO$^-$, and superoxides of *O$_2$— and HO$_2$;

sodium phosphate present in an amount of about 0.2% w/v, wherein the formulation has a pH ranging from 6.7 to 7.5;

sodium magnesium silicate present in an amount of about 3.25% w/v; and dimethicone present in an amount of about 5% w/v, wherein the formulation has an osmolality measurement ranging from about 22 mOsm/kg to about 54 mOsm/kg; and allowing the formulation to absorb into the burn, thereby treating the burn.

18. The method of claim 17, wherein applying the formulation to the burn accelerates healing of the burn.

19. The method of claim 1, wherein the therapeutically effective amount of the formulation is in a range from about 0.1 g to about 1 g.

20. The method of claim 1, wherein the therapeutically effective amount of the formulation is in an amount of about 0.4 g.

* * * * *